(12) United States Patent
Rothenberg

(10) Patent No.: US 9,982,303 B2
(45) Date of Patent: May 29, 2018

(54) DETERMINATION OF EOSINOPHILIC ESOPHAGITIS

(71) Applicant: CHILDREN'S HOSPITAL MEDICAL CENTER, Cincinnati, OH (US)

(72) Inventor: Marc E. Rothenberg, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days. days.

(21) Appl. No.: 15/130,162

(22) Filed: Apr. 15, 2016

(65) Prior Publication Data
US 2016/0304960 A1  Oct. 20, 2016

Related U.S. Application Data

(63) Continuation of application No. 13/412,469, filed on Mar. 5, 2012, now abandoned, which is a continuation of application No. 13/132,884, filed as application No. PCT/US2006/016948 on May 3, 2006, now abandoned.

(60) Provisional application No. 60/677,375, filed on May 3, 2005.

(51) Int. Cl.
*C12Q 1/6883* (2018.01)
*C12Q 1/68* (2018.01)

(52) U.S. Cl.
CPC ...... *C12Q 1/6883* (2013.01); *C12Q 2600/112* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 2004/0033502 A1* | 2/2004 | Williams | A61K 31/00 435/6.12 |
| 2007/0059720 A9 | 3/2007 | Fuqua et al. | |
| 2009/0233275 A1* | 9/2009 | Rothenberg | G01N 33/6893 435/6.11 |
| 2012/0283117 A1 | 11/2012 | Rothenberg | |

FOREIGN PATENT DOCUMENTS

| WO | WO-2006/083390 A2 | 8/2006 |
| WO | WO-2006/083390 A3 | 8/2006 |
| WO | WO-2006/119343 A1 | 11/2006 |

OTHER PUBLICATIONS

Kihara et al. Cancer Res. 2001. 61:6474-6479.*
Kim et al. Cancer Research and Treatment. 2004. 36(4):207-213.*
Hardiman. Pharmacogenomics. 2004. 5(5):487-502.*
Kaur et al. Gastroenterology. 2002. 123:60-67.*

(Continued)

*Primary Examiner* — Joseph G. Dauner
(74) *Attorney, Agent, or Firm* — Mintz Levin Cohn Ferris Glovsky and Popeo, P.C.; Muriel Liberto, Esq.

(57) ABSTRACT

The disclosure provides methods and compositions for diagnosing a patient eosinophilic esophagitis, the methods based upon the patient's gene expression profile for a panel of genes. The methods can also be used to exclude a diagnosis of chronic esophagitis.

6 Claims, 9 Drawing Sheets

(56) References Cited

OTHER PUBLICATIONS

Konturek et al. Digestive Diseases and Sciences. 2004. 49(718):1075-1083.*
Hamoui et al. Arch Surg. 2004. 139:712-717.*
Gupta et al. The American Journal of Gastroenterology. 1998. 93(5):795-798.*
Mayo Clinic. Retrieved on Oct. 10, 207 form the internet: http://www.mayoclinic.org/diseases-conditions/eosinophilic-esophagitis/basics/treatment/con-20035681.*
American College of Gastroenterology. Retrieved on Oct. 10, 2017 from the internet: http://patients.gi.org/topics/eosinophilic-esophagitis/.*
American College of Allergy, Asthma and Immunology. Retrieved on Oct. 10, 2017 from the internet: http://acaai.org/allergies/types/food-allergies/types-food-allergy/eosinophilic-esophagitis.*
Attwood, S.E. et al., "Esophageal eosinophilia with dysphagia. A distinct clinicopathologic syndrome," Dig. Dis. Sci., vol. 38, p. 109-116, 1993.
Baker et al. Journal of the National Cancer Institute. 2003. 95(7):511-515.
Blanchard, Carine et al., "IL-13 involvement in eosinophilic esophagitis: Transcriptome analysis and reversibility with glucocorticoids," Dec. 2007, J Allergy Clin Immunol, vol. 120, pp. 1292-1300.
Blanchard, C., et al., "Eotaxin-3 and a Uniquely Conserved Gene-Expression profile in 117 Eosinophilic Esophagitis," The Journal of Clinical Investigation, vol. 116, No. 2, p. 536-547, 2006.
Blennow, Kaj, "Cerebrospinal Fluid Protein Biomarkers for Alzheimer's Disease," Apr. 2004, NeuroRx, vol. 1, No. 2, pp. 213-225.
Boon, Kathy et al., "Comparison of medulloblastoma and normal neural transcriptomes identifies a restricted set of activated genes," 2003, Oncogene, vol. 22, pp. 7687-7694.
Dellon, Evan S., "Eosinophilic esophagitis: diagnostic tests and criteria," Jul. 2012, Curr Opin Gastroenterol, vol. 28, pp. 382-388.
Fox, V.L., et al., "Eosinophilic esophagitis: its not just kid's stuff," Gastrointest. Endosc., vol. 56(2), p. 260-270, 2002.
Liacouras, Chris et al., "Eosinophilic esophagitis: Updated consensus recommendations for children and adults," Jul. 2011, J Allergy Clin Immunol, vol. 128, pp. 3-26.
Michaels et al. Lancet. 2005. 365:488-492.
Mishra, A., et al., "An etiological role for aeroallergens and eosinophils in experimental esophagitis," J. Clin. Invest., vol. 107, p. 83-90, 2001.
Peeters et al Apr. 2005 Veterinary Immunology and Immunopathology 104: 195-204.
Rothenberg, M.E., et al., "Pathogenesis and clinical features of eosinophilic esophagitis," J. Allergy Clin. Immunol., vol. 108, p. 891, 2001.
Simon. Journal of Clinical Oncology. 2005. 23(29): 7332-7341.
Slonim. Nature Genetics Supplement. 2002. 32:502-508.
Straumann, Alex, "Eosinophilic Esophagitis: a rapidly emerging disorder," Feb. 3, 2012, Swiss Med Wkly., 142:w13513, pp. 1-8.
International Search Report for PCT Application No. PCT/US2006/016948, filed May 3, 2006, 1 page.
U.S. Appl. No. 13/132,884, filed Jun. 3, 2011, by Rothenberg (copy not attached).

* cited by examiner

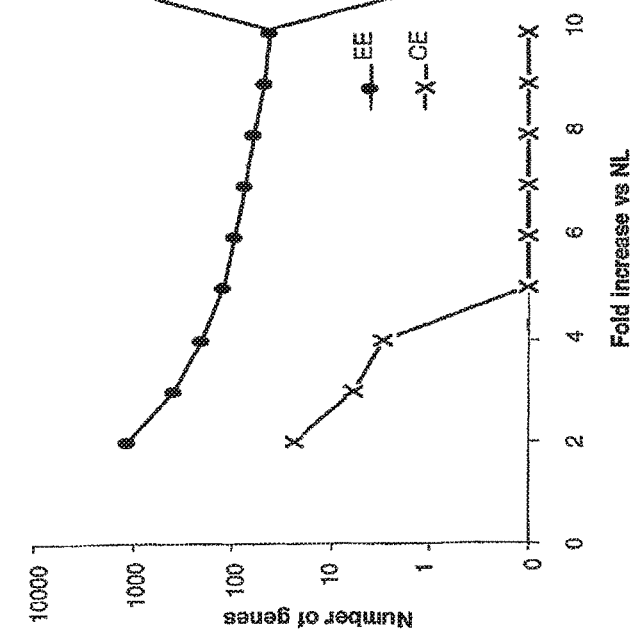

FIG. 3

| Accession # | Name[a] | Fold change |
|---|---|---|
| NM_006072 | chemokine (C-C motif) ligand 26 | 53.13 |
| NM_006475 | periostin, osteoblast specific factor | 47.18 |
| NM_007115 | tumor necrosis factor, alpha-induced protein 6 | 23.8 |
| NM_179960 | cadherin-like 26 | 23.64 |
| NM_001140 | arachidonate 15-lipoxygenase | 20.81 |
| NM_002674 | pro-melanin-concentrating hormone | 19.35 |
| NM_001511 | chemokine (C-X-C motif) ligand 1 | 18.76 |
| AK057174 | immunoglobulin lambda joining 3 | 17.75 |
| NM_018043 | transmembrane protein 16A | 17.47 |
| NM_145699 | apolipoprotein B mRNA editing enzyme, catalytic polypeptide-like 3A | 17.02 |
| AK090461 | immunoglobulin heavy constant gamma 1 (G1m marker) | 16.37 |
| XM_293626 | FLJ16025 protein | 15.09 |
| NM_006398 | ubiquitin D | 14.89 |
| NM_144646 | immunoglobulin J polypeptide, linker protein for immunoglobulin | 14.76 |
| NM_144649 | hypothetical protein FLJ33069 | 14.03 |
| NM_001870 | carboxypeptidase A3 (mast cell) | 13.12 |
| BX647333 | similar to immunoglobulin kappa light chain variable region O11 | 12.81 |
| NM_001828 | Charcot-Leyden crystal protein | 12.69 |
| AK090461 | hypothetical protein MGC27165 | 12.65 |
| NG_000002 | immunoglobulin lambda joining 3 | 12.42 |
| NM_145753 | pleckstrin homology-like domain, family B, member 2 | 12.09 |
| NM_024727 | hypothetical protein FLJ23259 | 10.99 |
| BX647533 | immunoglobulin kappa constant | 10.25 |
| NM_031308 | epiplakin 1 | 10.19 |
| NM_002993 | chemokine (C-X-C motif) ligand 6 | 10.08 |
| AL356504 | filaggrin | 0.0968 |
| NM_012307 | erythrocyte membrane protein band 4.1-like 3 | 0.0966 |
| NM_014758 | sorting nexin 19 | 0.0947 |
| NM_006025 | 26 serine protease | 0.0937 |
| NM_016280 | carboxylesterase 1 (monocyte/macrophage serine esterase 1) | 0.0881 |
| NM_021957 | glycogen synthase 2 (liver) | 0.0656 |
| NM_001785 | cytidine deaminase | 0.0588 |
| BF514741 | GSGL541 | 0.0552 |
| NM_006061 | cysteine-rich secretory protein 3 | 0.0312 |

[a]This list includes 8 transcripts that were found twice in the EE transcriptome.

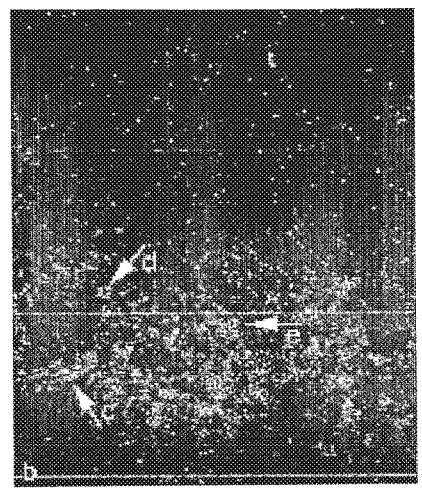
FIG. 7A  FIG. 7B
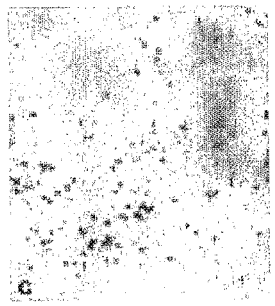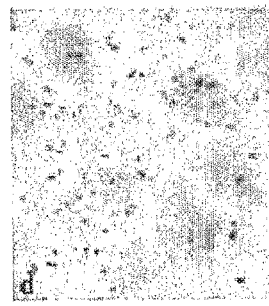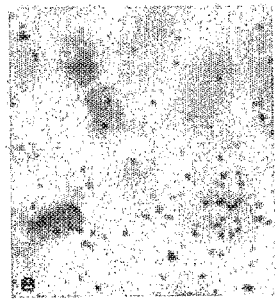
FIG. 7C  FIG. 7D  FIG. 7E
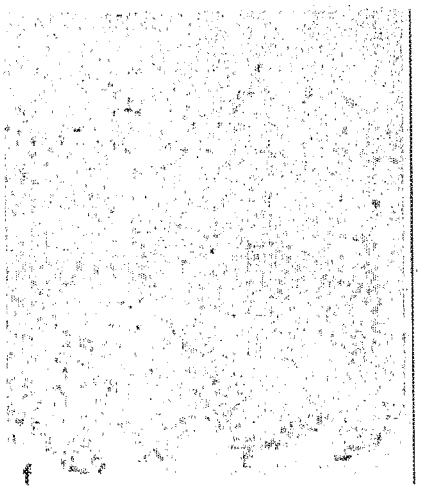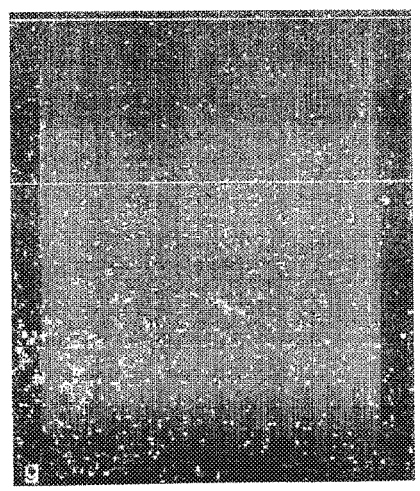
FIG. 7F  FIG. 7G

DETERMINATION OF EOSINOPHILIC ESOPHAGITIS

CROSS REFERENCE TO RELATED APPLICATIONS

This application is a continuation of U.S. patent application Ser. No. 13/412,469 filed Mar. 5, 2012, which is a continuation of U.S. patent application Ser. No. 13/132,884 filed Jun. 3, 2011, which is a U.S. National Stage entry under 35 U.S.C. § 371 of International Application No. PCT/US2006/016948, filed May 3, 2006, designating the United States of America, which in turn claims priority from U.S. Provisional Application Ser. No. 60/677,375, filed May 3, 2005, each of which is expressly incorporated by reference herein.

This invention was made with government support under AI045898 awarded by the National Institutes of Health. The government has certain rights in the invention.

INCORPORATION BY REFERENCE OF SEQUENCE LISTING

The present application contains a sequence listing which has been submitted in ASCII format via EFS-Web. The content of the computer readable ASCII text file named "47108-509C02US_ST25.bd", which was created on Jun. 23, 2016 and is 2.46 KB in size.

BACKGROUND

Eosinophilic esophagitis (EE) is an emerging worldwide disease, as documented by recent case series from Switzerland, Australia, Canada, Japan, England, and the U.S. Of concern, EE appears to be a growing health problem with an annual incidence of at least 1:10,000 children. The primary symptoms of EE (chest and abdominal pain, dysphagia, heartburn, vomiting, and food impaction) are also observed in patients with chronic esophagitis (CE) including gastroesophageal reflux disease (GERD). EE poses considerable diagnostic and therapeutic challenges especially because esophageal eosinophilia has been associated with several other medical condition including GERD, parasitic infection, and hypereosinophilic syndromes. In contrast to GERD, EE is more likely in males (80%), appears to have a not uncommon familial form, has a high rate of associated atopic disease (70%), and is typically not associated with abnormal pH probing of the esophagus. Distinguishing EE from GERD is important since EE patients typically do not respond to anti-GERD therapy, but rather respond to anti-inflammatory therapy and/or allergen elimination. Whereas both GERD and EE are associated with esophageal eosinophils, the level of eosinophils in EE is much higher; it has been proposed that the diagnosis of EE requires greater than 24 eosinophils per high-powered field (×40) from an esophageal tissue biopsy since these levels have been associated with non-responsiveness to anti-GERD therapy. However, whether GERD and EE representative a continuum, with EE being a more severe manifestation has not been addressed. A more clear differentiation between these various esophagitis states is needed.

Experimental dissection of experimental EE models in mice have revealed that EE can be triggered by both food and aeroallergens, particularly when the esophageal disease is co-induced with respiratory inflammation. However, nearly 25% of patients with EE are non-atopic individuals with no identifiable allergic sensitization. A question is to understand the relationship between the atopic and non-atopic variants of EE; whether atopic and non-atopic esophagitis involves similar effector pathways has implications for therapeutic strategies. Murine modeling has established that EE is a Th2 associated disease. IL-5 is required for disease pathogenesis; a humanized anti-IL-5 appears to be effective in an early clinical study. Human EE is associated with over-production of the Th2 cytokines IL-4 and IL-13. However, although these Th2 cytokines have been implicated, the mechanism by which they lead to esophageal eosinophilia is unclear. While IL-4 and IL-13 are known to induce the eosinophil specific eotaxin chemokines (e.g. eotaxin-1, eotaxin-2, eotaxin-3), their role has remained elusive since they have yet been demonstrated to be over-produced in EE and eotaxin-1 deficient mice only develop a modest attenuation of experimental EE. Based on homology with allergic inflammation in the lung, which involves the interplay of at least 17 chemokines including all three eotaxins, the inflamed esophagus may also involve a myriad of chemokines, with no dominance of a single chemokine.

SUMMARY OF THE INVENTION

Eosinophilic Esophagitis (EE) gene expression profiles and distinctions from chronic esophagitis (CE) are disclosed. Expression profiling of esophageal biopsy tissue from patients with EE compared to patients with CE, as well as healthy controls was performed. Whole genome wide expression analysis demonstrated an EE transcript signature that was similar across gender and patient age, but distinct from CE. Atopic and non-atopic variants of EE had a conserved esophageal transciptome indicating overlapping effector pathways in the diseased tissue of these patients. The most induced transcript in EE was eotaxin-3; levels of eotaxin-3 strongly correlated with disease severity and a single nucleotide polymorphism (SNP) in the eotaxin-3 gene conferred disease susceptibility. Protection from experimental EE was observed in mice harboring a genetic deletion in the eotaxin-3 receptor (CCR3).

BRIEF DESCRIPTION OF THE DRAWINGS

FIG. 3 shows the number of modified genes and their fold-change in EE and CE. The average gene expression levels in EE and CE groups were compared to the average gene expression in the NL group. The number of genes that changed 2-10-fold or more is shown. The list of the 42 transcripts that was modified ≥10-fold in EE compared with NL groups, and their GeneBank accession number is shown.

FIG. 7A-7G show eotaxin-3 expression in the esophagus of EE individuals. Esophageal sections were subjected to in situ hybridization using the eotaxin-3 anti-sense probe. The hybridization signal of the eotaxin-3 anti-sense (AS) and sense (S) probe are shown in an esophageal EE patient biopsy (a, b, c, d, e, f and g). Brightfield (a, c, d, e and f) and darkfield images (b and g) are shown at 40× (a, b, f and g) and 100× (c, d and e) magnification. The darkfield signal is white/pink and the brightfield signal is black. In the paired dark and bright field photomicrographs arrows show the epithelial eotaxin-3 expression. The hybridization of the S probe to the same biopsies is shown in f and g.

DETAILED DESCRIPTION

Figure 1B:
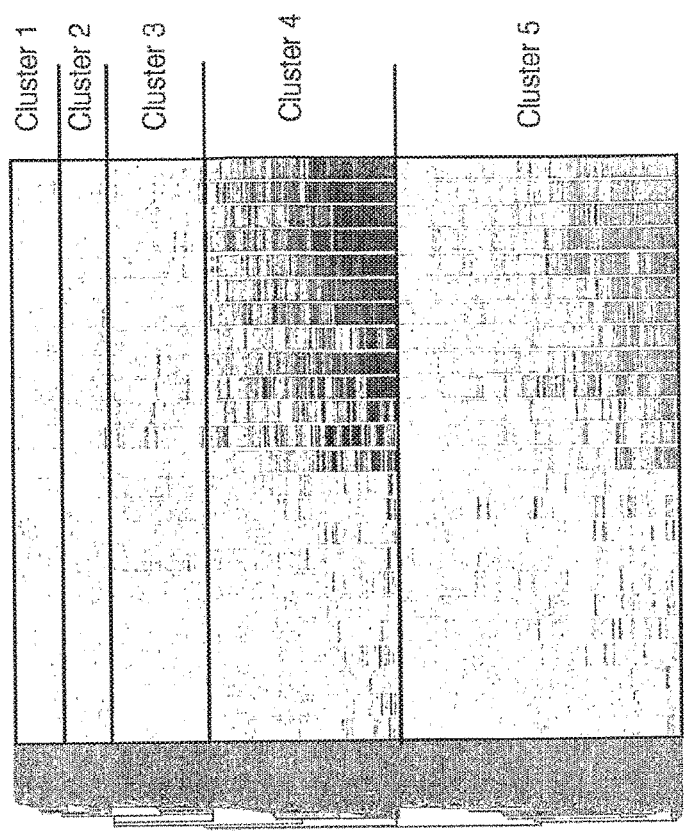
FIGS. 1A and 1B show the hierarchical cluster analysis of the transcripts expressed in normal (NL), chronic esophagitis (CE), and eosinophilic esophagitis (EE) esophageal biopsies. RNA from each patient was subjected to chip analysis using Affymetrix Human Genome U133 GeneChip plus 2. The NL group was composed of six individuals (1 to 6), the CE group was composed of five individuals (7 to 11), and the EE group was composed of 13 individuals (12 to 24) (Table 2). 574 genes significantly expressed differently ($p<0.01$) in EE compared to NL groups (Table 1). 574 genes significantly expressed differently ($p<0.01$) in EE compared to NL groups, and 228 genes significantly expressed differently ($p<0.01$) in CE compared to NL group. The data were analyzed by cluster analysis and ordered (standard correlation (A) and distance (B)) using Genespring software. Cluster 1, 2 and 3 highlight the CE transcripts and cluster 4 and 5 highlight the EE transcripts. The down regulated genes were depicted in blue and up-regulated genes were in red. The magnitude of the gene change was proportional to the darkness of the color. Each column represented a separate individual and each line a gene.

Individual characteristics are provided in Table 2. None of the patients were taking glucocorticoids (topical or oral) at the time of the endoscopy. Patient biopsies, collected from the distal esophagus during routine endoscopy following informed consent, were submerged in formalin for routine pathological analysis with hematoxylin and eosin staining. Diagnosis was established based on the maximum eosinophil count per high power field (hpf) and basal layer expansion according to established criteria. (eg. Rothenberg et al., 2001, Pathogenesis and clinical features of eosinophilic esophagitis. *J Allergy Clin Immunol* 108:891; Attwood et al., 1993, Esophageal eosinophilia with dysphagia. A distinct clinicopathologic syndrome. *Dig Dis Sci* 38:109; Fox et al., 2002, Eosinophilic esophagitis: its not just kid's stuff. *Gastrointest Endosc* 56:26, each of which is expressly incorporated by reference herein in its entirety. Normal individuals (NL) served as a control and were defined as having 0 eosinophils/hpf and no basal layer expansion. Individuals with chronic esophagitis (CE) were defined as having mild expansion of the basal layer (about <⅓ of epithelium) and/or ≤23 eosinophils/hpf. Individuals with eosinophilic esophagitis (EE) were defined by >24 eosinophils/hpf and extensive basal layer hyperplasia (expansion to about >⅓ of epithelium).

To assess allergen sensitization, skin prick testing was performed to a panel of 11 aeroallergens and 63 food antigens and assessed based on a 0-4 scale by comparison to the histamine control response. The total number of positive reactions to allergens (food allergen and aeroallergen) were counted and re-scored on a 0-4 scale. A score of 0-3 corresponded to 0, 1, 2, and 3 positive prick reactions, respectively; a score of 4 corresponded to ≥4 positive prick responses. Patients with a score of 1 were considered atopic.

For DNA microarray analysis, for each patient, one distal biopsy sample was emerged in RNAlater RNA Stabilization reagent (Qiagen, Germany) and stored at 4° C. for <15 days. Total RNA was extracted using RNAeasy mini Kit (Qiagen) according to the manufacturer's recommendations. Hybridization to DNA microarrays was performed by the Gene Chip Core at Children's Hospital Medical Center, Cincinnati Ohio. In brief, after RNA extraction, RNA quality was first assessed using the Agilent bioanalyzer (Agilent Technologies, Palo Alto, Calif.) (verifying high quality spectophometric characteristics), converted to cDNA with Superscript and subsequently converted to biotinylated cRNA with Enzo high yield RNA transcript labeling. After hybridization to the genome wide human Affymetrix U133A plus 2.0 genechips, the microarrays were stained with streptavidin-phycoerythrin using a Fluidics Station (Affymetix). The microarrays were scanned with a Hewlett Packard GeneArray Scanner, and gene transcript levels were determined using algorithms in the Microarray Analysis Suite and GeneSpring software (Silicon Genetics, Redwood City Calif.).

Differentially expressed transcripts were subjected to gene ontology analysis using DAVID (database for annotation, visualization and integrated discovery) and EASE (expression analysis systematic explorer), which is a web-based client/server application that allowed users to access a relational database of functional annotation.

For in situ hybridization, esophageal biopsy samples were fixed in 4% paraformaldehyde/PBS and stored overnight at 4° C. and subsequently emerged in 30% sucrose before in situ hybridization was performed. In brief, eotaxin-3 cDNA was generated using the primers acctgagaagggcctgattt and gtaactctgggaggaaacaccctctcc and cloned into PCR2.2 vector (Invitrogen). The resulting plasmid was linearized by BamHI or XhoI digestion, and sense and antisense RNA probes, respectively, were generated by T7 and sp6 RNA polymerase (Riboprobe Gemini Core System II transcription kit; Invitrogen. The radiolabeled (α35SthioUTP) probes were hybridized and the slides were washed under high stringency conditions. The slides were washed at 65° C. for 30 min in 50% formamide/1× SSC (150 mM NaCl/15 mM sodium citrate)/10 mM DTT; rinsed three times in 500 mM NaCl/10 mM Tris·HCl, pH 7.5/5 mM EDTA; digested with RNase A for 30 min at 37° C.; and rinsed in fresh buffer. The high-stringency wash was repeated and then followed by two 15-min washes at room temperature, one in 1× SSC and one in 0.1×SSC/1 mM DTT. Autoradiography was performed for 2-4 weeks at 4° C. Hybridization specificity was established by using the eotaxin-3 sense riboprobe. Sections from NL, EE and CE individuals were hybridized and underwent autoradiography under identical conditions.

For real-time polymerase chain reaction (PCR) analysis, RNA samples (500 ng) were subjected to reverse transcription analysis using Bioscript reverse transcriptase (BioRad) according to manufacturers instructions. Eotaxin-1, -2 and -3 were quantified by real-time PCR using the LightCycler instrument and LightCycler FastStart. DNA master SYBR green I as a ready-to use reaction mix (Roche, Indianapolis, Ind.) according to manufacturer's instructions. Results were normalized to GAPDH amplified from the same cDNA mix time and expressed as fold induction compared to controls. cDNA were amplified using following primers: hEotaxin-3 (151 bp): aactccgaaacaattgtactcagctg and gtaactctgggag-gaaacaccctctcc; hEotaxin-2(251 bp): ccatagtaaccagccttc and caggttcttcatgtacctc; hEotaxin-1(425 bp):tgaagcttgggccagct-tctgtcccaacc and ggtcgactggagttggagatttttggtc; GAPDH(400 bp): tggaaatcccatcaccatct and gtcttctgggtggcagtgat.

Plasma from heparinized blood was extracted and eotaxin-3 in 100 µl of plasma was quantified using Quantikine kit CCL26 (R&D Systems, Minneapolis) according to manufacturer's instructions. Results were expressed as pg of eotaxin-3 per ml plasma. The detection of the ELISA was 7 pg/ml.

Buccal swab DNA was collected from EE individuals (n=96) and their immediate relatives and from non-EE individuals (n=177) following informed consent. DNA was isolated by alkaline extraction. SNP detection was accessed using LightCycler instrument (Roche, Indianapolis). Briefly, LightCycler melting curves analysis was based on discriminating the temperature-dependant hybridization of sequence-specific hybridization probes to single-stranded DNA. Primers were designed using commercial software (Roche) and PCR was performed using LightCyler FastStart DNA master Hybridization Probes (Roche) according to manufacturer's protocol using the eotaxin-3 specific primers: aaggaaaaaatgggtgca and tgaacaacctttattaaagtaactct. For eotaxin-3 SNP analysis, the anchor probe was labeled with LCred fluorophore linked to agccaagagcggggtcc. The sensor probe (gcgtcctcggatgacaattca) was labeled with a second fluorophore (fluorescein) and designed to span the G/T mutation. Primers were designed using Primer Design Software (Roche).

BALB/c mice (National Cancer Institute, Frederick Md.) and CCR3-deficient mice (BALB/c background; a gift of Drs. Alison Humbles and Craig Gerard, Harvard Medical School) were housed under specific pathogen-free conditions. Experimental EE was induced by exposing mice to *Aspergillus fumigatus* antigen intranasally three times a week for 3 weeks. Mice were sacrificed 48 h following the last challenge, and the esophagus was harvested and fixed in formalin. Eosinophil levels were determined by immunostaining for mouse eosinophil major basic protein (anti-MBP), as disclosed in Mishra et al., 2001, An etiological role for aeroallergens and eosinophils in experimental esophagitis. *J Clin Invest* 107:83, which is expressly incorporated by reference herein in its entirety. Briefly, endogenous peroxidases in the tissues were quenched with 0.3% hydrogen peroxide in methanol followed by pepsin digestion for 5 min and by nonspecific protein blocking with normal goat serum for 30 min at room temperature. Tissue sections were then incubated with rabbit anti-MBP (a gift of Dr. James Lee, Mayo Clinic, Scottsdale Ariz.) (1:10,000) for 1 h at 4° C., followed by a 1:1000 dilution of biotinylated goat anti-rabbit IgG secondary antibody for 30 min at room temperature. Negative controls were assessed by replacing the primary antibody with normal rabbit serum to check endogenous biotin and peroxidase activity. Then avidin-peroxidase complex (Vector Laboratories, Burlingame Calif.) was used for 30 minutes. Immunoreactive cells quantification was carried out by a video-assistant integrated computer software program (Image Pro Plus 4.1; Media Cytometrics, Silver Spring Md.). Eosinophil levels were expressed as cells/mm².

Genes listed on microarray were obtained by studying differences in genes expression level between groups using Welch T-Test and Student T test (with or without false rate discovery (FDR) correction). EE transcripts were obtained using Welch T test with FDR (p≤0.01). CE transcript signature was composed of the addition of the gene lists from Welch T test without FDR and genes from Student T-test without FDR (p≤0.01). Ordered tree clustering was performed using standard correlation and distance. Correlation of gene expression with numeric clinical parameters or eosinophil levels was assessed using Pearson Correlation Test with p value. Tests used to generate the gene lists and number of genes in these lists are shown in Table 5. These lists were filtered based on p value and/or fold changes. Statistical significance between two groups of data was determined using T test or ANOVA, and correlations of data with number of eosinophils in the biopsies were determined using Pearson Correlation Test with p value.

The association between the SNP 2497T >G and EE susceptibility was first examined by family-based transmission disequilibrium test (TDT) to determine whether the affected child received the disease-associated allele more frequently than the alternative allele. The software TDT/S-

TDT 1.1 was used for analysis. Next, a case-control comparison was conducted at both genotype and allele frequency levels, where the cases are from the proband of each family, a set of race/ethnicity matched unrelated normal individuals were collected as controls. Statistical significance was evaluated by exact test using shuffling method, generated by 104 random permutations of the data. Hardy-Weinberg equilibrium test was also conducted in cases and controls, respectively. The software HWE was used to compute chi-square test for deviations from Hardy-Weinberg equilibrium.

EE transcript signatures were determined. Esophageal biopsy samples derived from individual patients were subjected to whole genome wide transcript expression profile analysis using oligonucleotide-based DNA microarray chips (Affymetrix Human Genome U133 GeneChip plus 2). Of the 54,681 transcripts represented on these microarrays, 574 transcripts (Table 1) were differently expressed (p<0.01) in the EE versus NL biopsy samples; thus, about 1% of the whole human genome transcripts defined the EE transcript signature, also referred to as the EE transcriptome, the complete collection of transcribed elements in the genome. For the EE and/or CE transcriptomes, this includes all transcribed elements related to these diseases. Besides mRNAs, it includes non-coding structural and regulatory RNAs. Alterations in the structure or expression levels of any one of these RNAs or translated proteins can contribute to pathogeneisis. Hierarchical clustering of the signal intensities of the individual transcripts in each group showed a high similarity of transcript expression patterns between EE patients (FIG. 1A). Of these, 344 transcripts were expressed more abundantly and 230 were expressed less abundantly in EE compared to NL individuals (FIG. 1A). Gene ontology analysis of the EE transcript signature (Table 3) revealed that the over-expressed genes were frequently involved in cell communication (25%), signal transduction (21%), response to external stimulus (20%), immune response (16%), and response to stress (11%). In contrast, the down-regulated genes were composed of a distinct family of functional groups (Table 4).

While there were numerous related families of dysregulated genes, five mast cell genes were highly induced, including carboxypeptidase A3, high affinity IgE receptor (FcLRI), and mast cell tryptase alpha (Table 9). Arachadonic acid metabolism genes were also represented; there were several dysregulated genes including the upregulated 15-lipoxygenase, prostaglandin D2 synthetase, leukotriene A4 hydrolase, and the down regulated 12-lipoxygenase, prostaglandin F synthase, leukotriene B4 12-hydroxydehydrogenase (Table 8). Regulators of cell growth and maintenance (periostin, fibroblast growth factor 11, Gro1 alpha) were over-represented (Tables 3 and 4).

Figure 1A:
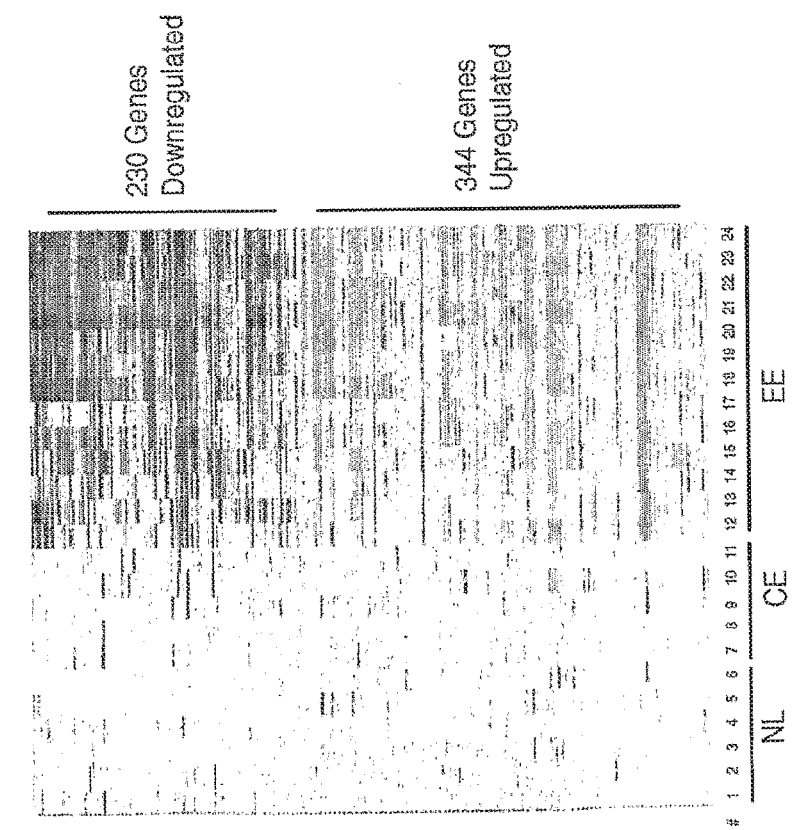

To further analyze the EE transcript signature, cluster analysis was performed to stratify dynamic genes into related subgroups (FIG. 1B). Clusters 4 and 5 represented downregulated and upreglated genes, respectively, compared with NL and CE individuals. Cluster analysis identified that CE also had a unique transcript signature compared with NL individuals; cluster 1 represented genes upregulated in CE compared to NL individuals.

Figure 2A:
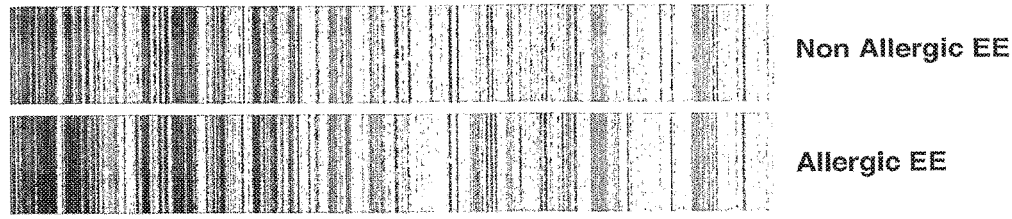
FIGS. 2A and 2B show the EE transcript signature as a function of the allergic status and gender of EE individuals. The 574 genes of the EE signature were subjected to cluster analysis and ordered (standard correlation) using Genespring software. Average expression of the transcripts of the EE signature was depicted in the non-allergic (n=4) and allergic EE (n=9) (A), and in the female (n=5) and male EE individuals (n=8) (B).
Figure 2B:
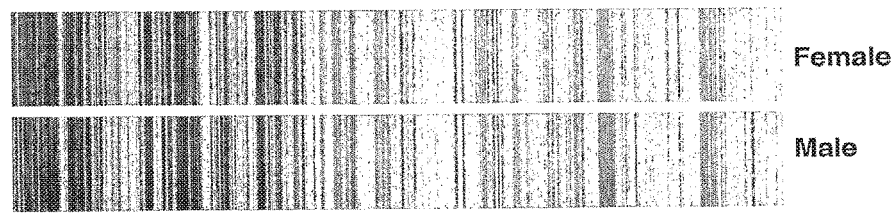

The identification of an EE transcript signature provided insight into disease pathogenesis. It was determined whether the allergic and non-allergic EE variants had different transcript profiles. When the full EE transcript profile was compared between allergic and non-allergic EE patients, there was near complete overlap in the transcripts (FIG. 2A) of the EE signature genome defined in Table 1. Only two genes were differently expressed (Lymphocyte Antigen 75 (2-fold increase in atopic) and Secreted Frizzled-related protein-1 (1.8-fold increase in non-atopic). The human LY75 molecule has previously been shown to have effect on IL-4 signaling. It was determined if EE patients had age dependent variable gene expression. Of the 574 dysregulated transcripts, no gene correlated with patient age within the EE transcript profile. As a control, outside of the EE transcript signature, there were 334 genes that correlated to patient age (Pearson correlation test with p<0.01). It was determined if the EE transcript profile was different between males and females. Only one gene (tyrosine kinase receptor B (3-fold increase in females) of the EE transcript signature depended upon gender (FIG. 2B). Outside of the EE transcript signature, there were 434 different genes between male and female EE. These results demonstrated that the EE transcript profile was conserved between individuals despite differences in gender, age, and atopic status.

Transcript expression profiles were compared in patients who presented with symptoms of EE but were found to have CE. Esophageal samples from CE patients contained only 216 dynamic transcripts (Table 5), about 0.4% of the tested genome, compared with NL (p<0.01). In FIG. 1B, the CE transcripts are seen in clusters 1, 2 and 3. These 216 transcripts (108 over expressed shown in combined clusters 1 and 2 and 108 down regulated in cluster 3) were rich in genes involved in intracellular cascades (10%) and biosynthesis (10%) (both in cluster 1) and cell growth and maintenance (22%) (in cluster 2). No transcript was modified by ≥5-fold in CE compared to NL (FIG. 3). In contrast, 124 genes were modified by ≥5-fold in EE compared with NL (FIG. 3), including 42 transcripts that were modified ≥10-fold in EE; the most dysregulated genes are shown in FIG. 3. To define genes that could distinguish EE and CE, EE and CE transcriptomes were directly compared. There was an overlap of only 40 genes between EE and CE (mainly in cluster 2) (FIG. 1B and Table 6) and only 5 of these overlapped with the EE transcript signature. All genes shared between EE and CE were modified by <2-fold compared to NL samples. Taken together, EE and CE did not appear to represent a continuum, but rather two distinct disease processes. Identification of strongly induced genes that distinguished EE from CE (FIG. 3) defined potential diagnostic criteria to distinguish these forms of esophagitis.

Figure 4B:
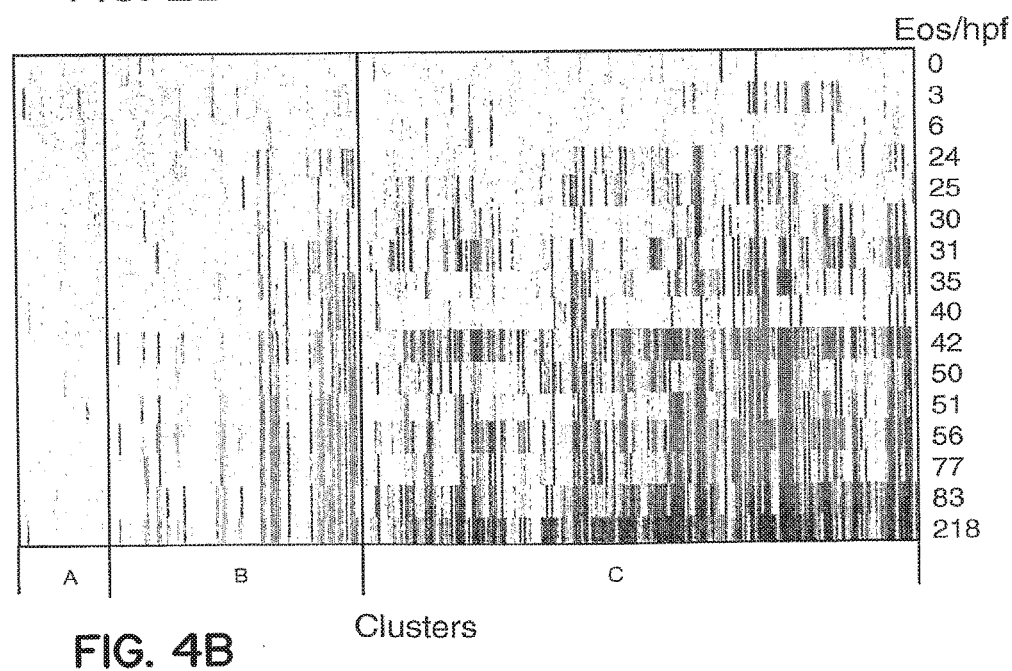
FIGS. 4A and 4B show the correlation between eosinophil count and number of genes modified. The numbers of genes expressed differently are presented as a function of eosinophil count (A). The number of genes that changed ≥5-fold (grey dot) or ≥10-fold (white dot) was plotted as a function of the maximum number of eosinophils in the biopsies. A trendline (black line) has been inserted to show the genes that change ≥10-fold. The histogram of the 1943 genes that most correlated (P≥50.005) to the number of eosinophils is presented (B). Cluster analysis based on standard correlation tree ordered identified 4 groups (cluster A, B, C and D). The genes upregulated were represented in red and the down-regulated genes were in blue. The magnitude of the gene changes was proportional to the darkness of the color.
Figure 4A:
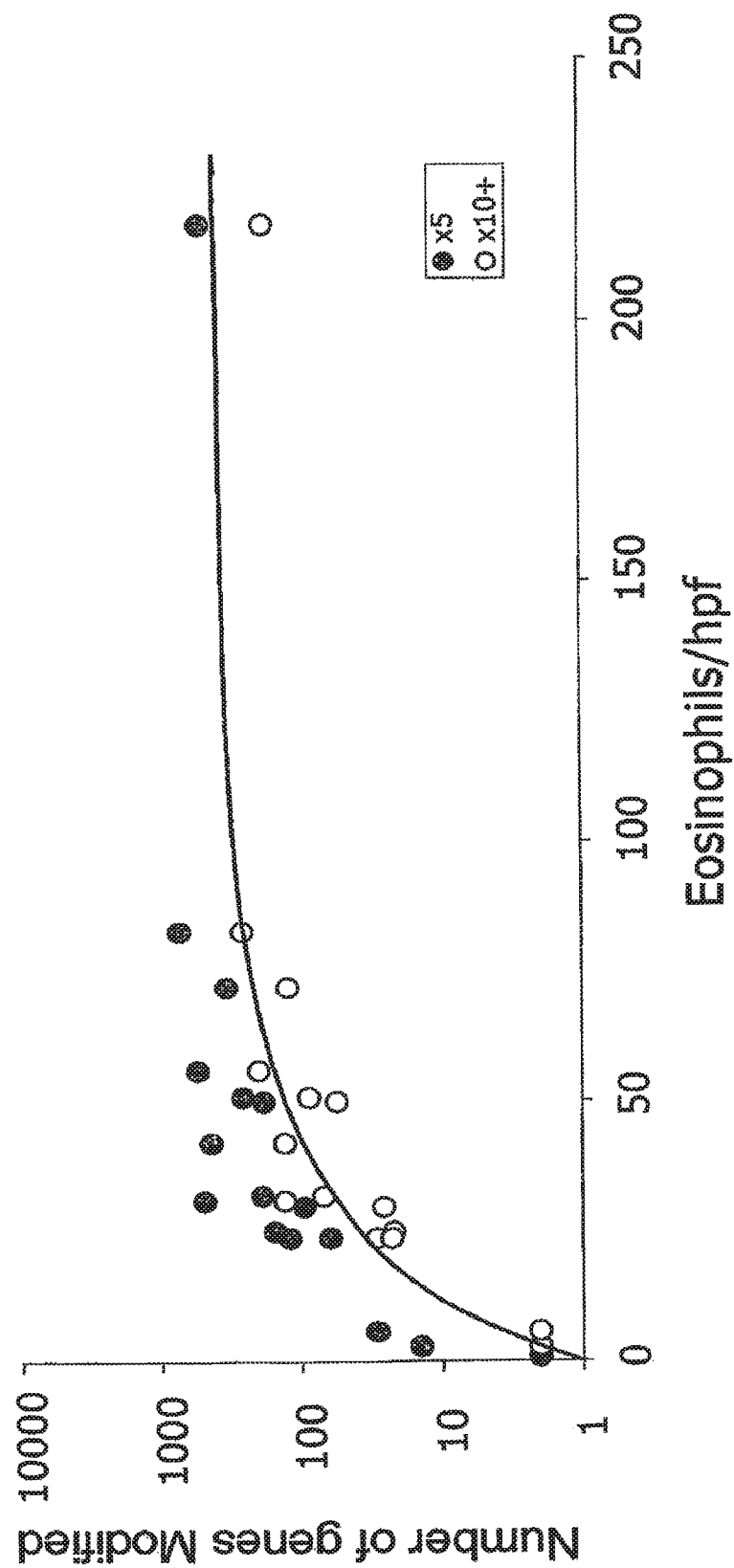
Figure 5A:
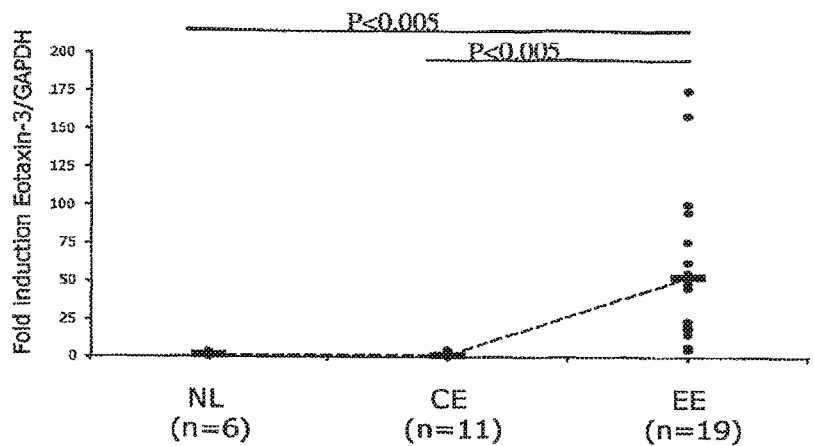
FIG. 5A-5C show the quantitative analysis of eotaxin-1, -2 and -3 mRNA levels in NL, CE and EE groups using real-time PCR analysis. The level of eotaxin-3 (A), eotaxin-1 (B) and eotaxin-2 (C) mRNA is shown. Each mRNA value was normalized to GAPDH mRNA and expressed as fold change. The black dash represented the average of fold change in each group. The P value was calculated using the ANOVA test. The number of individuals was 6, 11 and 19 for NL, CE and EE groups respectively.
Figure 5B:
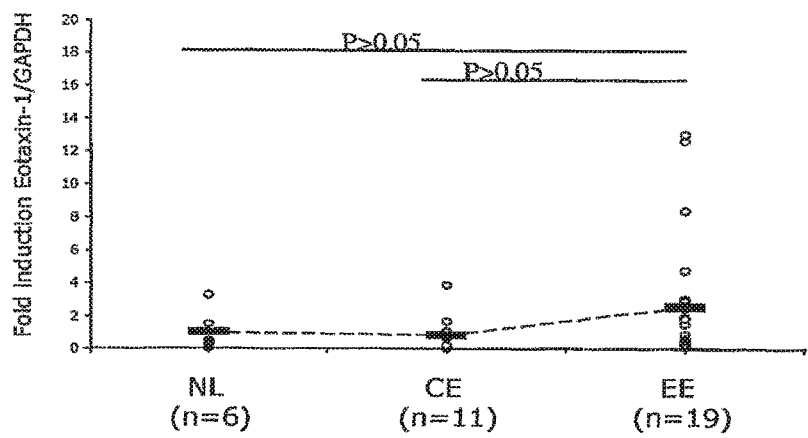
Figure 5C:
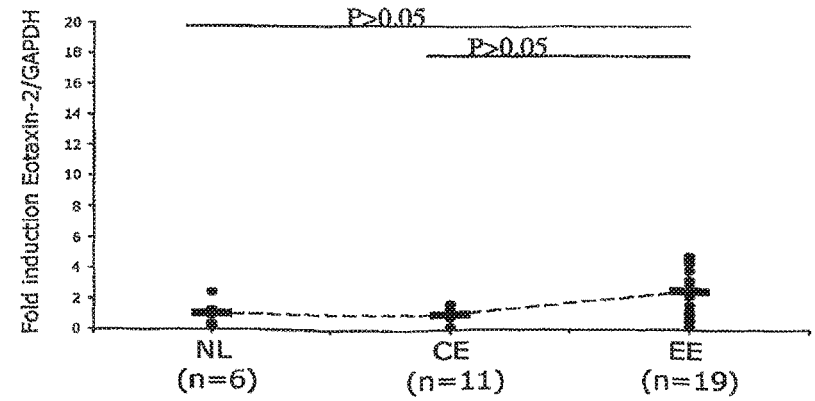
Figure 6:
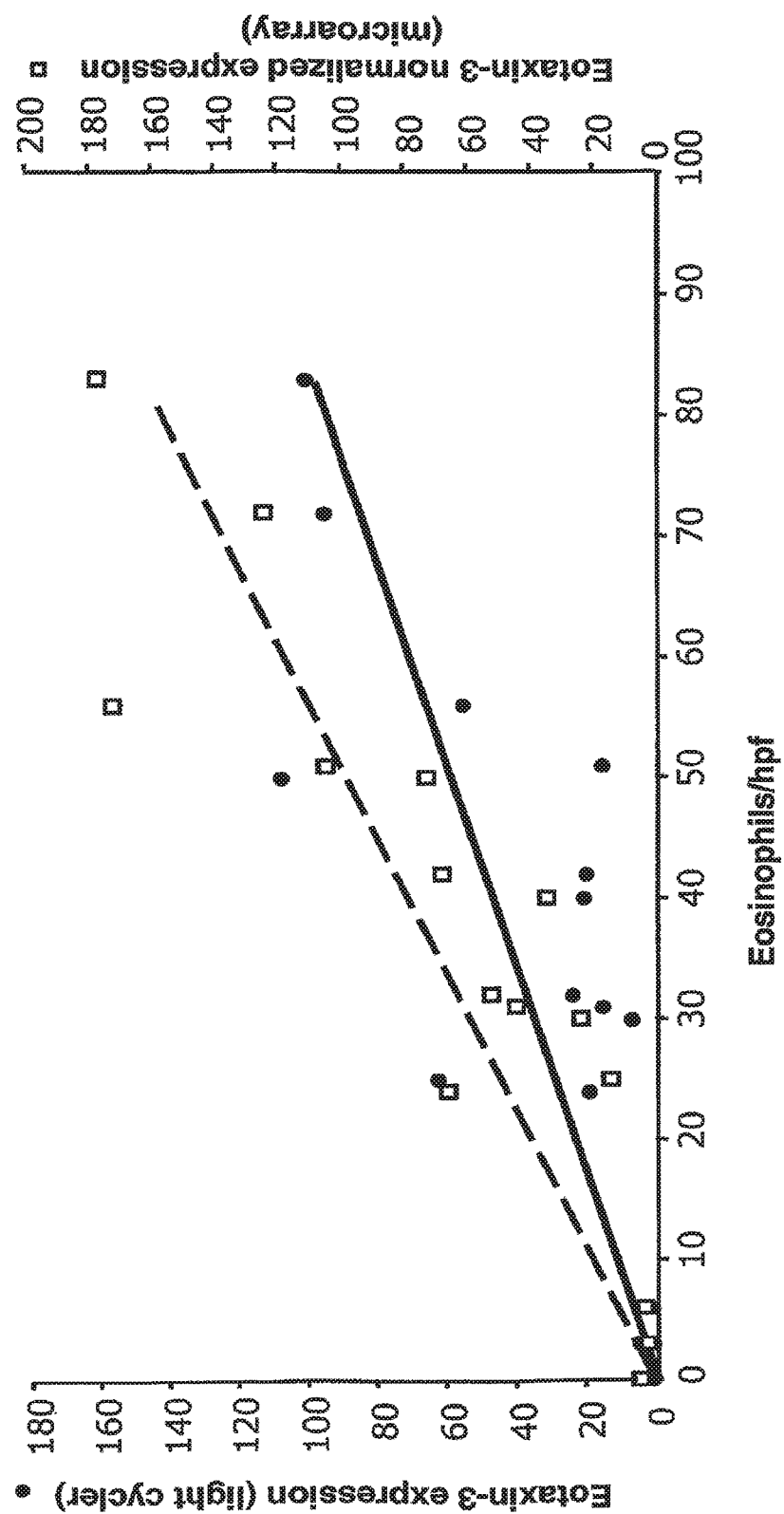
FIG. 6 shows the correlation between eotaxin-3 mRNA expression and esophageal eosinophil count. The eotaxin-3 expression measured using LightCycler (black dots and black line) and microarray analysis (open squares and dash line) was plotted as a function of the maximum eosinophil number (cells/hpf) present in the biopsies of NL, CE and EE individuals.

The EE transcriptome was analyzed as a function of disease severity, because that the number and magnitude of modified genes might be directly related to disease severity. Correlation of eosinophil levels with the number of altered genes was determined. Individuals with EE had eosinophil levels that varied between 24 to 218 eosinophils/hpf. The number of dysregulated genes increased between eosinophils levels of 0 and 56 and reached a plateau at eosinophil levels of 77 (FIGS. 1 & 4A). Similarly, the magnitude of genes changes (e.g. their degree of change) directly correlated with eosinophil levels (FIG. 4). The genes that most correlated (P<0.005) with eosinophil levels are presented in an ordered tree histogram and stratified into cluster A, B and C (FIG. 4B). Cluster B included genes that correlated with eosinophil level that were overexpressed in patients with ≥24 eosinophils/hpf and were frequently involved in cell communication (25%) and immune response (13%) functions. Cluster A contained genes that correlated with higher eosinophil levels ≥40 eosinophils/hpf). Cluster A was particularly rich in genes involved in cell growth and maintenance (24%). The mast cell gene signature was located in cluster B, which suggested that mast cells infiltration occurred as soon as 24 eosinophils/hpf were present in the esophagus. Within the EE transcript signature, the gene with greatest change was eotaxin-3, which was induced 53-fold. Other relevant eosinophil chemokines, such as eotaxin-1 and eotaxin-2, were induced <2-fold in EE samples. Using real time PCR analysis (Lightcycler), a mean 53-fold increase in eotaxin-3 mRNA compared with NL was observed (FIG. 5A). Modest changes in eotaxin-1 (FIG. 5B) and eotaxin-2 (FIG. 5C) were observed in EE patients, although there was some variability between patients. Elevated levels of eotaxin-2 and eotaxin-3 correlated with each other (P<0.05). Correlation between the level of eotaxin-3 and eosinophil levels in esophageal samples was determined. Two methods (Lightcycler quantification and microarray analysis) revealed a strong correlation between eotaxin-3 and eosinophil counts (P<0.01) (FIG. 6).

To localize eotaxin-3 production in the esophagus, in situ hybridization was performed on esophageal biopsies with eotaxin-3 sense and anti-sense cRNA probes. In EE patients, eotaxin-3 anti-sense probe strongly stained the epithelial cell layer (FIG. 7). Brightfield microscopy revealed that eotaxin-3 positive cells were confined to a population of mononuclear cells within the epithelial layer most consistent with epithelial cells. Infiltrative eosinophils were eotaxin-3 negative. Hybridization of eotaxin-3 anti-sense probes to NL and CE samples and the eotaxin-3 sense probe to EE samples revealed no significant staining (data not shown).

Figure 8:
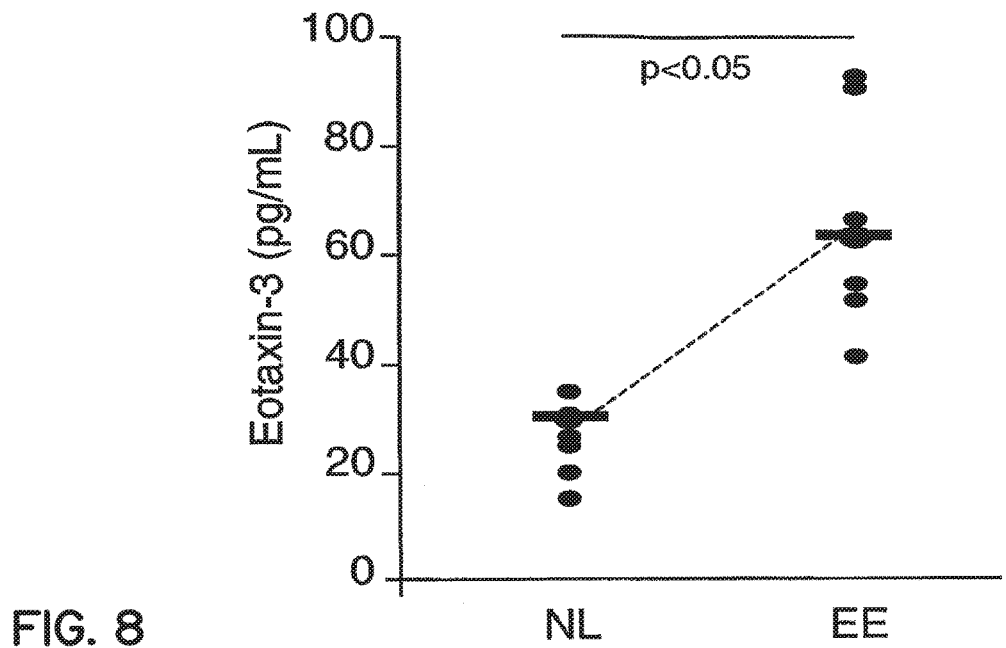
FIG. 8 shows blood eotaxin-3 protein levels. Eotaxin-3 level in plasma was assessed by ELISA. Each data point represented the eotaxin-3 level in one individual. The NL and EE groups are each composed of 9 individuals. P value was calculated using ANOVA.

To determine whether eotaxin-3 could be used as a non-invasive biomarker, eotaxin-3 protein level in the plasma was quantified in NL and EE patients. A 2-fold increase in eotaxin-3 protein levels was observed between NL and EE plasma samples (FIG. 8). Eotaxin-3 protein levels were 65±17 and 30±13 pg/ml in EE and NL plasma samples, respectively (P<0.002). No significant difference was observed in the eotaxin-3 level in the blood between allergic and non-allergic patients (64±19 and 61±26 pg/ml respectively).

Eotaxin-3 was implicated in the disease pathogenesis of EE, so that single nucleotide polymorphisms (SNP) in the eotaxin-3 gene might be associated with disease risk. The presence of eotaxin-3 +2496 (G/T) SNP in EE patients compared with control individuals was examined. The wild type allele is T having a frequency of 78.81% in control individuals. The G allele was over-represented in EE patients compared with NL (Table 7). The GG was strongly associated with EE (GG frequency was 13.54% and 2.26% in EE and NL, respectively). The relative risk of EE in patients with the GG allele was about 7-fold. In both EE and NL individuals, the G and T alleles were inherited based on Hardy-Weinberg equilibrium (Table 7).

Figure 9:
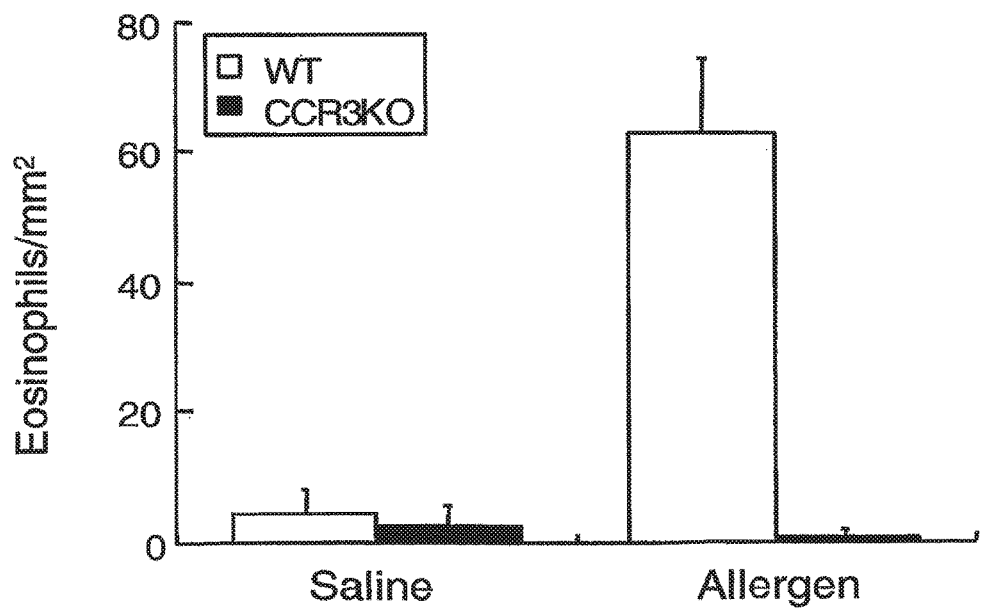
FIG. 9 shows the role of CCR3 in allergen-induced eosinophil recruitment to the esophagus of wild type (WT) and CCR3 deficient (knockout (KO)) mice. Mice were challenged with saline or *Aspergillus* intranasally three times a week for three weeks. The esophagus was harvested 24 h after the last intranasal treatment and esophageal sections were stained with anti-MBP. Results represent the number of eosinophils (mean±SD) (n=3) present in the esophagus per mm$^2$ of two representative experiments. *P<0.05 versus saline group, § P<0.05 versus WT group.

CCR3 gene target mice were protected from experimental EE. A murine system was used to evaluate the eotaxin pathway directly in vivo. An experimental model of EE had been developed, but an exact homolog of human eotaxin-3 had not yet been characterized in mice, therefore induction of experimental asthma in mice deficient in the eotaxin receptor CCR3 was examined. Cohorts of wild type and CCR3 deficient mice were exposed to repeated doses of intranasal allergen under conditions that induce experimental EE. In wild type mice, large numbers of eosinophils accumulated in the esophagus. While, CCR3 deficient mice were nearly completely protected from developing esophageal eosinophilia (FIG. 9).

The data reported above identified an EE transcript signature involving about 1% of the human genome. This transcriptome was conserved between individuals despite their age, gender, atopic status, and the patchiness of their disease. Despite the presence of apparent atopic and nonatopic EE variants of, the downstream effector phase of the disease was conserved between these disease variants rather than a large variability in gene transcript levels between patients due to their divergent clinical presentations (including age and gender). Thus, despite millions of SNPs in the human genome, EE and perhaps others polygenic disorders may have largely conserved disease mechanisms. The results are consistent with analysis of atopic and non-atopic variants of eosinophilic lung disease (asthma); while these only examined a limited set of cytokine mRNA levels, atopic and non-atopic patients had the same cytokine mRNA expression in lung tissue. The present data evidenced that atopic and non-atopic variants of eosinophilic disorders have a common underlying pathogenesis. A method of examining the etiology of atopic and disease variants is presented.

Eotaxin-3, which regulates eosinophil responses in vitro, was the top gene induced in EE. Levels of eotaxin-3 strongly correlated with disease severity and served as a disease biomarker. Mice with genetic deletion of the CCR3 eotaxin-3 receptor were protected from developing experimental EE. The specific overexpression of eotaxin-3, and not eotaxin-1 or eotaxin-2, was consistent with prior studies showing only modest protection from experimental EE in eotaxin-1 deficient mice, and the absence of eotaxin-1 overexpression in EE patients. Correlation of eotaxin-2 and -3 mRNA levels with each other was consistent with their common chromosomal location (7q11.23), suggesting co-regulation and co-involvement in EE. Eotaxin-2 and eotaxin-3 both contain Th2-associated STAT6 binding sites in their promoters. While all eotaxins bind to CCR3, they each have a different affinity for recombinant CCR3; EE patients may also have preferential responses to individual eotaxins. Without being bound by a specific theory, this may be due to specific SNPs in CCR3. A specific genetic variation in the eotaxin-3 gene was a strong risk factor for EE. While this SNP was in a non-coding region of the eotaxin-3 gene, it might be in linkage disequilibrium with a functional SNP; this SNP is 6 kp from SNP-4097 (rs7787623) in the promoter region, these two SNP appear to be in total linkage disequilibrium. The SNP+2496 has been associated with atopy in the Korean population. However, in the Caucasian population, this SNP was at a higher frequency (21% vs 5% allele frequency in Caucasians and Koreans, respectively). This genetic finding may be used alone or in combination with other markers, including eotaxin-3 protein levels, to establish non-invasive ways of assessing disease risk and/or phenotype.

CE also had its own unique transcript signature. The CE pathology was typical of GERD and was likely applicable to GERD. Identified transcript changes should be correlated with esophageal pH monitoring. GERD has not yet been analyzed by DNA microarray analysis. While there was a degree of overlap in CE and EE genes, there was a difference in the number of genes modified, the type of dysregulated genes, and the magnitude of the gene changes. Taken together, the data demonstrated that EE and CE were separate diseases, and were unlikely to represent a continuum of esophagitis. The results provide diagnostic criteria for distinguishing EE from other types of esophagitis. Levels of the genes listed in FIG. 3 may be disease determinants.

Mast cells were involved in EE based on the dominant mast cell gene signature in microarray analysis. Mast cell genes were upregulated when eosinophil levels were 24 eosinophils/hpf suggesting that mast cells correlated with eosinophils. Mast cells have been reported to be elevated in the esophagus of EE patients, although no assessment of their genetic content or phenotype was made. The finding of tryptase expression without chymase suggested the involvement of T cell dependent mucosal mast cells. Anti-mast cell therapy may be used for reducing, ameliorating, or treating EE.

Figure 10:
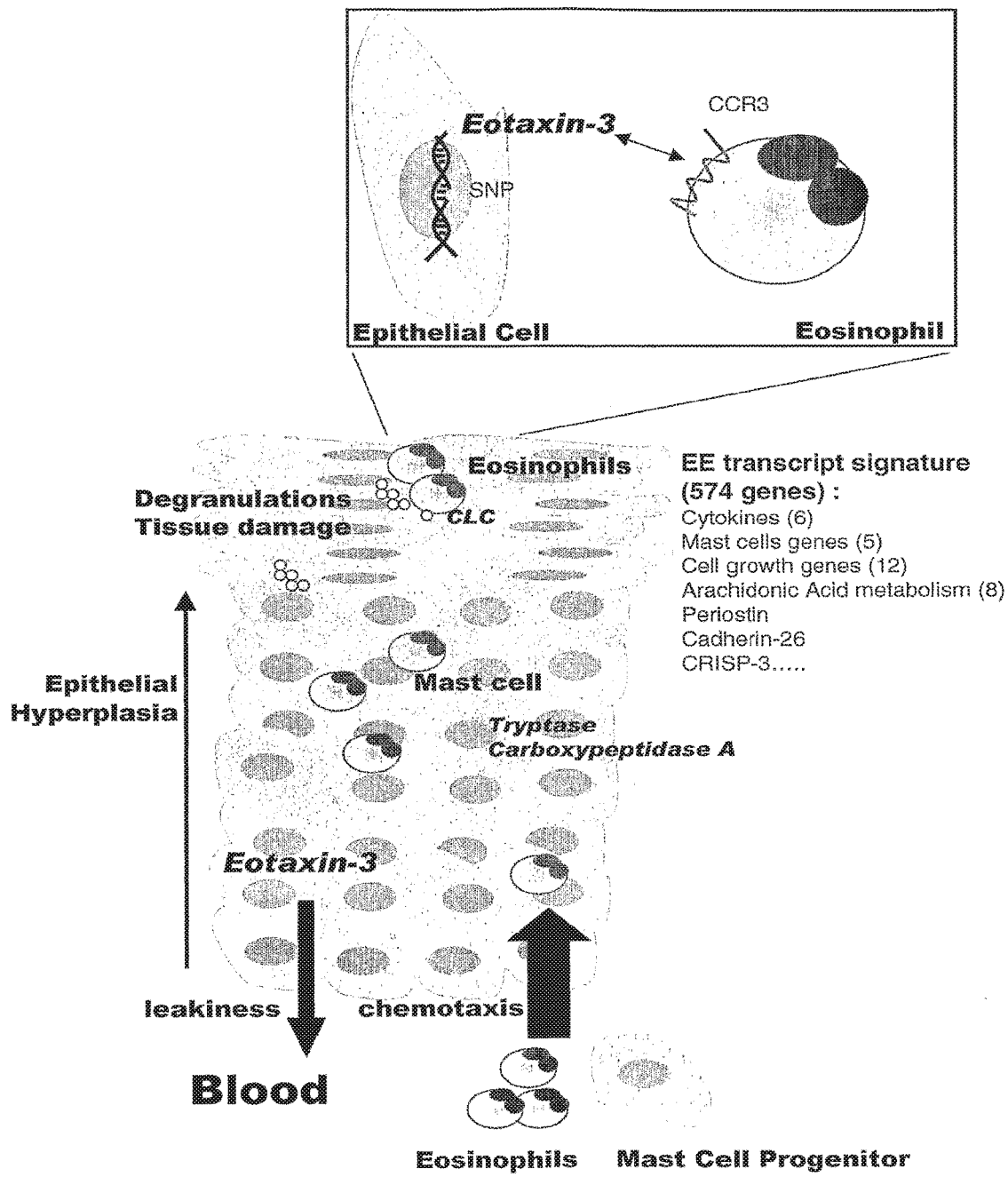
FIG. 10 shows a schematic representation of EE transcript signature in an EE esophageal biopsy. 574 genes defined the EE transcript signature, including cytokines, mast cell genes, arachidonic acid metabolism genes, and others. Without being limited to a specific mechanism, a proposed model to explain eotaxin-3-associated eosinophil recruitment in EE is shown. Hyperplasic epithelial cells of the esophagus overexpress eotaxin-3. Eotaxin-3 overexpression allows eosinophil chemoattraction of due to the CCR3 receptor. Eotaxin-3 protein leaks in the blood and may be used as a biomarker of EE. SNPs in eotaxin-3 may contribute to modify expression, or of the eotaxin-3 RNA or the affinity of eotaxin-3 protein for its receptor. Other SNPs (e.g., CCR3 receptor) may be involved. Mast cells are also recruited in the esophagus and mast cell genes (tryptase and carboxypeptidase) are overrepresented in the EE transcript signatures. Mast cells and eosinophils degranulations lead to tissue damage.

Few eosinophil-derived molecules were present in the EE transcript signature. For example, CCR3 and MBP were not in the EE transcript signature despite the eosinophil infiltration. This may be due to the dilution of eosinophil transcripts with transcripts from relative RNA-rich cells such as epithelial cells, fibroblasts and mast cells. However, Charcot Leyden Crystal (CLC) mRNA, an eosinophil specific transcript, was overexpressed in EE. CLC protein was initially reported to possess weak lysophospholipase activity. It showed no sequence similarities to any known lysophospholipases, but was a potent epithelial cell cytotoxin. CLC protein often crystallizes in the lung, yet such crystals have not yet been seen in EE. Other genes were involved in the EE transcript signature (FIG. 10). For example, periostin, a gene that is strongly over-expressed (47-fold) in EE patients, has been associated with epithelial cell growth, angiogenesis, and cellular adhesion. Cadherin-26 (overexpressed by 23-fold in EE patients) is a member of the cadherin family that has been associated with a variety of inflammatory and epithelial proliferation diseases. The most down-regulated gene, CRISP-3 (cysteine-rich secretory protein-3) is an androgen-dependent transcript, perhaps linking the male gender association with EE. In EE patient biopsies, there was a dysregulation in genes involved in arachadonic acid metabolism (e.g. upregulation of cyclooxygenase-2 and 15-lipoxygenase and downregulation of cyclooxgenase-1 and 12-lipoxygenase). Cox1 deficient mice developed increased levels of Th2 cytokines (IL-4, IL-13, and 5) and had higher recruitment of eosinophils following allergen challenge. In the gastrointestinal tract, cycloxygenase-2 had a role in epithelial cell growth.

Without being limited by a specific theory, EE may be an eotaxin-3 dominant disease involving a conserved genetic transcript signature (FIG. 10). The modulation of esophageal genes, compared with CE, supports that EE was a primary esophageal disease. Based on these results, eotaxin-3 and/or CCR3 blockers may be beneficial for the treatment of EE.

TABLE 1

EE Transcriptome

| Common Name | Description | Fold Change | Genbank Accession number | SEQ ID NO |
|---|---|---|---|---|
| CCL26 | \|\|MIP-4alpha\|\|CCL26\|\|TSC-1\|\|SCYA26, FORMERLY\|\|eotaxin-3 precursor\|\|EOTAXIN 3\|\|CC chemokine IMAC\|\|thymic stroma chemokine-1\|\|macrophage inflammatory protein 4-alpha\|\|small inducible cytokine A26\|\|CHEMOKINE, CC MOTIF, LIGAND 26\|\|chemokine (C-C motif) ligand 26\|\|SMALL INDUCIBLE CYTOKINE SUBFAMILY A, MEMBER 26, FORMERLY\|\|small inducible cytokine subfamily A (Cys-Cys), member 26\|\| | 53.17 | NM_006072 | 1 |
| POSTN | \|\|OSF-2\|\|POSTN\|\|PN\|\|periostin, osteoblast specific factor\|\|osteoblast specific factor 2 (fasciclin I-like)\|\| | 46.29 | NM_006475 | 2 |
| TNFAIP6 | \|\|TSG6\|\|TNFAIP6\|\|hyaluronate-binding protein\|\|tumor necrosis factor-stimulated gene-6 protein\|\|TUMOR NECROSIS FACTOR-ALPHA-INDUCED PROTEIN 6\|\|tumor necrosis factor-inducible protein 6\|\|tumor necrosis factor, alpha-induced protein 6\|\|tumor necrosis factor alpha-inducible protein 6\|\|tumor necrosis factor, alpha-induced protein 6 precursor\|\| | 23.59 | NM_007115 | 3 |
| CDH26 | \|\|CDH26\|\|cadherin-like 26\|\| | 23.42 | NM_177980 | 4 |
| CDH26 | \|\|CDH26\|\|cadherin-like 26\|\| | 21 | NM_177980 | 5 |
| ALOX15 | \|\|1.13.11.33\|\|ALOX15\|\|arachidonate 15-lipoxygenase\|\|15-@LIPOXYGENASE, RETICULOCYTE ARACHIDONATE\|\| | 20.89 | NM_001140 | 6 |
| PMCH | \|\|PMCH\|\|pro-melanin-concentrating hormone\|\| | 19.01 | NM_002674 | 7 |
| CXCL1 | \|\|MGSA-a\|\|NAP-3\|\|CXCL1\|\|SCYB1\|\|GROa\|\|GRO1, FORMERLY\|\|GRO PROTEIN, ALPHA\|\|GRO1 ONCOGENE, FORMERLY\|\|MELANOMA GROWTH STIMULATORY ACTIVITY, ALPHA\|\|GRO1 oncogene (melanoma growth-stimulating activity)\|\|CHEMOKINE, CXC MOTIF, LIGAND 1\|\|GRO1 oncogene (melanoma growth stimulating activity, alpha)\|\|SMALL INDUCIBLE | 18.79 | NM_001511 | 8 |

TABLE 1-continued

EE Transcriptome

| Common Name | Description | Fold Change | Genbank Accession number | SEQ ID NO |
|---|---|---|---|---|
| | CYTOKINE SUBFAMILY B, MEMBER 1\|\|chemokine (C-X-C motif) ligand 1 (melanoma growth stimulating activity, alpha)\|\| | | | |
| IGLV@ | \|\|IGLJ3\|\|immunoglobulin lambda joining 3\|\| | 17.57 | AK057174 | 9 |
| IGHD | \|\|IGHM\|\|immunoglobulin mu\|\|IMMUNOGLOBULIN HEAVY MU CHAIN\|\|immunoglobulin heavy constant mu\|\|constant region of heavy chain of IgM\|\| | 16.42 | AK090461 | 10 |
| FLJ16025 | FLJ16025 | 15 | XM_293626 | 11 |
| UBD | \|\|UBD\|\|FAT10\|\|diubiquitin\|\|ubiquitin D\|\| | 14.85 | NM_006398 | 12 |
| IGJ | \|\|IGCJ\|\|JCH\|\|IGJ\|\|immunoglobulin J chain\|\|immunoglobulin J polypeptide, linker protein for immunoglobulin alpha and mu polypeptides\|\| | 14.61 | NM_144646 | 13 |
| FLJ33069 | \|\|FLJ33069\|\|hypothetical protein FLJ33069\|\| | 14.01 | NM_144649 | 14 |
| CPA3 | \|\|CPA3\|\|3.4.17.1\|\|carboxypeptidase A3 (mast cell)\|\|CARBOXYPEPTIDASE A3, MAST CELL\|\|mast cell carboxypeptidase A3 precursor\|\| | 13.13 | NM_001870 | 15 |
| CLC | \|\|LPPL_HUMAN\|\|CLC\|\|galactin-10\|\|3.1.1.5\|\|LGALS10\|\|GALECTIN 10\|\|lysolecithin acylhydrolase\|\|eosinophil lysophospholipase\|\|LYSOPHOSPHOLIPASE OF EOSINOPHIL\|\|Charot-Leyden crystal protein\|\|Charcot-Leyden crystal protein\|\| | 12.69 | NM_001828 | 16 |
| TCF12; HEB; HTF4; HsT17266 | IGKC | 12.64 | BX647333 | 17 |
| IGL@ | IGL | 12.4 | NG_000002 | 18 |
| PHLDB2 | \|\|PHLDB2\|\|pleckstrin homology-like domain, family B, member 2\|\| | 12.05 | NM_145753 | 19 |
| POSTN | \|\|OSF-2\|\|POSTN\|\|PN\|\|periostin, osteoblast specific factor\|\|osteoblast specific factor 2 (fasciclin I-like)\|\| | 11.84 | NM_006475 | 20 |
| TCF12; HEB; HTF4; HsT17266 | IGKC | 10.97 | BX647333 | 21 |
| FLJ23259 | \|\|FLJ23259\|\|hypothetical protein FLJ23259\|\| | 10.94 | NM_024727 | 22 |
| TCF12; HEB; HTF4; HsT17266 | IGKC | 10.2 | BX647333 | 23 |
| EPPK1 | \|\|EPIPL1\|\|EPPK1\|\|epiplakin 1\|\|450 kDa epidermal antigen\|\| | 10.12 | NM_031308 | 24 |
| na | \|\|\|\|Hypothetical LOC148280 (LOC148280), mRNA\|\| | 9.701 | XM_097433 | 25 |
| SLC26A4 | \|\|SLC26A4\|\|pendrin\|\|PDS\|\|DFNB4\|\| solute carrier family 26, member 4\|\| | 9.548 | NM_000441 | 26 |
| EPPK1 | \|\|EPIPL1\|\|EPPK1\|\|epiplakin 1\|\|450 kDa epidermal antigen\|\| | 9.334 | NM_031308 | 27 |
| CTSC | \|\|HMS\|\|CPPI\|\|3.4.14.1\|\|DPPI\|\|PALS\|\| DPP1\|\|CTSC\|\|PLS\|\|dipeptidyl transferase\|\|cathepsin C\|\|dipeptidyl-peptidase I\|\|cathepsin J\|\|Papillon-Lefevre syndrome\|\|DIPEPTIDYL PEPTIDASE I\|\|cathepsin C isoform b precursor\|\|cathepsin C isoform a preproprotein\|\| | 9.008 | NM_001814 | 28 |
| SAMSN1 | \|\|HACS1\|\|SAMSN1\|\|HEMATOPOIETIC ADAPTOR CONTAINING SH3 AND SAM DOMAINS 1\|\|SAM domain, SH3 domain and nuclear localisation signals, 1\|\|SAM DOMAIN, SH3 DOMAIN, AND NUCLEAR LOCALIZATION SIGNALS 1\|\| | 8.687 | NM_022136 | 29 |
| TRPM6 | \|\|CHAK2\|\|TRPM6\|\|CHANNEL KINASE 2\|\|transient receptor potential cation channel, subfamily M, member 6\|\| | 8.519 | NM_017662 | 30 |

TABLE 1-continued

EE Transcriptome

| Common Name | Description | Fold Change | Genbank Accession number | SEQ ID NO |
|---|---|---|---|---|
| IGLV@ | IGL | 8.317 | AK057174 | 31 |
| SEC6L1 | ||||SEC6L1||SEC6-like 1 (*S. cerevisiae*)|| | 8.068 | NM_007277 | 32 |
| GPR160 | ||GPCR150||GPR160||putative G protein-coupled receptor||G protein-coupled receptor 160|| | 8.008 | NM_014373 | 33 |
| SUSD2 | ||SUSD2||sushi domain containing 2|| | 8.003 | NM_019601 | 34 |
| KIAA0495 | ||KIAA0495|| | 7.996 | AB007964 | 35 |
| NTRK2 | ||TRKB||NTRK2||TYROSINE KINASE RECEPTOR B||neurotrophic tyrosine kinase, receptor, type 2|| | 7.355 | NM_006180 | 36 |
| CTSC | ||HMS||CPPI||3.4.14.1||DPPI||PALS||DPP1||CTSC||PLS||dipeptidyl transferase||cathepsin C||dipeptidyl-peptidase I||cathepsin J||Papillon-Lefevre syndrome||DIPEPTIDYL PEPTIDASE I||cathepsin C isoform b precursor||cathepsin C isoform a preproprotein|| | 7.326 | NM_001814 | 37 |
| IGLV@ | ||IGLJ3||immunoglobulin lambda joining 3|| | 7.045 | AK057174 | 38 |
| OR2I6 | ||||Similar to Olfactory receptor 2I2 (LOC346170), mRNA|| | 6.874 | XM_294092 | 39 |
| KCNJ2 | ||HHBIRK1||HHIRK1||LQT7||KCNJ2||potassium inwardly-rectifying channel J2||inward rectifier K+ channel KIR2.1||cardiac inward rectifier potassium channel||inward rectifier potassium channel 2||potassium inwardly-rectifying channel, subfamily J, member 2||POTASSIUM CHANNEL, INWARDLY RECTIFYING, SUBFAMILY J, MEMBER 2|| | 6.696 | NM_000891 | 40 |
| NTRK2 | ||TRKB||NTRK2||TYROSINE KINASE RECEPTOR B||neurotrophic tyrosine kinase, receptor, type 2|| | 6.56 | NM_006180 | 41 |
| TPSB2 | ||||TPS1||tryptase, alpha|| | 6.429 | NM_003294 | 42 |
| CTSC | ||HMS||CPPI||3.4.14.1||DPPI||PALS||DPP1||CTSC||PLS||dipeptidyl transferase||cathepsin C||dipeptidyl-peptidase I||cathepsin J||Papillon-Lefevre syndrome||DIPEPTIDYL PEPTIDASE I||cathepsin C isoform b precursor||cathepsin C isoform a preproprotein|| | 6.299 | NM_001814 | 43 |
| IFRG28 | ||IFRG28||28 kD interferon responsive protein|| | 6.278 | NM_022147 | 44 |
| HRH1 | ||HRH1||H1-R||hisH1||histamine receptor H1||BPHS, MOUSE, HOMOLOG OF||histamine receptor, subclass H1|| | 6.191 | NM_000861 | 45 |
| SCUBE2 | ||SCUBE2||signal peptide, CUB domain, EGF-like 2|| | 6.166 | NM_020974 | 46 |
| IGKC | ||Km||HCAK1||IGKC||Immunoglobulin kappa constant||IMMUNOGLOBULIN InV KAPPA-CHAIN DEFICIENCY||IMMUNOGLOBULIN KAPPA LIGHT CHAIN||immunoglobulin kappa constant region||kappa 1 immunoglobulin light chain||Ig kappa chain C region|| | 6.073 | BM993907 | 47 |
| TPSB2 | ||||TPS1||tryptase, alpha|| | 6.028 | NM_003294 | 48 |
| CHL1 | ||L1CAM2||CHL1||CALL||neural cell adhesion molecule||cell adhesion molecule L1-like||CHL1, MOUSE, HOMOLOG OF||L1 cell adhesion molecule 2||cell adhesion molecule with homology to L1CAM precursor||cell adhesion molecule with homology to L1CAM (close homolog of L1)|| | 5.928 | NM_006614 | 49 |

TABLE 1-continued

EE Transcriptome

| Common Name | Description | Fold Change | Genbank Accession number | SEQ ID NO |
|---|---|---|---|---|
| IF | \|\|3.4.21.45\|\|IF\|\|FACTOR I\|\|FACTOR 'EYE'\|\|COMPLEMENT COMPONENT I\|\|I factor (complement)\|\|C3 INACTIVATOR, DEFICIENCY OF\|\|C3b INACTIVATOR COMPLEMENT COMPONENT 3 INACTIVATOR, DEFICIENCY OF\|\| | 5.687 | NM_000204 | 50 |
| GLDC | \|\|GLDC\|\|HYGN1\|\|GCSP\|\|GCE\|\|NKH\|\|1.4.4.2\|\|GLYCINE CLEAVAGE SYSTEM P PROTEIN\|\|glycine dehydrogenase (decarboxylating; glycine decarboxylase, glycine cleavage system protein P)\|\| | 5.608 | NM_000170 | 51 |
| SEC6L1 | \|\|\|\|SEC6L1\|\|SEC6-like 1 (*S. cerevisiae*)\|\| | 5.608 | NM_007277 | 52 |
| TPSB2 | \|\|\|\|TPS1\|\|tryptase, alpha\|\| | 5.573 | NM_003294 | 53 |
| PKP2 | \|\|PKP2\|\|plakophilin 2\|\| | 5.342 | NM_004572 | 54 |
| PGDS | \|\|PGDS\|\|5.3.99.2\|\|prostaglandin-D synthase\|\|prostaglandin D2 synthase, hematopoietic\|\|hematopoietic prostaglandin D2 synthase\|\| | 5.265 | NM_014485 | 55 |
| TFPI | \|\|LACI\|\|TFPI\|\|EPI\|\|EXTRINSIC PATHWAY INHIBITOR\|\|tissue factor pathway inhibitor (lipoprotein-associated coagulation inhibitor)\|\| | 5.108 | NM_006287 | 56 |
|  | \|\|*Homo sapiens* transcribed sequence with weak similarity to protein NP_060312.1 | 5.094 | BQ004901 | 57 |
| BF | \|\|GBG\|\|BF\|\|CFAB\|\|PBF2\|\|3.4.21.47\|\|C3 proaccelerator\|\|glycine-rich beta-glycoprotein\|\|B-factor, properdin\|\|C3/C5 convertase\|\|C3 proactivator\|\|PROPERDIN FACTOR B\|\|FACTOR B, PROPERDIN\|\|complement factor B preproprotein\|\| | 5.073 | NM_001710 | 58 |
| TPK1 | \|\|HTPK1\|\|TPK1\|\|THIAMINE KINASE\|\|thiamine pyrophosphokinase\|\|thiamin pyrophosphokinase 1\|\|mouse thiamin pyrophosphokinase homolog\|\| | 5.033 | NM_022445 | 59 |
| SLC16A1 | \|\|SLC16A1\|\|MCT1\|\|monocarboxylate transporter 1\|\|solute carrier family 16, member 1\|\|SOLUTE CARRIER FAMILY 16 (MONOCARBOXYLIC ACID TRANSPORTER), MEMBER 1\|\|solute carrier family 16 (monocarboxylic acid transporters), member 1\|\| | 4.941 | NM_003051 | 60 |
| PRRX1 | \|\|PMX1\|\|PRRX1\|\|PRX1\|\|homeobox protein PHOX1\|\|PAIRED-RELATED HOMEOBOX GENE 1\|\|paired related homeobox 1\|\|paired mesoderm homeo box 1\|\|paired mesoderm homeobox 1 isoform pmx-1a\|\|paired mesoderm homeobox 1 isoform pmx-1b\|\| | 4.819 | NM_006902 | 61 |
| CH25H | \|\|CH25H\|\|C25H\|\|cholesterol 25-hydroxylase\|\| | 4.732 | NM_003956 | 62 |
| LOC129607 | \|\|LOC129607\|\|hypothetical protein LOC129607\|\| | 4.61 | XM_059368 | 63 |
| LOC340061 | \|\|LOC340061\|\|hypothetical protein LOC340061\|\| | 4.603 | NM_198282 | 64 |
| IGKC | \|\|Km\|\|HCAK1\|\|IGKC\|\|Immunoglobulin kappa constant\|\|IMMUNOGLOBULIN InV KAPPA-CHAIN DEFICIENCY\|\|IMMUNOGLOBULIN KAPPA LIGHT | 4.578 | BM993907 | 65 |

TABLE 1-continued

EE Transcriptome

| Common Name | Description | Fold Change | Genbank Accession number | SEQ ID NO |
|---|---|---|---|---|
| | CHAIN\|\|immunoglobulin kappa constant region\|\|kappa 1 immunoglobulin light chain\|\|Ig kappa chain C region\|\| | 4.542 | CA314541 | 66 |
| FOXE1 | \|\|TTF-2\|\|FOXE1\|\|TITF2\|\|TTF2\|\|FKHL15\|\|forkhead (*Drosophila*)-like 15\|\|thyroid transcription factor-2\|\|Forkhead, *drosophila*, homolog-like 15\|\|forkhead box E1 (thyroid transcription factor 2)\|\| | 4.438 | NM_004473 | 67 |
| SYNPO | \|\|KIAA1029\|\|synaptopodin\|\|SYNPO\|\| | 4.415 | NM_007286 | 68 |
| ADRBK2 | \|\|GRK3\|\|BARK2\|\|2.7.1.126\|\|ADRBK2\|\| BETA-ADRENERGIC RECEPTOR KINASE 2\|\|adrenergic, beta, receptor kinase 2\|\|beta adrenergic receptor kinase 2\|\| | 4.385 | NM_005160 | 69 |
| SLC28A3 | \|\|SLC28A3\|\|CNT3\|\|CONCENTRATIVE NUCLEOSIDE TRANSPORTER 3\|\|solute carrier family 28 (sodium-coupled nucleoside transporter), member 3\|\| | 4.349 | NM_022127 | 70 |
| CYP7B1 | \|\|\|1.14.13.—\|\| CP7B\|\|CYP7B1\|\|oxysterol 7alpha-hydroxylase\|\|OXYSTEROL 7-ALPHA-HYDROXYLASE 1\|\|cytochrome P450, family 7, subfamily B, polypeptide 1\|\|cytochrome P450, subfamily VIIB (oxysterol 7 alpha-hydroxylase), polypeptide 1\|\| | 4.323 | NM_004820 | 71 |
| APOL1 | \|\|APOL1\|\|APO-L\|\|APOL-I\|\|apolipoprotein L-I\|\|apolipoprotein L, 1\|\|apolipoprotein L1 isoform b precursor\|\|apolipoprotein L1 isoform a precursor\|\| | 4.259 | NM_145343 | 72 |
| MSLN | \|\|CAK1\|\|SMR\|\|MSLN\|\|mesothelin\|\|MEGA-KARYOCYTE-POTENTIATING FACTOR\|\|SOLUBLE MPF/MESOTHELIN-RELATED PROTEIN\|\|mesothelin isoform 2 precursor\|\|mesothelin isoform 1 precursor\|\|megakaryocyte potentiating factor precursor\|\|ANTIGEN RECOGNIZED BY MONOCLONAL ANTIBODY K1\|\| | 4.254 | NM_013404 | 73 |
| SFRP1 | \|\|SFRP1\|\|FRP-1\|\|FrzA\|\|SARP2\|\|secreted apoptosis-related protein 2\|\|secreted frizzled-related protein 1\|\| | 4.239 | NM_003012 | 74 |
| GRK5 | \|\|2.7.1.—\|\|GRK5\|\|GPRK5\|\|G protein-coupled receptor kinase 5\|\| | 4.212 | NM_005308 | 75 |
| MS4A2 | \|\|FCERI\|\|MS4A1\|\|MS4A2\|\|FCER1B\|\| Fc epsilon receptor I beta-chain\|\|Fc IgE RECEPTOR, BETA CHAIN\|\|MEMBRANE-SPANNING 4 DOMAINS, SUBFAMILY A, MEMBER 2\|\|immunoglobulin E receptor, high affinity, beta polypeptide\|\|Fc FRAGMENT OF IgE, HIGH AFFINITY I, RECEPTOR FOR, BETA SUBUNIT\|\|membrane-spanning 4-domains, subfamily A, member 2 (Fc fragment of IgE, high affinity I, receptor for; beta polypeptide)\|\| | 4.192 | NM_000139 | 76 |
| PGBD5 | \|\|PGBD5\|\|piggyBac transposable element derived 5\|\| | 4.133 | NM_024554 | 77 |

TABLE 1-continued

EE Transcriptome

| Common Name | Description | Fold Change | Genbank Accession number | SEQ ID NO |
|---|---|---|---|---|
| GALNT4 | \|\|\|\|TUWD12\|\| | 4.097 | NM_003774 | 78 |
| HAS3 | \|\|\|\|HAS3\|\|hyaluronan synthase 3\|\| | 4.096 | NM_005329 | 79 |
| CXCR4 | CXCR4 | 4.092 | AJ224869 | 80 |
| CDH3 | \|\|CDHP\|\|HJMD\|\|PCAD\|\|CDH3\|\|placental cadherin\|\|CADHERIN, PLACENTAL\|\|cadherin 3, P-cadherin (placental)\|\|calcium-dependent adhesion protein, placental\|\|cadherin 3, type 1 preproprotein\|\|cadherin 3, type 1, P-cadherin (placental)\|\| | 4.065 | NM_001793 | 81 |
| TPSB2 | \|\|\|\|TPS1\|\|tryptase, alpha\|\| | 4.033 | NM_003294 | 82 |
| TPSB2 | \|\|\|\|TPS1\|\|tryptase, alpha\|\| | 3.98 | NM_003294 | 83 |
|  |  | 3.944 | BM988338 | 84 |
| KITLG |  | 3.939 | AK055903 | 85 |
| FETUB | \|\|FETUB\|\|Gugu\|\|16G2\|\|IRL685\|\|fetuin-like protein\|\|fetuin B\|\| | 3.894 | NM_014375 | 86 |
| SLC16A1 | \|\|SLC16A1\|\|MCT1\|\|monocarboxylate transporter 1\|\|solute carrier family 16, member 1\|\|SOLUTE CARRIER FAMILY 16 (MONOCARBOXYLIC ACID TRANSPORTER), MEMBER 1\|\|solute carrier family 16 (monocarboxylic acid transporters), member 1\|\| | 3.883 | NM_003051 | 87 |
| SGK | \|\|2.7.1.—\|\| SGK\|\|SGK1\|\|SERUM/GLUCOCORTICOID-REGULATED KINASE\|\|serum/glucocorticoid regulated kinase\|\|serine/threonine protein kinase SGK\|\| | 3.879 | NM_005627 | 88 |
| SIGLEC6 | \|\|SIGLEC6\|\|CD33L1\|\|SIGLEC-6\|\|OB-BINDING PROTEIN 1\|\|CD33 ANTIGEN-LIKE, MEMBRANE-BOUND\|\|CD33 antigen-like 1\|\|CD33 ANTIGEN-LIKE, SOLUBLE\|\|SIALIC ACID-BINDING IMMUNOGLOBULIN-LIKE LECTIN 6, SOLUBLE\|\|sialic acid binding Ig-like lectin 6\|\|OBBP1 SIALIC ACID-BINDING IMMUNOGLOBULIN-LIKE LECTIN 6, MEMBRANE-BOUND\|\|sialic acid binding Ig-like lectin 6 isoform b\|\|sialic acid binding Ig-like lectin 6 isoform a\|\|sialic acid binding Ig-like lectin 6 isoform c\|\| | 3.827 | NM_001245 | 89 |
| HTR2B | \|\|5-HT(2B)\|\|5-HT2B\|\|HTR2B\|\|SEROTONIN 5-HT-2B RECEPTOR\|\|5-@HYDROXYTRYPTAMINE RECEPTOR 2B\|\|5-hydroxytryptamine (serotonin) receptor 2B\|\| | 3.818 | NM_000867 | 90 |
| GPRC5B | \|\|RAIG2\|\|GPRC5B\|\|RETINOIC ACID-INDUCIBLE GENE 2\|\|G protein-coupled receptor, family C, group 5, member B\|\| | 3.762 | NM_016235 | 91 |
| CTSC | \|\|HMS\|\|CPPI\|\|3.4.14.1\|\|DPPI\|\|PALS\|\| DPP1\|\|CTSC\|\|PLS\|\|dipeptidyl transferase\|\|cathepsin C\|\|dipeptidyl-peptidase I\|\|cathepsin J\|\|Papillon-Lefevre syndrome\|\|DIPEPTIDYL PEPTIDASE I\|\|cathepsin C isoform b precursor\|\|cathepsin C isoform a preproprotein\|\| | 3.759 | NM_001814 | 92 |
|  |  | 3.721 | AW978130 | 93 |
| SERPINE2 | \|\|PN1\|\|GDN\|\|PNI\|\|SERPINE2\|\|PI7\|\| glial-derived nexin 1\|\|glial-derived neurite promoting factor\|\|protease inhibitor 7 (protease nexin I)\|\|plasminogen activator inhibitor type 1, member 2\|\|serine (or cysteine) proteinase inhibitor, clade | 3.69 | NM_006216 | 94 |

TABLE 1-continued

EE Transcriptome

| Common Name | Description | Fold Change | Genbank Accession number | SEQ ID NO |
|---|---|---|---|---|
| CTSG | E (nexin, plasminogen activator inhibitor type 1), member 2‖‖MGC23078‖CTSG‖3.4.21.20‖CG‖cathepsin G‖cathepsin G preproprotein‖ | 3.626 | NM_001911 | 95 |
| LITAF | ‖LITAF‖PIG7‖TP53I7‖FLJ38636‖CMT1C‖SIMPLE‖lipopolysaccharide-induced TNF factor‖LPS-induced TNF-alpha factor‖LIPOPOLYSACCHARIDE-INDUCED TUMOR NECROSIS FACTOR-ALPHA FACTOR‖tumor protein p53 inducible protein 7‖small integral membrane protein of lysosome/late endosome‖ | 3.601 | NM_004862 | 96 |
| SLC2A3 | ‖GLUT3P1‖SLC2A3P‖SLC2A3‖GLUCOSE TRANSPORTER 3 PSEUDOGENE 1‖GLUCOSE TRANSPORTER TYPE 3, BRAIN‖solute carrier family 2 (facilitated glucose transporter), member 3‖GLUCOSE TRANSPORTER, FETAL SKELETAL MUSCLE SOLUTE CARRIER FAMILY 2, MEMBER 3 PSEUDOGENE‖ | 3.549 | NM_006931 | 97 |
| IFI35 | ‖IFI35‖IFP35‖interferon-induced protein 35‖INTERFERON INDUCIBLE PROTEIN, 35-KD‖ | 3.545 | NM_005533 | 98 |
| TPK1 | ‖HTPK1‖TPK1‖THIAMINE KINASE‖thiamine pyrophosphokinase‖thiamin pyrophosphokinase 1‖mouse thiamin pyrophosphokinase homolog‖ | 3.491 | NM_022445 | 99 |
| MGC48998 | ‖MGC48998‖hypothetical protein MGC48998‖ | 3.481 | NM_178550 | 100 |
| ITGA9 | ‖ALPHA-RLC‖ITGA4L‖ITGA9‖INTEGRIN, ALPHA-9‖integin, alpha 9‖integrin, alpha 9‖integrin, alpha 4-like‖ALPHA RELATED TO THE DEVELOPMENT OF LUNG CANCER‖ | 3.453 | NM_002207 | 101 |
| IL17RB | ‖IL17RB‖IL17RH1‖IL17BR‖INTERLEUKIN 17B RECEPTOR‖interleukin 17 receptor B‖INTERLEUKIN 17 RECEPTOR HOMOLOG 1‖ | 3.446 | NM_172234 | 102 |
| PRG1 | ‖MGC2289‖PPG‖serglycin‖PRG1‖hematopoetic proteoglycan core peptide‖platelet proteoglycan protein core‖proteoglycan 1, secretory granule‖secretory granule proteoglycan core peptide‖proteoglycan 1, secretory granule precursor‖proteoglycan protein core for mast cell secretory granule‖ | 3.441 | NM_002727 | 103 |
| MRC1 | ‖MRC1‖mannose receptor precursor‖macrophage mannose receptor‖mannose receptor, C type 1‖mannose receptor C type 1 precursor‖ | 3.394 | NM_002438 | 104 |
| RARRES3 | ‖RIG1‖TIG3‖RARRES3‖TAZAROTENE-INDUCED GENE 3‖RETINOIC ACID RECEPTOR RESPONDER 3‖retinoic acid receptor responder (tazarotene induced) 3‖ | 3.38 | NM_004585 | 105 |
| DPYD | ‖1.3.1.2‖DPYD‖DIHYDROPYRIMIDINURIA‖dihydropyrimidine dehydrogenase‖PYRIMIDINEMIA, FAMILIAL‖5-@FLUOROURACIL TOXICITY‖DPD | 3.363 | NM_000110 | 106 |

TABLE 1-continued

EE Transcriptome

| Common Name | Description | Fold Change | Genbank Accession number | SEQ ID NO |
|---|---|---|---|---|
| MFHAS1 | DEFICIENCY\|\|DIHYDROPYRIMIDINE DEHYDROGENASE DEFICIENCY\|\|DHP THYMINE-URACILURIA, HEREDITARY\|\| \|\|MFHAS1\|\|MASL1\|\|MALIGNANT FIBROUS HISTIOCYTOMA-AMPLIFIED SEQUENCE 1\|\|malignant fibrous histiocytoma amplified sequence 1\|\|MFH-amplified sequences with leucine-rich tandem repeats 1\|\|MALIGNANT FIBROUS HISTIOCYTOMA-AMPLIFIED SEQUENCES WITH LEUCINE-RICH TANDEM REPEATS 1\|\| | 3.356 | NM_004225 | 107 |
| BCL2A1 | \|\|HBPA1\|\|BCL2A1\|\|BCL2L5\|\|GRS\|\|BCL2-RELATED GENE BFL1\|\|BCL2-related protein A1\|\|hematopoietic BCL2-related protein A1\|\| | 3.355 | NM_004049 | 108 |
| CFHL1 | \|\|\|\|HFL1\|\|H factor (complement)-like 1\|\| | 3.347 | NM_002113 | 109 |
| FGG | \|\|FGG\|\|fibrinogen, gamma polypeptide\|\|FIBRINOGEN--GAMMA POLYPEPTIDE CHAIN\|\|FIBRINOGEN, G GAMMA POLYPEPTIDE\|\|fibrinogen, gamma chain isoform gamma-B precursor\|\|fibrinogen, gamma chain isoform gamma-A precursor\|\| | 3.275 | NM_021870 | 110 |
| IL27RA | \|\|TCCR\|\|IL27RA\|\|CRL1\|\|WSX1\|\|zcytor1\|\| T-cell cytokine receptor\|\|class I cytokine receptor\|\|interleukin 27 receptor, alpha\|\| | 3.27 | NM_004843 | 111 |
| LOC130576 | \|\|LOC130576\|\|hypothetical protein LOC130576\|\| | 3.256 | NM_177964 | 112 |
| LHFPL2 | \|\|LHFPL2\|\|KIAA0206\|\|lipoma HMGIC fusion partner-like 2\|\| | 3.241 | NM_005779 | 113 |
| RGS2 | \|\|RGS2\|\|BASIC HELIX-LOOP-HELIX PHOSPHOPROTEIN G0S8\|\|REGULATOR OF G PROTEIN SIGNALING 2\|\|regulator of G-protein signalling 2, 24 kDa\|\|G0 to G1 switch regulatory 8, 24 kD\|\| | 3.237 | NM_002923 | 114 |
| ENO1 | \|\|4.2.1.11\|\|ENO1L1\|\|MPB1\|\|MBP-1\|\|tau-crystallin\|\|ENO1\|\|ENOLASE, ALPHA\|\|non-neural enolase\|\|2-phospho-D-glycerate hydrolyase\|\| ENOLASE, NONNEURONAL\|\|phosphopyruvate hydratase\|\|PPH CRYSTALLIN, TAU\|\|enolase 1, (alpha)\|\|MYC promoter-binding protein 1\|\| | 3.202 | NM_001428 | 115 |
| MFHAS1 | \|\|MFHAS1\|\|MASL1\|\|MALIGNANT FIBROUS HISTIOCYTOMA-AMPLIFIED SEQUENCE 1\|\|malignant fibrous histiocytoma amplified sequence 1\|\|MFH-amplified sequences with leucine-rich tandem repeats 1\|\|MALIGNANT FIBROUS HISTIOCYTOMA-AMPLIFIED SEQUENCES WITH LEUCINE-RICH TANDEM REPEATS 1\|\| | 3.193 | NM_004225 | 116 |
| TPSB2 | \|\|\|\|TPS1\|\|tryptase, alpha\|\| | 3.188 | NM_003294 | 117 |
| SH3RF2 | \|\|SH3RF2\|\|SH3 domain containing ring finger 2\|\| | 3.187 | NM_152550 | 118 |
| CISH | \|\|CIS-1\|\|SOCS\|\|G18\|\|CISH\|\|cytokine inducible SH2-containing protein\|\|suppressor of cytokine signaling\|\|cytokine-inducible SH2-containing protein isoform 1\|\|cytokine-inducible SH2-containing protein isoform 2\|\|cytokine-inducible inhibitor of signaling type 1B\|\| | 3.179 | NM_013324 | 119 |

TABLE 1-continued

EE Transcriptome

| Common Name | Description | Fold Change | Genbank Accession number | SEQ ID NO |
|---|---|---|---|---|
| COL8A2 | \|\|FECD\|\|PPCD2\|\|COL8A2\|\|FLJ00201\|\|COLLAGEN, TYPE VIII, ALPHA-2\|\|collagen VIII, alpha-2 polypeptide\|\|collagen, type VIII, alpha 2\|\| | 3.148 | NM_005202 | 120 |
| LBH | \|\|LBH\|\|likely ortholog of mouse limb-bud and heart gene\|\| | 3.147 | NM_030915 | 121 |
| SAMSN1 | \|\|HACS1\|\|SAMSN1\|\|HEMATOPOIETIC ADAPTOR CONTAINING SH3 AND SAM DOMAINS 1\|\|SAM domain, SH3 domain and nuclear localisation signals, 1\|\|SAM DOMAIN, SH3 DOMAIN, AND NUCLEAR LOCALIZATION SIGNALS 1\|\| | 3.147 | NM_022136 | 122 |
| SLC18A2 | \|\|VAT2\|\|SLC18A2\|\|SVAT\|\|VMAT2\|\|SVMT\|\|VESICULAR AMINE TRANSPORTER 2\|\|VESICULAR MONOAMINE TRANSPORTER 2\|\|SYNAPTIC VESICLE MONOAMINE TRANSPORTER, BRAIN\|\|SYNAPTIC VESICLE AMINE TRANSPORTER, BRAIN\|\|solute carrier family 18 (vesicular monoamine), member 2\|\|SOLUTE CARRIER FAMILY 18 (VESICULAR MONOAMINE TRANSPORTER), MEMBER 2\|\| | 3.144 | NM_003054 | 123 |
| F13A1 | \|\|FIBRINOLIGASE\|\|TGase\|\|F13A1\|\|2.3.2.13\|\|FIBRINASE DEFICIENCY\|\|FSF, A SUBUNIT\|\|FACTOR XIII, A1 SUBUNIT\|\|FIBRIN STABILIZING FACTOR, A SUBUNIT\|\|coagulation factor XIII, A1 polypeptide\|\|Coagulation factor XIII, A polypeptide\|\|coagulation factor XIII A1 subunit precursor\|\|TRANSGLUTAMINASE, PLASMA FACTOR XIII, A SUBUNIT, DEFICIENCY OF\|\| | 3.134 | NM_000129 | 124 |
|  |  | 3.131 | AK095590 | 125 |
| ACSL5 | \|\|ACSL5\|\|FACL5\|\|ACS5\|\|ACYL-CoA SYNTHETASE 5\|\|acyl-CoA synthetase long-chain family member 5\|\|FATTY ACID CoA LIGASE, LONG-CHAIN 5\|\| | 3.127 | NM_016234 | 126 |
| TNFSF13 | \|\|TWE-PRIL\|\|TALL2\|\|TNFSF13\|\|TNF-related death ligand-1\|\|proliferation inducing ligand APRIL\|\|tumor necrosis factor-related death ligand-1\|\|tumor necrosis factor (ligand) superfamily, member 13\|\|TNF- and APOL-related leukocyte expressed ligand 2\|\|tumor necrosis factor ligand superfamily, member 13 isoform delta\|\|tumor necrosis factor ligand superfamily, member 13 isoform gamma\|\|tumor necrosis factor ligand superfamily, member 13 isoform beta\|\|tumor necrosis factor ligand superfamily, member 13 isoform alpha precursor\|\| | 3.116 | NM_003808 | 127 |
| STOM | \|\|BND7\|\|STOM\|\|stomatin\|\|EPB72\|\|stomatin isoform a\|\|stomatin isoform b\|\|ERYTHROCYTE SURFACE PROTEIN BAND 7.2\|\|ERYTHROCYTE BAND 7 INTEGRAL MEMBRANE PROTEIN\|\|erythrocyte membrane protein band 7.2 (stomatin)\|\| | 3.104 | NM_004099 | 128 |
| HDC | \|\|HDC\|\|4.1.1.22\|\|histidine decarboxylase\|\| | 3.073 | NM_002112 | 129 |
| KIAA1126 | \|\|KIAA1126\|\|KIAA1126 protein\|\| | 3.071 | AB032952 | 130 |
| PSMB9 | \|\|3.4.25.1\|\|RING12\|\|LMP2\|\|PSMB9\|\|macropain chain 7\|\|proteasome-related gene 2\|\|proteasome chain | 3.019 | NM_002800 | 131 |

TABLE 1-continued

EE Transcriptome

| Common Name | Description | Fold Change | Genbank Accession number | SEQ ID NO |
|---|---|---|---|---|
| | 7\|\|PROTEASOME SUBUNIT, BETA-TYPE, 9\|\|proteasome subunit beta 6i\|\|proteasome catalytic subunit 1i\|\|low molecular mass protein 2\|\|proteasome subunit, beta type, 9\|\|multicatalytic endopeptidase complex chain 7\|\|proteasome beta 9 subunit isoform 1 proprotein\|\|proteasome beta 9 subunit isoform 2 proprotein\|\|proteasome (prosome, macropain) subunit, beta type, 9 (large multifunctional protease 2)\|\| | | | |
| LRRC5 | \|\|LRRC5\|\|leucine rich repeat containing 5\|\| | 3.014 | NM_018103 | 132 |
| GALNT5 | \|\|GALNT5\|\|UDP-N-acetyl-alpha-D-galactosamine:polypeptide N-acetylgalactosaminyltransferase 5 (GalNAc-T5)\|\| | 2.991 | NM_014568 | 133 |
| LOC340061 | \|\|LOC340061\|\|hypothetical protein LOC340061\|\| | 2.986 | NM_198282 | 134 |
| SCIN | \|\|scinderin\|\|SCIN\|\| | 2.985 | NM_033128 | 135 |
| LR8 | \|\|LR8\|\|LR8 protein\|\| | 2.941 | NM_014020 | 136 |
| LOC126917 | \|\|LOC126917\|\|hypothetical protein LOC126917\|\| | 2.94 | XM_375695 | 137 |
| HLF | \|\|HLF\|\|hepatic leukemia factor\|\|HLF HLF/E2A FUSION GENE\|\| | 2.932 | NM_002126 | 138 |
| TRIM22 | \|\|GPSTAF50\|\|RNF94\|\|TRIM22\|\|tripartite motif-containing 22\|\|tripartite motif protein TRIM22\|\|TRIPARTITE MOTIF-CONTAINING PROTEIN 22\|\|STIMULATED TRANS-ACTING FACTOR, 50-KD\|\|stimulated trans-acting factor (50 kDa)\|\| | 2.931 | NM_006074 | 139 |
| | | 2.93 | AW195474 | 140 |
| | | 2.919 | AA806368 | 141 |
| GCNT2 | \|\|GCNT5\|\|NAGCT1\|\|BIGnT\|\|ULG3\|\|bA360O19.2\|\|CIGnT\|\|bA421M1.1\|\|GCNT2\|\|NACGT1\|\|AIGnT\|\|2.4.1.150\|\|N-acetyllactosaminide beta-1,6-N-acetylglucosaminyltransferase\|\|BETA-1,6-N-ACETYLGLUCOSAMINYLTRANSFERASE 2\|\| beta-1,6-N-acetylglucosaminyltransferase\|\|blood group Ii\|\|Ii blood group\|\|DEVELOPMENTAL I ANTIGEN\|\|glucosaminyl (N-acetyl) transferase 5\|\|glucosaminyl (N-acetyl) transferase 2 isoform A\|\|glucosaminyl (N-acetyl) transferase 2 isoform B\|\|glucosaminyl (N-acetyl) transferase 2 isoform C\|\|glucosaminyl (N-acetyl) transferase 2, I-branching enzyme\|\| | 2.898 | NM_001491 | 142 |
| LILRB2 | \|\|\|\|LILRB2\|\|leukocyte immunoglobulin-like receptor, subfamily B (with TM and ITIM domains), member 2\|\| | 2.884 | NM_005874 | 143 |
| IL15 | \|\|\|IL-15\|\|IL15\|\|MGC9721\|\|interleukin 15\|\|interleukin 15 isoform 2 precursor\|\|interleukin 15 isoform 1 precursor\|\| | 2.879 | NM_172174 | 144 |
| NFE2L3 | \|\|NFE2L3\|\|NRF3\|\|NF-E2-related factor 3\|\|NFE2-RELATED FACTOR 3\|\|NUCLEAR FACTOR ERYTHROID 2-LIKE 3\|\|nuclear factor (erythroid-derived 2)-like 3\|\| | 2.867 | NM_004289 | 145 |
| SH3RF2 | \|\|SH3RF2\|\|SH3 domain containing ring finger 2\|\| | 2.826 | NM_152550 | 146 |

TABLE 1-continued

EE Transcriptome

| Common Name | Description | Fold Change | Genbank Accession number | SEQ ID NO |
|---|---|---|---|---|
| KIAA1145 | ||KIAA1145||KIAA1145 protein|| | 2.82 | NM_020698 | 147 |
| IL17RB | ||IL17RB||IL17RH1||IL17BR||INTERLEUKIN 17B RECEPTOR||interleukin 17 receptor B||INTERLEUKIN 17 RECEPTOR HOMOLOG 1|| | 2.819 | NM_172234 | 148 |
| GPR110 | ||GPR110||G protein-coupled receptor 110|| | 2.809 | NM_153840 | 149 |
| TFPI | ||LACI||TFPI||EPI||EXTRINSIC PATHWAY INHIBITOR||tissue factor pathway inhibitor (lipoprotein-associated coagulation inhibitor)|| | 2.808 | NM_006287 | 150 |
| TNFSF13 | ||TWE-PRIL||TALL2||TNFSF13||TNF-related death ligand-1||proliferation inducing ligand APRIL||tumor necrosis factor-related death ligand-1||tumor necrosis factor (ligand) superfamily, member 13||TNF- and APOL-related leukocyte expressed ligand 2||tumor necrosis factor ligand superfamily, member 13 isoform delta||tumor necrosis factor ligand superfamily, member 13 isoform gamma||tumor necrosis factor ligand superfamily, member 13 isoform beta||tumor necrosis factor ligand superfamily, member 13 isoform alpha precursor|| | 2.79 | NM_003808 | 151 |
| LOH11CR2A | ||BCSC-1||LOH11CR2A||loss of heterozygosity, 11, chromosomal region 2, gene A|| | 2.772 | NM_014622 | 152 |
| TPPP | ||p25||brain-specific protein p25 alpha||glycogen synthase kinase 3 (GSK3) inhibitor p24|| | 2.767 | NM_007030 | 153 |
| Cep72 | ||FLJ10565||hypothetical protein FLJ10565|| | 2.758 | NM_018140 | 154 |
| CISH | ||CIS-1||SOCS||G18||CISH||cytokine inducible SH2-containing protein||suppressor of cytokine signaling||cytokine-inducible SH2-containing protein isoform 1||cytokine-inducible SH2-containing protein isoform 2||cytokine-inducible inhibitor of signaling type 1B|| | 2.74 | NM_013324 | 155 |
| MGC35033 | ||MGC35033||hypothetical protein MGC35033|| | 2.739 | NM_152319 | 156 |
| CNTN4 | ||CNTN4||contactin 4||BIG2, RAT, HOMOLOG OF|| | 2.706 | NM_175607 | 157 |
| NFE2L3 | ||NFE2L3||NRF3||NF-E2-related factor 3||NFE2-RELATED FACTOR 3||NUCLEAR FACTOR ERYTHROID 2-LIKE 3||nuclear factor (erythroid-derived 2)-like 3|| | 2.682 | NM_004289 | 158 |
| CFH | ||FHL1||CFH||HF1||HUS||complement factor H||H factor-1 (complement)||H factor 1 (complement)||HF FACTOR H-LIKE 1||FACTOR H AND FACTOR H-LIKE 1, COMBINED DEFICIENCY OF|| | 2.673 | NM_000186 | 159 |
| PSMB8 | ||MGC1491||RING10||LMP7||D6S216E||PSMB8||3.4.25.1||large multifunctional protease-7||macropain subunit C13||proteasome subunit Y2||protease component C13||proteasome-related gene 7||PROTEASOME SUBUNIT, BETA-TYPE, 8||proteasome subunit beta 5i||proteasome catalytic subunit 3i||multicatalytic endopeptidase complex subunit C13||proteasome subunit, beta type, 8||low molecular weight protein 7||proteasome beta 8 | 2.65 | NM_004159 | 160 |

TABLE 1-continued

EE Transcriptome

| Common Name | Description | Fold Change | Genbank Accession number | SEQ ID NO |
|---|---|---|---|---|
| | subunit isoform E1 proprotein\|\|proteasome beta 8 subunit isoform E2 proprotein\|\|proteasome (prosome, macropain) subunit, beta type, 8 (large multifunctional protease 7)\|\| | | | |
| LOXL4 | \|\|LOXL4\|\|LOXC\|\|lysyl oxidase-like 4\|\| | 2.647 | NM_032211 | 161 |
| TRAF5 | \|\|RNF84\|\|MGC: 39780\|\|TRAF5\|\|TNF receptor-associated factor 5\|\| | 2.613 | NM_004619 | 162 |
| CLN6 | \|\|CLN6\|\|CLN6 GENE\|\|ceroid-lipofuscinosis, neuronal 6, late infantile, variant\|\| | 2.592 | NM_017882 | 163 |
| HLF | \|\|HLF\|\|hepatic leukemia factor\|\|HLF HLF/E2A FUSION GENE\|\| | 2.587 | NM_002126 | 164 |
| SCUBE1 | \|\|SCUBE1\|\|signal peptide, CUB domain, EGF-like 1\|\| | 2.577 | NM_173050 | 165 |
| CASP7 | \|\|MCH3\|\|CASP7\|\|CMH-1\|\|ICE-LAP3\|\|Lice2 alpha/beta/gamma\|\|apoptotic protease MCH-3\|\|ICE-like apoptotic protease 3\|\|caspase 7 isoform beta\|\|caspase 7 isoform alpha precursor\|\|caspase 7, apoptosis-related cysteine protease\|\|caspase 7 isoform alpha, large subunit\|\|caspase 7 isoform delta, large subunit\|\| | 2.573 | NM_033339 | 166 |
| CLDN23 | \|\|CLDN23\|\|claudin 23\|\| | 2.567 | NM_194284 | 167 |
| SH3RF2 | \|\|SH3RF2\|\|SH3 domain containing ring finger 2\|\| | 2.536 | NM_152550 | 168 |
| APOL3 | \|\|APOL3\|\|APOL-III\|\|APOLIPOPROTEIN L-III\|\|apolipoprotein L, 3\|\| | 2.535 | NM_145641 | 169 |
| SEPX1 | \|\|SEPX1\|\|SELR\|\|SELX\|\|SELENOPROTEIN R\|\|selenoprotein X, 1\|\| | 2.519 | NM_016332 | 170 |
| FA2H | \|\|FA2H\|\|fatty acid 2-hydroxylase\|\| | 2.516 | NM_024306 | 171 |
| NEK6 | \|\|NEK6\|\|SID6-1512\|\|NIMA-RELATED KINASE 6\|\|putative serine-threonine protein kinase\|\|NEVER IN MITOSIS GENE A-RELATED KINASE 6\|\|NIMA (never in mitosis gene a)-related kinase 6\|\| | 2.498 | NM_014397 | 172 |
| CLN6 | \|\|CLN6\|\|CLN6 GENE\|\|ceroid-lipofuscinosis, neuronal 6, late infantile, variant\|\| | 2.493 | NM_017882 | 173 |
| TM4SF8 | \|\|TM4SF8\|\|TSPAN-3 1700055K04Rik\|\|tetraspanin TM4-A\|\|tetraspan TM4SF\|\|tetraspanin 3\|\|tetraspan 3\|\|transmembrane 4 superfamily member 8\|\|transmembrane 4 superfamily, member 8\|\|transmembrane 4 superfamily member 8 isoform 2\|\|transmembrane 4 superfamily member 8 isoform 1\|\| | 2.487 | NM_005724 | 174 |
| CLDN23 | \|\|CLDN23\|\|claudin 23\|\| | 2.478 | NM_194284 | 175 |
| EDAR | \|\|ED5\|\|ED3\|\|EDAR\|\|EDA-A1R\|\|DL\|\|EDA3\|\|ED1R\|\|ECTODYSPLASIN RECEPTOR\|\|EDA-A1 RECEPTOR\|\|downless (mouse) homolog\|\|ectodysplasin 1, anhidrotic receptor\|\|ECTODYSPLASIN A1 ISOFORM RECEPTOR\|\|downless, mouse, homolog of\|\| | 2.473 | NM_022336 | 176 |
| KLHL5 | \|\|KLHL5\|\|kelch-like 5 (*Drosophila*)\|\| | 2.472 | NM_199039 | 177 |
| VDR | \|\|VDR\|\|NR1I1\|\|VITAMIN D RECEPTOR\|\|1,25-@DIHYDROXYVITAMIN D3 RECEPTOR\|\|VITAMIN D HORMONE RECEPTOR\|\|vitamin D (1,25-dihydroxyvitamin D3) receptor\|\| | 2.468 | NM_000376 | 178 |

TABLE 1-continued

| | EE Transcriptome | | | |
|---|---|---|---|---|
| Common Name | Description | Fold Change | Genbank Accession number | SEQ ID NO |
| SLC15A1 | \|\|SLC15A1\|\|HPECT1\|\|peptide transporter HPEPT1\|\|HYDROGEN ION/PEPTIDE COTRANSPORTER, INTESTINAL\|\|solute carrier family 15 (oligopeptide transporter), member 1\|\| | 2.463 | NM_005073 | 179 |
| IFI30 | \|\|IFI-30\|\|IP30\|\|IFI30\|\|GILT\|\|MGC32056\|\| INTERFERON-GAMMA-INDUCIBLE PROTEIN 30\|\|LYSOSOMAL THIOL REDUCTASE, GAMMA-INTERFERON-INDUCIBLE\|\|interferon, gamma-inducible protein 30\|\|gamma-interferon-inducible lysosomal thiol reductase\|\|interferon, gamma-inducible protein 30 preprotein\|\| | 2.454 | NM_006332 | 180 |
| SLCO3A1 | \|\|SLC21A11\|\|OATP-D\|\|SLCO3A1\|\|OATP3A1\|\|solute carrier organic anion transporter family, member 3A1\|\|solute carrier family 21 (organic anion transporter), member 11\|\| | 2.452 | NM_013272 | 181 |
| | | 2.439 | AK023647 | 182 |
| GALNT5 | \|\|GALNT5\|\|UDP-N-acetyl-alpha-D-galactosamine:polypeptide N-acetylgalactosaminyltransferase 5 (GalNAc-T5)\|\| | 2.438 | NM_014568 | 183 |
| LY75 | \|\|GP200-MR6\|\|DEC-205\|\|LY75\|\|DEC205\|\|lymphocyte antigen 75\|\| | 2.437 | NM_002349 | 184 |
| OR2A20P | \|\|HSDJ0798C17\|\|OR2A9P\|\|olfactory receptor, family 2, subfamily A, member 9 pseudogene\|\| | 2.435 | BC016940 | 185 |
| IGSF4 | \|\|ST17\|\|IGSF4\|\|BL2\|\|NECL2\|\|SYNCAM\|\| TSLC1\|\|nectin-like protein 2\|\|SYNAPTIC CELL ADHESION MOLECULE\|\|immunoglobulin superfamily, member 4\|\|tumor suppressor in lung cancer 1\|\| | 2.409 | NM_014333 | 186 |
| NTRK3 | \|\|NTRK3\|\|TRKC\|\|NEUROTROPHIN 3 RECEPTOR\|\|TYROSINE KINASE RECEPTOR C\|\|neurotrophic tyrosine kinase, receptor, type 3\|\| | 2.382 | NM_002530 | 187 |
| KIAA1337 | \|\|KIAA1337\|\|KIAA1337 protein\|\| | 2.379 | XM_052561 | 188 |
| GGH | \|\|3.4.19.9\|\|GGH\|\|gamma-glutamyl hydrolase precursor\|\|gamma-glutamyl hydrolase (conjugase, folylpolygammaglutamyl hydrolase)\|\| | 2.376 | NM_003878 | 189 |
| P2RY1 | \|\|P2RY1\|\|ATP receptor\|\|PURINOCEPTOR P2Y1\|\|platelet ADP receptor\|\|P2Y purinoceptor 1\|\|purinergic receptor P2Y1\|\|P2 purinoceptor subtype Y1\|\|purinergic receptor P2Y, G-protein coupled, 1\|\|PURINERGIC RECEPTOR P2Y, G PROTEIN-COUPLED, 1\|\| | 2.363 | NM_002563 | 190 |
| APOL2 | \|\|APOL2\|\|APOL-II\|\|apolipoprotein L-II\|\|apolipoprotein L2\|\|apolipoprotein L, 2\|\| | 2.347 | NM_145637 | 191 |
| TAP1 | \|\|RING4\|\|ABC17\|\|D6S114E\|\|ABCB2 \|\|TAP1\|\|APT1\|\|PEPTIDE TRANSPORTER PSF1\|\|TRANSPORTER, ABC, MHC, 1\|\|ABC transporter, MHC 1\|\|antigen peptide transporter 1\|\|peptide supply factor 1\|\|ABC TRANSPORTER, MHC, 1\|\|ATP-BINDING CASSETTE, SUBFAMILY B, MEMBER 2\|\|TRANSPORTER ASSOCIATED WITH ANTIGEN PROCESSING 1\|\|ATP-binding cassette, sub-family B, member 2\|\|ATP-binding cassette, | 2.332 | NM_000593 | 192 |

TABLE 1-continued

EE Transcriptome

| Common Name | Description | Fold Change | Genbank Accession number | SEQ ID NO |
|---|---|---|---|---|
| | sub-family B (MDR/TAP), member 2\|\|ATP-BINDING CASSETTE TRANSPORTER, MAJOR HISTOCOMPATIBILITY COMPLEX, 1\|\|transporter 1, ATP-binding cassette, sub-family B (MDR/TAP)\|\|transporter, ATP-binding cassette, major histocompatibility complex, 1\|\| | | | |
| SMILE | \|\|FLJ90492\|\|hypothetical protein FLJ90492\|\| | 2.303 | NM_181783 | 193 |
| RRM2 | \|\|1.17.4.1\|\|RRM2\|\|RIBONUCLEOTIDE REDUCTASE, R2 SUBUNIT\|\|RIBONUCLEOTIDE REDUCTASE, SMALL SUBUNIT\|\|ribonucleotide reductase M2 polypeptide\|\|RIBONUCLEOTIDE REDUCTASE, M2 SUBUNIT\|\| | 2.297 | NM_001034 | 194 |
| PARP14 | \|\|KIAA1268\|\|KIAA1268 protein\|\| | 2.276 | BX648758 | 195 |
| PRICKLE2 | \|\|PRICKLE2\|\|prickle-like 2 (Drosophila)\|\|PRICKLE, DROSOPHILA, HOMOLOG OF, 2\|\| | 2.272 | NM_198859 | 196 |
| NAV1 | \|\|NAV1\|\|neuron navigator 1\|\| | 2.265 | NM_020443 | 197 |
| RARB | \|\|\|\|RARB\|\|retinoic acid receptor, beta\|\| | 2.241 | NM_000965 | 198 |
| NDFIP2 | \|\|NDFIP2\|\|Nedd4 family interacting protein 2\|\| | 2.233 | XM_041162 | 199 |
| LOC152485 | \|\|LOC152485\|\|hypothetical protein LOC152485\|\| | 2.231 | NM_178835 | 200 |
| BAZ2A | \|\|BAZ2A\|\|KIAA0314\|\|TIP5\|\|TTF-I interacting peptide 5\|\|bromodomain adjacent to zinc finger domain, 2A\|\| | 2.228 | NM_013449 | 201 |
| ETV7 | \|\|TELB\|\|ETV7\|\|ETS TRANSCRIPTION FACTOR TEL2\|\|ets variant gene 7 (TEL2 oncogene)\|\| | 2.212 | NM_016135 | 202 |
| LTA4H | \|\|3.3.2.6\|\|LTA4H\|\|leukotriene A4 hydrolase\|\| | 2.205 | NM_000895 | 203 |
| SLC16A1 | \|\|SLC16A1\|\|MCT1\|\|monocarboxylate transporter 1\|\|solute carrier family 16, member 1\|\|SOLUTE CARRIER FAMILY 16 (MONOCARBOXYLIC ACID TRANSPORTER), MEMBER 1\|\|solute carrier family 16 (monocarboxylic acid transporters), member 1\|\| | 2.194 | NM_003051 | 204 |
| ARMCX3 | \|\|ALEX3\|\|ALEX3 protein\|\|ARM PROTEIN LOST IN EPITHELIAL CANCERS, X CHROMOSOME, 3\|\| | 2.192 | NM_016607 | 205 |
| C10orf128 | \|\|LOC170371\|\|hypothetical protein LOC170371\|\| | 2.187 | BC047724 | 206 |
| ARHGAP8 | \|\|FLJ20185\|\|ARHGAP8\|\|PP610\|\|BPGAP1\|\|BCH domain-containing Cdc42GAP-like protein\|\|Rho GTPase activating protein 8\|\|Rho GTPase activating protein 8 isoform 4\|\|Rho GTPase activating protein 8 isoform 1\|\|Rho GTPase activating protein 8 isoform 2\|\|Rho GTPase activating protein 8 isoform 3\|\|Rho GTPase activating protein 8 isoform 5\|\| | 2.185 | NM_017701 | 207 |
| TMPRSS4 | \|\|TMPRSS4\|\|transmembrane protease, serine 4\|\| | 2.156 | NM_019894 | 208 |
| CTSS | \|\|CTSS\|\|3.4.22.27\|\|MGC3886\|\|cathepsin S\|\|cathepsin S preproprotein\|\| | 2.152 | NM_004079 | 209 |
| LOC158402 | | 2.144 | AK095652 | 210 |
| TAPBP | \|\|TAPBP\|\|TPSN\|\|TPN\|\|NGS17\|\|TAP-associated protein\|\|TAP-binding protein\|\|TAP binding protein (tapasin)\|\|tapasin isoform 2 precursor\|\|tapasin isoform 1 precursor\|\|tapasin isoform 3 precursor\|\| | 2.131 | NM_003190 | 211 |

TABLE 1-continued

| | EE Transcriptome | | | |
|---|---|---|---|---|
| Common Name | Description | Fold Change | Genbank Accession number | SEQ ID NO |
| CTEN | ||CTEN||C-terminal tensin-like||C-TERMINAL TENSIN-LIKE PROTEIN|| | 2.127 | NM_032865 | 212 |
| T3JAM | ||T3JAM||TRAF3-INTERACTING JNK-ACTIVATING MODULATOR||TRAF3-interacting Jun N-terminal kinase (JNK)-activating modulator|| | 2.107 | NM_025228 | 213 |
| CD44 | ||CD44R||MDU2||INLU||MDU3||Pgp1||MIC4||MC56||CD44||HERMES ANTIGEN||Lutheran inhibitor, dominant (monoclonal antibody A3D8)||CD44 antigen (homing function and Indian blood group system)|| | 2.106 | NM_000610 | 214 |
| FLJ21103 | ||FLJ21103||hypothetical protein FLJ21103|| | 2.104 | NM_024556 | 215 |
| SLC16A2 | ||SLC16A2||MCT8||XPCT||X-linked PEST-containing transporter||DXS128E MONOCARBOXYLATE TRANSPORTER 8 DEFICIENCY||solute carrier family 16, member 2||SOLUTE CARRIER FAMILY 16 (MONOCARBOXYLIC ACID TRANSPORTER), MEMBER 2||solute carrier family 16 (monocarboxylic acid transporters), member 2 (putative transporter)|| | 2.09 | NM_006517 | 216 |
| GALNAC4S-6ST | ||GalNAc4S-6ST||BRAG||KIAA0598||B-CELL RAG-ASSOCIATED GENE||N-ACETYLGALACTOSAMINE 4-SULFATE 6-O-SULFOTRANSFERASE||B cell RAG associated protein|| | 2.083 | NM_015892 | 217 |
| MAP3K14 | ||FTDCR1B||MAP3K14||HSNIK||NF-KAPPA-B-INDUCING KINASE||serine/threonine protein-kinase||SERINE/THREONINE PROTEIN KINASE NIK||mitogen-activated protein kinase kinase kinase 14|| | 2.074 | NM_003954 | 218 |
| ATP8B1 | ||PFIC1||ATPIC||ATP8B1||BRIC||benign recurrent intrahepatic cholestasis||FAMILIAL INTRAHEPATIC CHOLESTASIS GENE 1||ATPase, CLASS I, TYPE 8B, MEMBER 1||ATPase, Class I, type 8B, member 1||progressive familial intrahepatic cholestasis 1, Byler disease||familial intrahepatic cholestasis 1, (progressive, Byler disease and benign recurrent)|| | 2.064 | NM_005603 | 219 |
| RAB40B | ||RAB40B||SEC4L||RAR||RAB40B, member RAS oncogene family||GTP-binding protein homologous to *Saccharomyces cerevisiae* SEC4|| | 2.063 | NM_006822 | 220 |
| | | 2.061 | BQ717725 | 221 |
| NFKBIE | ||NFKBIE||IKBE||INHIBITOR OF KAPPA LIGHT CHAIN GENE ENHANCER IN B CELLS, EPSILON||nuclear factor of kappa light polypeptide gene enhancer in B-cells inhibitor, epsilon||NUCLEAR FACTOR OF KAPPA LIGHT CHAIN GENE ENHANCER IN B CELLS INHIBITOR, EPSILON|| | 2.06 | NM_004556 | 222 |
| | | 2.058 | AK026659 | 223 |
| ELOVL5 | ||ELOVL5||ELOVL family member 5, elongation of long chain fatty acids (FEN1/Elo2, SUR4/Elo3-like, yeast)|| | 2.052 | NM_021814 | 224 |
| LOC132430 | | 2.047 | XR_000195 | 225 |
| GPX4 | ||snGPx||1.11.1.9||GPX4||sperm nucleus glutathione peroxidase||glutathione peroxidase 4 (phospholipid hydroperoxidase)|| | 2.045 | NM_002085 | 226 |

TABLE 1-continued

EE Transcriptome

| Common Name | Description | Fold Change | Genbank Accession number | SEQ ID NO |
|---|---|---|---|---|
| CBX6 | \|\|CBX6\|\|chromobox homolog 6\|\| | 2.041 | NM_014292 | 227 |
| NCF1 | \|\|p47-PHOX\|\|NOXO2\|\|NCF1\|\|p47phox\|\|Neutrophil cytosolic factor-1 (47 kD)\|\|neutrophil cytosolic factor 1 (47 kDa, chronic granulomatous disease, autosomal 1)\|\|neutrophil cytosolic factor 1 (47 kD, chronic granulomatous disease, autosomal 1)\|\| | 2.031 | NM_000265 | 228 |
| GLIPR1 | \|\|RTVP1\|\|GLIPR1\|\|glioma pathogenesis-related protein\|\|GLI pathogenesis-related 1 (glioma)\|\|related to testis-specific, vespid, and pathogenesis proteins 1\|\| | 2.027 | NM_006851 | 229 |
| CD44 | \|\|CD44R\|\|MDU2\|\|INLU\|\|MDU3\|\|Pgp1\|\|MIC4\|\|MC56\|\|CD44\|\|HERMES ANTIGEN\|\|Lutheran inhibitor, dominant (monoclonal antibody A3D8)\|\|CD44 antigen (homing function and Indian blood group system)\|\| | 2.007 | NM_000610 | 230 |
|  |  | 2.002 | AK127315 | 231 |
| SLCO3A1 | \|\|SLC21A11\|\|OATP-D\|\|SLCO3A1\|\|OATP3A1\|\|solute carrier organic anion transporter family, member 3A1\|\|solute carrier family 21 (organic anion transporter), member 11\|\| | 1.999 | NM_013272 | 232 |
| COL8A2 | \|\|FECD\|\|PPCD2\|\|COL8A2\|\|FLJ00201\|\|COLLAGEN, TYPE VIII, ALPHA-2\|\|collagen VIII, alpha-2 polypeptide\|\|collagen, type VIII, alpha 2\|\| | 1.992 | NM_005202 | 233 |
| KCTD12 | \|\|KCTD12\|\|potassium channel tetramerisation domain containing 12\|\| | 1.985 | NM_138444 | 234 |
| DLG5 | \|\|PDLG\|\|KIAA0583\|\|DLG5\|\|discs large homolog 5\|\|placenta and prostate DLG\|\|discs, large homolog 5 (*Drosophila*)\|\|DISCS LARGE, *DROSOPHILA*, HOMOLOG OF, 5\|\| | 1.969 | NM_004747 | 235 |
| ABCC5 | \|\|MOAT-C\|\|ABCC5\|\|MRP5\|\|EST277145\|\|ABC33\|\|SMRP\|\|pABC11\|\|MOATC\|\|MULTI DRUG RESISTANCE-ASSOCIATED PROTEIN 5\|\|canalicular multispecific organic anion transporter C\|\|ATP-binding cassette, sub-family C, member 5\|\|ATP-BINDING CASSETTE, SUBFAMILY C, MEMBER 5\|\|ATP-binding cassette, sub-family C (CFTR/MRP), member 5\|\| | 1.969 | NM_005688 | 236 |
| PRSS12 | \|\|leydin\|\|BSSP3\|\|MGC12722\|\|BSSP-3\|\|PRSS12\|\|neurotrypsin precursor\|\|brain-specific serine protease 3\|\|protease, serine, 12 (neurotrypsin, motopsin)\|\| | 1.965 | NM_003619 | 237 |
| CLN5 | \|\|NCL\|\|CLN5\|\|CLN5 GENE\|\|ceroid-lipofuscinosis, neuronal 5\|\| | 1.96 | NM_006493 | 238 |
| ZC3HDC1 | \|\|ZC3HDC1\|\|zinc finger CCCH type domain containing 1\|\| | 1.947 | NM_022750 | 239 |
| EHD2 | \|\|EHD2\|\|EH-domain containing 2\|\|EH DOMAIN-CONTAINING 2\|\|EH domain containing 2\|\| | 1.94 | NM_014601 | 240 |
| RAD50 | \|\|hRad50\|\|RAD50\|\|RAD50-2\|\|RAD50 homolog (*S. cerevisiae*)\|\|RAD50 homolog isoform 1\|\|RAD50 homolog isoform 2\|\|RAD50, *S. CEREVISIAE*, HOMOLOG OF\|\| | 1.926 | NM_005732 | 241 |

TABLE 1-continued

EE Transcriptome

| Common Name | Description | Fold Change | Genbank Accession number | SEQ ID NO |
|---|---|---|---|---|
| GSDML | \|\|\|\|GSDML\|\|gasdermin-like\|\| | 1.92 | NM_018530 | 242 |
| TLOC1 | \|\|TLOC1\|\|HTP1\|\|Dtrp1 protein\|\|translocation protein 1\|\|TRANSLOCATION PROTEIN 1, *DROSOPHILA*, HOMOLOG OF\|\|membrane protein SEC62, *S. cerevisiae*, homolog of\|\|MEMBRANE PROTEIN SEC62, *S. CEREVISIAE*, HOMOLOG OF\|\| | 1.918 | NM_003262 | 243 |
| EMR2 | \|\|EMR2\|\|EGF-LIKE MODULE-CONTAINING, MUCIN-LIKE HORMONE RECEPTOR 2\|\|egf-like module containing, mucin-like, hormone receptor-like 2\|\|egf-like module containing, mucin-like, hormone receptor-like sequence 2 isoform d\|\|egf-like module containing, mucin-like, hormone receptor-like sequence 2 isoform e\|\|egf-like module containing, mucin-like, hormone receptor-like sequence 2 isoform f\|\|egf-like module containing, mucin-like, hormone receptor-like sequence 2 isoform g\|\|egf-like module containing, mucin-like, hormone receptor-like sequence 2 isoform a\|\|egf-like module containing, mucin-like, hormone receptor-like sequence 2 isoform b\|\|egf-like module containing, mucin-like, hormone receptor-like sequence 2 isoform c\|\| | 1.914 | NM_013447 | 244 |
| NCF1 | \|\|p47-PHOX\|\|NOXO2\|\|NCF1\|\|p47phox\|\|Neutrophil cytosolic factor-1 (47 kD)\|\|neutrophil cytosolic factor 1 (47 kDa, chronic granulomatous disease, autosomal 1)\|\|neutrophil cytosolic factor 1 (47 kD, chronic granulomatous disease, autosomal 1)\|\| | 1.91 | NM_000265 | 245 |
| ARHGEF6 | \|\|alpha-PIX\|\|alphaPIX\|\|PIXA\|\|Cool-2\|\|MRX46\|\|KIAA0006\|\|ARHGEF6\|\|COOL2\|\|PAK-interacting exchange factor, alpha\|\|Rac/Cdc42 guanine exchange factor (GEF) 6\|\|rho guanine nucleotide exchange factor 6\|\|Rac/Cdc42 guanine nucleotide exchange factor 6\|\|Rac/Cdc42 guanine nucleotide exchange factor (GEF) 6\|\| | 1.909 | NM_004840 | 246 |
| ZSWIM5 | \|\|ZSWIM5\|\|zinc finger, SWIM domain containing 5\|\| | 1.905 | XM_046581 | 247 |
| CHST6 | \|\|\|\|CHST6\|\|carbohydrate (N-acetylglucosamine 6-O) sulfotransferase 6\|\| | 1.897 | NM_021615 | 248 |
| EPLIN | \|\|EPLIN\|\|SREBP3\|\|STEROL REGULATORY ELEMENT-BINDING PROTEIN 3\|\|epithelial protein lost in neoplasm beta\|\| | 1.897 | NM_016357 | 249 |
| IL27RA | \|\|TCCR\|\|IL27RA\|\|CRL1\|\|WSX1\|\|zcytor1\|\|T-cell cytokine receptor\|\|class I cytokine receptor\|\|interleukin 27 receptor, alpha\|\| | 1.897 | NM_004843 | 250 |
| RGS19 | \|\|RGSGAIP\|\|RGS19\|\|G alpha interacting protein\|\|G PROTEIN, ALPHA-INTERACTING PROTEIN\|\|G protein signalling regulator 19\|\|regulator of G-protein signalling 19\|\|REGULATOR OF G PROTEIN | 1.891 | NM_005873 | 251 |

TABLE 1-continued

EE Transcriptome

| Common Name | Description | Fold Change | Genbank Accession number | SEQ ID NO |
|---|---|---|---|---|
| | SIGNALING 19\|\|guanine nucleotide binding protein alpha inhibiting activity polypeptide 3 interacting protein\|\| | | | |
| ARRDC2 | \|\|CLONE24945\|\|PP2703\|\|ARRDC2\|\| arrestin domain containing 2\|\| | 1.887 | NM_015683 | 252 |
| HES2 | \|\|\|\|Similar to Transcription factor HES-2 (Hairy and enhancer of split 2) (LOC388592), mRNA\|\| | 1.883 | XM_375684 | 253 |
| RIPK2 | \|\|RIPK2\|\|CARDIAK\|\|RICK\|\|CARD3\|\| RIP2\|\|CARD-CONTAINING ICE-ASSOCIATED KINASE\|\|RECEPTOR-INTERACTING PROTEIN 2\|\|RIP-LIKE INTERACTING CLARP KINASE\|\|RECEPTOR-INTERACTING SERINE/THREONINE KINASE 2\|\|receptor interacting protein 2\|\|receptor-interacting serine-threonine kinase 2\|\| | 1.873 | NM_003821 | 254 |
| FGF11 | \|\|FGF11\|\|MGC45269\|\|FHF3\|\|fibroblast growth factor 11\|\|fibroblast growth factor homologous factor 3\|\| | 1.868 | NM_004112 | 255 |
| DRAP1 | \|\|\|\|*Homo sapiens* similar to tankyrase, TRF1-interacting ankyrin-related ADP-ribose polymerase 2; tankyrase 2 (LOC376558), mRNA\|\| | 1.865 | BC018095 | 256 |
| SCIN | \|\|scinderin\|\|SCIN\|\| | 1.861 | NM_033128 | 257 |
| HSPA5BP1 | \|\|HSPA5BP1\|\|heat shock 70 kDa protein 5 (glucose-regulated protein, 78 kDa) binding protein 1\|\| | 1.861 | NM_017870 | 258 |
| ADAM8 | \|\|MS2\|\|CD156\|\|ADAM8\|\|HUMAN LEUKOCYTE DIFFERENTIATION ANTIGEN\|\|a disintegrin and metalloproteinase domain 8\|\|a disintegrin and metalloproteinase domain 8 precursor\|\| | 1.858 | NM_001109 | 259 |
| NFATC2 | \|\|NFATP\|\|NFATC2\|\|NFAT pre-existing subunit\|\|NFAT TRANSCRIPTION COMPLEX, PREEXISTING COMPONENT\|\|T cell transcription factor NFAT1\|\|nuclear factor of activated T-cells, cytoplasmic 2\|\|nuclear factor of activated T-cells, cytoplasmic, calcineurin-dependent 2\|\|NUCLEAR FACTOR OF ACTIVATED T CELLS, PREEXISTING COMPONENT\|\|preexisting nuclear factor of activated T-cells 2 isoform B\|\|preexisting nuclear factor of activated T-cells 2 isoform C\|\|NUCLEAR FACTOR OF ACTIVATED T CELLS, CYTOPLASMIC, CALCINEURIN-DEPENDENT 2\|\| | 1.858 | NM_173091 | 260 |
| MGC14289 | \|\|MGC14289\|\|similar to RIKEN cDNA 1200014N16 gene\|\| | 1.858 | NM_080660 | 261 |
| GPR143 | \|\|GPR143\|\|OA1 GENE\|\|ocular albinism-1, Nettleship-Falls type\|\|G protein-coupled receptor 143\|\|ALBINISM, OCULAR, TYPE I\|\|NETTLESHIP-FALLS TYPE OCULAR ALBINISM OCULAR ALBINISM 1 GENE\|\| | 1.854 | NM_000273 | 262 |
| | | 1.845 | AK056817 | 263 |
| FLJ10350 | \|\|FLJ10350\|\|hypothetical protein FLJ10350\|\| | 1.845 | NM_018067 | 264 |
| HCP5 | \|\|HCP5\|\|D6S2650E\|\|HLA complex P5\|\|MHC class I region ORF\|\|MAJOR HISTOCOMPATIBILITY COMPLEX, CLASS I, GENE P5-1\|\| | 1.843 | NM_006674 | 265 |
| WARP | \|\|WARP\|\|von Willebrand factor A domain-related protein\|\| | 1.831 | NM_022834 | 266 |
| MGC15397 | \|\|MGC15397\|\|similar to RIKEN cDNA 5730578N08 gene\|\| | 1.827 | NM_080652 | 267 |

TABLE 1-continued

| | | | | |
|---|---|---|---|---|
| | EE Transcriptome | | | |
| Common Name | Description | Fold Change | Genbank Accession number | SEQ ID NO |
| GLIS2 | \|\|GLIS2\|\|GLI-SIMILAR PROTEIN 2\|\|Kruppel-like zinc finger protein GLIS2\|\| | 1.82 | NM_032575 | 268 |
| ARHGAP15 | | 1.816 | AI510829 | 269 |
| STK17B | \|\|DRAK2\|\|STK17B\|\|SERINE/THREONINE PROTEIN KINASE 17B\|\|death-associated protein kinase-related 2\|\|serine/threonine kinase 17b (apoptosis-inducing)\|\|DAP KINASE-RELATED APOPTOSIS-INDUCING PROTEIN KINASE 2\|\| | 1.812 | NM_004226 | 270 |
| CLNS1A | \|\|\|\|CLNS1A\|\|chloride channel, nucleotide-sensitive, 1A\|\| | 1.808 | NM_001293 | 271 |
| C9orf40 | \|\|C9orf40\|\|chromosome 9 open reading frame 40\|\| | 1.8 | NM_017998 | 272 |
| FAM20C | \|\|FAM20C\|\|family with sequence similarity 20, member C\|\| | 1.799 | NM_020223 | 273 |
| ADRBK2 | \|\|GRK3\|\|BARK2\|\|2.7.1.126\|\|ADRBK 2\|\|BETA-ADRENERGIC RECEPTOR KINASE 2\|\|adrenergic, beta, receptor kinase 2\|\|beta adrenergic receptor kinase 2\|\| | 1.791 | NM_005160 | 274 |
| BBAP | \|\|BBAP\|\|rhysin 2\|\| | 1.788 | NM_138287 | 275 |
| EPB41L2 | \|\|EPB41L2\|\|4.1G\|\|4.1-G\|\|ERYTHROCYTE MEMBRANE PROTEIN 4.1-LIKE 2\|\|NONERYTHROID PROTEIN 4.1, GENERAL TYPE\|\|erythrocyte membrane protein band 4.1-like 2\|\| | 1.765 | NM_001431 | 276 |
| MGC7036 | \|\|MGC7036\|\|hypothetical protein MGC7036\|\| | 1.759 | NM_145058 | 277 |
| | | 1.759 | BM999272 | 278 |
| TCF4 | \|\|SEF2-1B\|\|TCF4\|\|E2-2\|\|ITF2\|\|transcription factor 4\|\|IMMUNOGLOBULIN TRANSCRIPTION FACTOR 2\|\|transcription factor 4 isoform b\|\|Transcription factor-4 (immunoglobulin transcription factor-2)\|\| | 1.756 | NM_003199 | 279 |
| ARHGEF5 | \|\|P60\|\|ARHGEF5\|\|TIM1\|\|oncogene TIM\|\|transforming immortalized mammary oncogene\|\|guanine nucleotide regulatory protein TIM\|\|Rho guanine nucleotide exchange factor 5\|\|Rho guanine nucleotide exchange factor (GEF) 5\|\| | 1.753 | NM_005435 | 280 |
| SFXN1 | \|\|SFXN1\|\|sideroflexin 1\|\| | 1.75 | NM_022754 | 281 |
| KIAA1404 | \|\|KIAA1404\|\|KIAA1404 protein\|\| | 1.746 | NM_021035 | 282 |
| SMTN | \|\|smoothelin\|\|SMTN\|\|smoothelin isoform a\|\|smoothelin isoform b\|\|smoothelin isoform c\|\| | 1.745 | NM_134269 | 283 |
| TRAF4 | \|\|CART1\|\|MLN62\|\|RNF83\|\|TRAF4\|\|malignant 62\|\|TNF receptor-associated factor 4\|\|tumor necrosis receptor-associated factor 4A\|\|TNF receptor-associated factor 4 isoform 1\|\|TNF receptor-associated factor 4 isoform 2\|\|CYSTEINE-RICH DOMAIN ASSOCIATED WITH RING AND TRAF DOMAINS\|\| | 1.739 | NM_004295 | 284 |
| GCNT2 | | 1.737 | AK058074 | 285 |
| SPTBN1 | \|\|\|\|SPTBN1\|\|spectrin, beta, non-erythrocytic 1\|\| | 1.716 | NM_003128 | 286 |
| FOXQ1 | \|\|FOXQ1\|\|forkhead box Q1\|\| | 1.709 | NM_033260 | 287 |
| TNFRSF5 | \|\|Bp50\|\|TNFRSF5\|\|MGC9013\|\|CDW40\|\|CD40 antigen\|\|CD40L receptor\|\|B CELL-ASSOCIATED MOLECULE CD40\|\|CD40 type II isoform\|\|B cell surface antigen CD40\|\|nerve growth factor receptor-related B-lymphocyte activation molecule\|\|tumor necrosis factor | 1.706 | NM_001250 | 288 |

TABLE 1-continued

EE Transcriptome

| Common Name | Description | Fold Change | Genbank Accession number | SEQ ID NO |
|---|---|---|---|---|
| | receptor superfamily, member 5\|\|tumor necrosis factor receptor superfamily, member 5 isoform 2 precursor\|\|tumor necrosis factor receptor superfamily, member 5 isoform 1 precursor\|\| | | | |
| NCF4 | \|\|p40phox\|\|NCF4\|\|p40-PHOX\|\|NCF, 40-KD\|\|Neutrophil cytosolic factor-4\|\|neutrophil cytosolic factor 4, 40 kDa\|\|neutrophil cytosolic factor 4 (40 kD) isoform 1\|\|neutrophil cytosolic factor 4 (40 kD) isoform 2\|\| | 1.69 | NM_013416 | 289 |
| MGAT3 | \|\|GNT-III\|\|2.4.1.144\|\|GNT3\|\|MGAT3\|\|BETA-1,4-@MANNOSYL-GLYCOPROTEIN BETA-1,4-N-ACETYLGLUCOSAMINYLTRANSFERASE\|\|UDP-N-ACETYLGLUCOSAMINE:BETA-D-MANNOSIDE BETA-1,4-N-ACETYLGLUCOSAMINYLTRANSFERASE\|\|mannosyl (beta-1,4-)-glycoprotein beta-1,4-N-acetylglucosaminyltransferase\|\| | 1.688 | NM_002409 | 290 |
| DRAP1 | \|\|\|\|*Homo sapiens* similar to tankyrase, TRF1-interacting ankyrin-related ADP-ribose polymerase 2; tankyrase 2 (LOC376558), mRNA\|\| | 1.687 | BC018095 | 291 |
| HLA-B | \|\|HLA-B\|\|HLA-B HISTOCOMPATIBILITY TYPE\|\|major histocompatibility complex, class I, B\|\|HLA class I histocompatibility antigen, B alpha chain\|\| | 1.686 | NM_005514 | 292 |
| EPAS1 | \|\|HIF2A\|\|MOP2\|\|HIF2-ALPHA\|\|EPAS1\|\|endothelial PAS domain protein 1\|\|MEMBER OF PAS SUPERFAMILY 2\|\|HYPOXIA-INDUCIBLE FACTOR 2, ALPHA SUBUNIT\|\| | 1.684 | NM_001430 | 293 |
| LOC283578 | \|\|LOC283578\|\|hypothetical protein LOC283578\|\| | 1.684 | XM_208746 | 294 |
| MAOA | \|\|1.4.3.4\|\|MAOA\|\|MAOA BRUNNER SYNDROME\|\|monoamine oxidase A\|\| | 1.677 | NM_000240 | 295 |
| CDCP1 | \|\|CDCP1\|\|CUB domain-containing protein 1\|\| | 1.663 | NM_022842 | 296 |
| TNIP2 | \|\|TNIP2\|\|TNFAIP3 interacting protein 2\|\| | 1.66 | NM_024309 | 297 |
| RAB8B | \|\|RAB8B\|\|RAB8B, member RAS oncogene family\|\| | 1.653 | NM_016530 | 298 |
| | | 1.644 | BM988141 | 299 |
| TLE4 | \|\|ESG4\|\|TLE4\|\|E(spI)\|\|BCE-1\|\|B lymphocyte gene 1\|\|transducin-like enhancer protein 4\|\|enhancer of split groucho 4\|\|transducin-like enhancer of split 4 (E(sp1) homolog, *Drosophila*)\|\| | 1.636 | NM_007005 | 300 |
| ITGAE | \|\|HUMINAE\|\|ITGAE\|\|CD103 ANTIGEN\|\|INTEGRIN, ALPHA-E\|\|HUMAN MUCOSAL LYMPHOCYTE ANTIGEN 1, ALPHA SUBUNIT\|\|integrin, alpha E (antigen CD103, human mucosal lymphocyte antigen 1; alpha polypeptide)\|\| | 1.635 | NM_002208 | 301 |
| RAB33A | \|\|RAB33A\|\|MGC1488\|\|RabS10\|\|RAS-ASSOCIATED PROTEIN RAB33A\|\|Ras-related protein Rab-33A\|\|Small GTP-binding protein S10\|\|RAB33A, member RAS oncogene family\|\| | 1.63 | NM_004794 | 302 |
| CD97 | \|\|CD97\|\|TM7LN1\|\|CD97 antigen\|\|leukocyte antigen CD97\|\|seven-span transmembrane protein\|\|CD97 antigen isoform 1 | 1.628 | NM_078481 | 303 |

TABLE 1-continued

| | EE Transcriptome | | | |
|---|---|---|---|---|
| Common Name | Description | Fold Change | Genbank Accession number | SEQ ID NO |
| | precursor\|\|CD97 antigen isoform 2 precursor\|\| | | | |
| SLCO3A1 | \|\|SLC21A11\|\|OATP-D\|\|SLCO3A1\|\|OATP3A1\|\|solute carrier organic anion transporter family, member 3A1\|\|solute carrier family 21 (organic anion transporter), member 11\|\| | 1.623 | NM_013272 | 304 |
| TNIP2 | \|\|TNIP2\|\|TNFAIP3 interacting protein 2\|\| | 1.618 | NM_024309 | 305 |
| GSTO1 | \|\|GSTTLp28\|\|GSTO1\|\|glutathione-S-transferase like\|\|glutathione-S-transferase omega 1\|\|GLUTATHIONE S-TRANSFERASE, OMEGA-1\|\|glutathione transferase omega\|\|glutathione S-transferase omega 1\|\| | 1.615 | NM_004832 | 306 |
| DTNBP1 | \|\|SDY\|\|DTNBP1\|\|DYSBINDIN\|\|DYSTROBREVIN-BINDING PROTEIN 1\|\|SANDY, MOUSE, HOMOLOG OF\|\|dystrobrevin binding protein 1\|\| | 1.597 | NM_183040 | 307 |
| ARHGAP26 | \|\|GRAF\|\|KIAA0621\|\|GRAF GRAF/MLL FUSION GENE\|\|GTPase regulator associated with focal adhesion kinase pp125(FAK)\|\|GTPase regulator associated with the focal adhesion kinase pp125\|\| | 1.576 | NM_015071 | 308 |
| KIAA1305 | \|\|KIAA1305\|\|KIAA1305 protein\|\|hypothetical protein FLJ11811\|\| | 1.575 | NM_025081 | 309 |
| ETV7 | \|\|TELB\|\|ETV7\|\|ETS TRANSCRIPTION FACTOR TEL2\|\|ets variant gene 7 (TEL2 oncogene)\|\| | 1.575 | NM_016135 | 310 |
| DUOX1 | \|\|DUOX1\|\|THOX1\|\|THYROID OXIDASE 1\|\|dual oxidase 1\|\| | 1.567 | NM_017434 | 311 |
| PIK3CD | \|\|p110-DELTA\|\|PIK3CD\|\|p110D\|\|phosphoinositide-3-kinase, catalytic, delta polypeptide\|\|phosphatidylinositol 3-kinase, catalytic, delta polypeptide\|\|PHOSPHATIDYLINOSITOL 3-KINASE, CATALYTIC, 110-KD, DELTA\|\| | 1.563 | NM_005026 | 312 |
| | | 1.549 | BG621254 | 313 |
| FAM46A | \|\|C6orf37\|\|chromosome 6 open reading frame 37\|\| | 1.526 | NM_017633 | 314 |
| IRF6 | \|\|PIT\|\|LPS\|\|IRF6\|\|PPS\|\|VWS\|\|Popliteala pterygium syndrome\|\|interferon regulatory factor 6\|\| | 1.509 | NM_006147 | 315 |
| GSR | \|\|1.6.4.2\|\|GSR\|\|glutathione reductase\|\|GSR GLUTATHIONE REDUCTASE, HEMOLYTIC ANEMIA DUE TO DEFICIENCY OF, IN RED CELLS\|\| | 1.508 | NM_000637 | 316 |
| | | 1.506 | AF143866 | 317 |
| ACOX1 | \|\|MGC1198\|\|1.3.3.6\|\|ACOX1\|\|PALMCOX\|\|SCOX\|\|PSEUDONEONATAL ADRENOLEUKODYSTROPHY\|\|PALMITOYL-CoA OXIDASE\|\|ACYL-CoA OXIDASE, STRAIGHT-CHAIN\|\|ACYL-CoA OXIDASE, PALMITOYL, PEROXISOMAL\|\|PEROXISOMAL ACYL-CoA OXIDASE DEFICIENCY\|\|acyl-Coenzyme A oxidase isoform a\|\|acyl-Coenzyme A oxidase isoform b\|\|acyl-Coenzyme A oxidase 1, palmitoyl\|\|ADRENOLEUKODYSTROPHY, PSEUDONEONATAL ACYL-CoA OXIDASE 1, PALMITOYL\|\| | 1.504 | NM_004035 | 318 |
| RAP1A | \|\|RAP1A\|\|SMGP21\|\|KREV-1\|\|RAP1A KREV1\|\|RAS-related protein | 1.486 | NM_002884 | 319 |

TABLE 1-continued

EE Transcriptome

| Common Name | Description | Fold Change | Genbank Accession number | SEQ ID NO |
|---|---|---|---|---|
| | RAP1A||RAS-RELATED PROTEIN 1A||RAP1A, member of RAS oncogene family|| | | | |
| SIRT5 | ||SIR2L5||SIRT5||sir2-like 5||sirtuin type 5||sirtuin 5 isoform 1||sirtuin 5 isoform 2||SIR2, S. CEREVISIAE, HOMOLOG-LIKE 5||silent mating type information regulation 2, S. cerevisiae, homolog 5||sirtuin (silent mating type information regulation 2, S. cerevisiae, homolog) 5||sirtuin (silent mating type information regulation 2 homolog) 5 (S. cerevisiae)||sirtuin silent mating type information regulation 2 homolog 5 (S. cerevisiae)|| | 1.479 | NM_031244 | 320 |
| IL1RL1 | ||ST2L||DER4||IL1RL1||ST2V||FIT-1||MGC32623||T1||ST2 protein||interleukin 1 receptor-related protein||interleukin 1 receptor-like 1||GROWTH STIMULATION-EXPRESSED GENE, MOUSE, HOMOLOG OF||homolog of mouse growth stimulation-expressed gene||interleukin 1 receptor-like 1 isoform 1 precursor||interleukin 1 receptor-like 1 isoform 2 precursor||interleukin 1 receptor-like 1 isoform 3 precursor|| | 1.479 | NM_173459 | 321 |
| GOT2 | ||2.6.1.1||GOT2||ASPARTATE AMINOTRANSFERASE, MITOCHONDRIAL||aspartate aminotransferase 2 precursor||GLUTAMATE OXALOACETATE TRANSAMINASE, MITOCHONDRIAL||glutamic-oxaloacetic transaminase 2, mitochondrial (aspartate aminotransferase 2)|| | 1.477 | NM_002080 | 322 |
| | | 1.456 | BG257011 | 323 |
| PSME1 | ||REGalpha||IFI5111||PA28-ALPHA||MGC8628||PSME1||PA28alpha|| proteasome activator subunit-1||PROTEASOME ACTIVATOR 28-ALPHA||interferon-gamma-inducible protein 5111||interferon-gamma IEF SSP 5111||MCP ACTIVATOR, 29-KD SUBUNIT||29-kD MCP activator subunit||11S regulator complex alpha subunit||interferon gamma up-regulated I-5111 protein||proteasome activator subunit 1 isoform 2||proteasome activator subunit 1 isoform 1||activator of multicatalytic protease subunit 1||proteasome (prosome, macropain) activator subunit 1 (PA28 alpha)|| | 1.455 | NM_176783 | 324 |
| HA-1 | ||HLA-HA1||HA-1||KIAA0223||minor histocompatibility antigen HA-1|| | 1.449 | NM_012292 | 325 |
| IL9R | ||IL9R||interleukin 9 receptor||interleukin 9 receptor isoform 2||interleukin 9 receptor isoform 1 precursor|| | 1.44 | NM_176786 | 326 |
| PRKAA1 | ||PRKAA1||AMPK-ALPHA-1||AMPK alpha 1||AMP-ACTIVATED PROTEIN KINASE, CATALYTIC, ALPHA-1||Protein kinase, AMP-activated, catalytic, alpha-1||protein kinase, AMP-activated, alpha 1 catalytic subunit|| | 1.437 | NM_006251 | 327 |

TABLE 1-continued

| | EE Transcriptome | | | |
|---|---|---|---|---|
| Common Name | Description | Fold Change | Genbank Accession number | SEQ ID NO |
| SCARA3 | ||CSR||MSRL1||SCARA3||CELLULAR STRESS RESPONSE||MACROPHAGE SCAVENGER RECEPTOR-LIKE 1||scavenger receptor class A, member 3|| | 1.425 | NM_016240 | 328 |
| MCM10 | ||MCM10||MCM10 minichromosome maintenance deficient 10 (*S. cerevisiae*)|| | 1.416 | NM_182751 | 329 |
| C6orf83 | ||C6orf83||chromosome 6 open reading frame 83|| | 1.406 | NM_145169 | 330 |
| PSMB4 | ||PROS26||PSMB4||HN3||3.4.25.1|| proteasome subunit HsN3||macropain beta chain||proteasome chain 3||proteasome beta chain||proteasome beta 4 subunit||PROTEASOME SUBUNIT, BETA-TYPE, 4||multicatalytic endopeptidase complex beta chain||proteasome subunit, beta type, 4||proteasome (prosome, macropain) subunit, beta type, 4|| | 1.385 | NM_002796 | 331 |
| REPIN1 | ||||REPIN1||replication initiator 1|| | 1.378 | NM_013400 | 332 |
| CYB561D1 | ||FLJ39035||hypothetical protein FLJ39035|| | 1.377 | NM_182580 | 333 |
| ARPC5L | ||ARPC5L||actin related protein 2/3 complex, subunit 5-like|| | 1.367 | NM_030978 | 334 |
| DER1 | ||PRO2577||MGC3067||FLJ13784||hypothetical protein MGC3067|| | 1.342 | NM_018630 | 335 |
| KELCHL | ||FLJ14360||hypothetical protein FLJ14360|| | 1.317 | NM_032775 | 336 |
| SCML4 | ||SCML4||sex comb on midleg-like 4 (*Drosophila*)|| | 1.305 | NM_198081 | 337 |
| KIAA0323 | ||KIAA0323|| | 1.26 | AB002321 | 338 |
| C11orf31 | ||SELH||selenoprotein H|| | 1.25 | NM_170746 | 339 |
| B2M | ||beta-2-microglobulin||B2M||beta-2-microglobulin precursor|| | 1.248 | NM_004048 | 340 |
| COX4I1 | ||COXIV||COX4I1||CYTOCHROME c OXIDASE, SUBUNIT IV, ISOFORM 1||cytochrome c oxidase subunit IV isoform 1||cytochrome c oxidase subunit IV isoform 1 precursor|| | 1.201 | NM_001861 | 341 |
| RAC1 | ||||RAC1||ras-related C3 *botulinum* toxin substrate 1 (rho family, small GTP binding protein Rac1)|| | 1.186 | NM_198829 | 342 |
| COX4I1 | ||COXIV||COX4I1||CYTOCHROME c OXIDASE, SUBUNIT IV, ISOFORM 1||cytochrome c oxidase subunit IV isoform 1||cytochrome c oxidase subunit IV isoform 1 precursor|| | 1.186 | NM_001861 | 343 |
| KIAA1228 | ||KIAA1228||KIAA1228 protein|| | 1.134 | XM_036408 | 344 |
| SPRR3 | ||esophagin||SPRR3||small proline-rich protein 3|| | 0.863 | NM_005416 | 345 |
| SFRS15 | ||SFRS15||splicing factor, arginine/serine-rich 15|| | 0.833 | NM_020706 | 346 |
| ZCCHC2 | ||ZCCHC2||zinc finger, CCHC domain containing 2|| | 0.831 | NM_017742 | 347 |
| RGS11 | ||RGS11||RS11||regulator of G-protein signalling 11||REGULATOR OF G PROTEIN SIGNALING 11||regulator of G-protein signalling 11 isoform 1||regulator of G-protein signalling 11 isoform 2|| | 0.815 | NM_003834 | 348 |
| ZNF505 | ||ZNF505||zinc finger protein 505|| | 0.813 | NM_031218 | 349 |
| SCAMP4 | ||||SCAMP4||secretory carrier membrane protein 4|| | 0.793 | NM_079834 | 350 |
| EIF2B4 | ||EIF2B4||DKFZp586J0119||EIF2Bdelta||EIF2B-DELTA||EUKARYOTIC TRANSLATION INITIATION FACTOR 2B, DELTA||translation initiation factor eIF-2b delta subunit||eukaryotic translation initiation factor 2B, subunit 4 delta, 67 kDa||eukaryotic translation initiation factor 2B, subunit 4 delta | 0.759 | NM_172195 | 351 |

TABLE 1-continued

| | EE Transcriptome | | | |
|---|---|---|---|---|
| Common Name | Description | Fold Change | Genbank Accession number | SEQ ID NO |
| SLC12A4 | short isoform||eukaryotic translation initiation factor 2B, subunit 4 delta long isoform|| ||KCC1||SLC12A4||POTASSIUM-CHLORIDE COTRANSPORTER 1||SOLUTE CARRIER FAMILY 12 (POTASSIUM/CHLORIDE TRANSPORTER), MEMBER 4||solute carrier family 12 (potassium/chloride transporters), member 4|| | 0.758 | NM_005072 | 352 |
| MGC33607 | ||MGC33607||hypothetical protein MGC33607|| | 0.751 | NM_152775 | 353 |
| | ||*Homo sapiens* mRNA; cDNA DKFZp434B2115 (from clone DKFZp434B2115) | 0.74 | AL122093 | 354 |
| THEA | ||THEA||STARD14||THEM1||KIAA0707 BFIT1||THIOESTERASE, ADIPOSE-ASSOCIATED||thioesterase, adipose associated||BROWN FAT-INDUCIBLE THIOESTERASE||brown fat inducible thioesterase||START domain containing 14||thioesterase superfamily member 1||thioesterase, adipose associated isoform BFIT1||thioesterase, adipose associated isoform BFIT2|| | 0.729 | NM_147161 | 355 |
| SNX3 | ||SNX3||SNX3A||SDP3||MGC17570|| sorting nexin 3||sorting nexin 3A||sorting nexin 3 isoform a||sorting nexin 3 isoform b||sorting nexin 3 isoform c|| | 0.727 | NM_152828 | 356 |
| HIPK2 | ||HIPK2||PRO0593||EC 2.7.1.—||Homeodomain-interacting protein kinase 2||homeodomain interacting protein kinase 2|| | 0.708 | NM_014075 | 357 |
| PPP1CB | ||PP-1B||PPP1CD||MGC3672||3.1.3.16||PPP1CB|| protein phosphatase 1-delta||protein phosphatase 1-beta||serine/threonine protein phosphatase PP1-beta catalytic subunit||protein phosphatase 1, catalytic subunit, beta isoform||protein phosphatase 1, catalytic subunit, delta isoform||protein phosphatase 1, catalytic subunit, beta isoform 1|| | 0.708 | NM_002709 | 358 |
| SNX3 | ||SNX3||SNX3A||SDP3||MGC17570|| sorting nexin 3||sorting nexin 3A||sorting nexin 3 isoform a||sorting nexin 3 isoform b||sorting nexin 3 isoform c|| | 0.702 | NM_152828 | 359 |
| EYA3 | ||DKFZp686C132||EYA3||eyes absent 3 isoform a||eyes absent 3 isoform b||eyes absent homolog 3 (*Drosophila*)||EYES ABSENT, *DROSOPHILA*, HOMOLOG OF, 3|| | 0.699 | NM_001990 | 360 |
| ESTs | ESTs | 0.699 | AK025909 | 361 |
| | Data not found | 0.698 | U55055 | 362 |
| DPCD | ||DPCD||DKFZP566F084||DPCD protein||deleted in a mouse model of primary ciliary dyskinesia|| | 0.684 | NM_015448 | 363 |
| TIGA1 | ||TIGA1|| | 0.675 | NM_053000 | 364 |
| PABPC3 | ||PABPL3||PABPC3||PABP3||POLY-ADENYLATE-BINDING PROTEIN 3||poly(A)-binding protein-like 3||POLYADENYLATE-BINDING PROTEIN-LIKE 3||testis-specific poly(A)-binding protein (PABP)||POLYADENYLATE-BINDING PROTEIN, CYTOPLASMIC, 3||testis-specific poly(A)-binding protein 3||poly(A)-binding protein, | 0.663 | NM_030979 | 365 |

TABLE 1-continued

| | EE Transcriptome | | | |
|---|---|---|---|---|
| Common Name | Description | Fold Change | Genbank Accession number | SEQ ID NO |
| | cytoplasmic 3\|\|poly(A) binding protein, cytoplasmic 3\|\| | | | |
| C2orf4 | \|\|\|\|CGI-27\|\|C21orf19-like protein\|\| | 0.662 | NM_015955 | 366 |
| SYT15 | \|\|SYT15\|\|SYNAPTOTAGMIN 15\|\|synaptotagmin XV\|\| | 0.66 | NM_031912 | 367 |
| PABPC1 | \|\|PABPC1\|\|PABPL1\|\|PAB1\|\|PABP1\|\|POLY-ADENYLATE-BINDING PROTEIN 1\|\|POLY(A)-BINDING PROTEIN 1\|\|POLYADENYLATE-BINDING PROTEIN, CYTOPLASMIC, 1\|\|poly(A) binding protein, cytoplasmic 1\|\| | 0.658 | NM_002568 | 368 |
| RAB2 | \|\|RAB2A\|\|RAB2\|\|RAS-ASSOCIATED PROTEIN RAB2\|\|RAB2, member RAS oncogene family\|\| | 0.656 | NM_002865 | 369 |
| MGC33993 | \|\|MGC33993\|\|hypothetical protein MGC33993\|\| | 0.653 | NM_152737 | 370 |
| SC4MOL | \|\|SC4MOL\|\|DESP4\|\|ERG25\|\|sterol-C4-methyl oxidase-like\|\|STEROL C4-METHYLOXIDASE-LIKE\|\|C-4 methyl sterol\|\| | 0.652 | NM_006745 | 371 |
| KIAA1706 | \|\|KIAA1706\|\|KIAA1706 protein\|\| | 0.65 | NM_030636 | 372 |
| M-RIP | \|\|RHOIP3\|\|M-RIP\|\|KIAA0864\|\|Rho interacting protein 3\|\|myosin phosphatase-Rho interacting protein\|\|myosin phosphatase-Rho interacting protein isoform 1\|\|myosin phosphatase-Rho interacting protein isoform 2\|\| | 0.649 | NM_015134 | 373 |
| C3orf4 | \|\|C3orf4\|\|chromosome 3 open reading frame 4\|\| | 0.643 | NM_019895 | 374 |
| GAB2 | \|\|KIAA0571\|\|GAB2\|\|Grb2-associated binder 2\|\|GRB2-associated binding protein 2\|\|GRB2-associated binding protein 2 isoform a\|\|GRB2-associated binding protein 2 isoform b\|\| | 0.638 | NM_012296 | 375 |
| FLJ10156 | \|\|FLJ10156\|\|hypothetical protein FLJ10156\|\| | 0.636 | NM_019013 | 376 |
| FBXO10 | \|\|FBXO10\|\|F-box protein Fbx10\|\|F-box only protein 10\|\| | 0.636 | XM_291314 | 377 |
| DNASE1 | \|\|DNL1\|\|3.1.21.1\|\|DNASE1\|\|deoxyribonuclease I\|\|DNase I, LYSOSOMAL\|\| | 0.633 | NM_005223 | 378 |
| ROD1 | \|\|ROD1\|\|fission yeast differentiation regulator\|\|regulator of differentiation (in *S. pombe*) 1\|\|regulator of differentiation (in *S. pombi*) 1\|\|ROD1 regulator of differentiation 1 (*S. pombe*)\|\| | 0.633 | NM_005156 | 379 |
| ATP6AP1 | \|\|\|16A\|\|CF2\|\|ATP6AP1\|\|VATPS1\|\|ATP6S1\|\|Ac45\|\|ORF\|\|3.6.3.14\|\|XAP3\|\|ATP6IP1\|\|XAP-3\|\|H-ATPase subunit\|\|VACUOLAR ATPase SUBUNIT 1\|\|V-ATPase S1 accessory protein\|\|ATPase, H+ TRANSPORTING, LYSOSOMAL, SUBUNIT 1\|\|ATPase, H+ transporting, lysosomal interacting protein 1\|\|ATPase, H+ transporting, lysosomal accessory protein 1\|\|ATPase, H+ transporting, lysosomal accessory protein 1 precursor\|\|ATPase, H+ transporting, lysosomal (vacuolar proton pump), subunit 1\|\| | 0.63 | NM_001183 | 380 |
| USP13 | \|\|USP13\|\|IsoT-3\|\|ISOT3\|\|ISOPEPTIDASE T3\|\|UBIQUITIN-SPECIFIC PROTEASE 13\|\|ubiquitin specific protease 13 (isopeptidase T-3)\|\| | 0.628 | NM_003940 | 381 |
| CYB561 | \|\|CYB561\|\|CYTOCHROME b561\|\|cytochrome b-561\|\| | 0.628 | NM_001915 | 382 |
| PGM1 | \|\|5.4.2.2\|\|PGM1\|\|phosphoglucomutase 1\|\| | 0.619 | NM_002633 | 383 |

TABLE 1-continued

EE Transcriptome

| Common Name | Description | Fold Change | Genbank Accession number | SEQ ID NO |
|---|---|---|---|---|
| SAMD8 | \|\|SAMD8\|\|sterile alpha motif domain containing 8\|\| | 0.618 | NM_144660 | 384 |
| IGSF11 | \|\|IGSF11\|\|BTIGSF\|\|immunoglobulin superfamily, member 11\|\|BRAIN- AND TESTIS-SPECIFIC IMMUNOGLOBULIN SUPERFAMILY PROTEIN\|\| | 0.618 | NM_152538 | 385 |
| MAPK13 | \|\|SAPK4\|\|p38delta\|\|PRKM13\|\|p38-DELTA\|\|MAPK13\|\|mitogen-activated protein kinase 13\|\|stress-activated protein kinase 4\|\|PROTEIN KINASE, MITOGEN-ACTIVATED, 13\|\|mitogen-activated protein kinase p38 delta\|\| | 0.617 | NM_002754 | 386 |
| RABGAP1L | \|\|KIAA0471\|\|HHL\|\|expressed in hematopoietic cells, heart, liver\|\| | 0.615 | NM_014857 | 387 |
| QSCN6 | \|\|\|\|QSCN6\|\|quiescin Q6\|\| | 0.607 | NM_002826 | 388 |
| MRPL37 | \|\|MRPL37\|\|mitochondrial ribosomal protein L37\|\| | 0.599 | NM_016491 | 389 |
| RNF12 | \|\|RNF12\|\|RLIM\|\|ring finger protein 12\|\|PUTATIVE RING ZINC FINGER PROTEIN NY-REN-43 ANTIGEN\|\| | 0.597 | NM_183353 | 390 |
| DHCR24 | \|\|SELADIN1\|\|DHCR24\|\|seladin-1\|\|KIAA0018\|\|24-dehydrocholesterol reductase\|\|24-@DEHYDROCHOLESTEROL REDUCTASE\|\|SELECTIVE AD INDICATOR 1\|\|3 beta-hydroxysterol delta 24 reductase\|\| | 0.591 | NM_014762 | 391 |
| AOX1 | \|\|1.2.3.1\|\|AOH1\|\|AOX1\|\|aldehyde oxidase 1\|\| | 0.587 | NM_001159 | 392 |
| LOC340171 | \|\|\|\|Hypothetical LOC340171 (LOC340171), mRNA\|\| | 0.587 | BG928045 | 393 |
| LOC196264 | \|\|LOC196264\|\|hypothetical protein LOC196264\|\| | 0.585 | NM_198275 | 394 |
| FLJ32421 | \|\|FLJ32421\|\|hypothetical protein FLJ32421\|\| | 0.584 | NM_144695 | 395 |
| ZDHHC15 | \|\|ZDHHC15\|\|zinc finger, DHHC domain containing 15\|\| | 0.584 | NM_144969 | 396 |
| ZC3HDC5 | \|\|ZC3HDC5\|\|zinc finger CCCH type domain containing 5\|\| | 0.583 | XM_036115 | 397 |
| GAS7 | \|\|GAS7\|\|KIAA0394\|\|MGC1348\|\|growth arrest-specific 7\|\|growth arrest-specific 7 isoform a\|\|growth arrest-specific 7 isoform c\|\|growth arrest-specific 7 isoform b\|\| | 0.58 | NM_201433 | 398 |
|  |  | 0.576 | BF542107 | 399 |
| ELL2 | \|\|ELL2\|\|ELL-related RNA polymerase II, elongation factor\|\|elongation factor, RNA polymerase II, 2\|\| | 0.575 | NM_012081 | 400 |
| UNC13B | \|\|hmunc13\|\|UNC13B\|\|Unc13h2\|\|UNC13-LIKE\|\|unc-13-like (*C. elegans*)\|\|UNC13 (*C. elegans*)-like\|\|homolog of rat Munc13 (diacylglycerol-binding)\|\|unc-13 homolog B (*C. elegans*)\|\| | 0.575 | NM_006377 | 401 |
| SPRR3 | \|\|esophagin\|\|SPRR3\|\|small proline-rich protein 3\|\| | 0.569 | NM_005416 | 402 |
| CSTB | \|\|STFB\|\|CST6\|\|CPI-B\|\|PME\|\|CSTB\|\|liver thiol proteinase inhibitor\|\|cystatin B (stefin B)\|\| | 0.567 | NM_000100 | 403 |
| LOC199964 | \|\|LOC199964\|\|hypothetical protein LOC199964\|\| | 0.563 | NM_182532 | 404 |
| C17orf39 | \|\|MGC3048\|\|hypothetical protein MGC3048\|\| | 0.562 | NM_024052 | 405 |
| KRTHA2 | \|\|KRTHA2\|\|hHa2\|\|Ha-2\|\|keratin, hair, acidic, 2\|\|keratin, hair, acidic, 2\|\|hard keratin, type I, 2\|\|KERATIN, HARD, TYPE I, 2\|\|type I hair keratin 2\|\| | 0.561 | NM_002278 | 406 |
| TYRO3 | \|\|Brt\|\|Dtk\|\|RSE\|\|Sky\|\|BYK\|\|Tif\|\|TYRO3\|\|PROTEIN TYROSINE KINASE 3\|\|TYRO3 protein tyrosine kinase\|\|tyrosine-protein kinase receptor TYRO3 precursor\|\|Tyro3 | 0.56 | NM_006293 | 407 |

TABLE 1-continued

EE Transcriptome

| Common Name | Description | Fold Change | Genbank Accession number | SEQ ID NO |
|---|---|---|---|---|
| | protein tyrosine kinase (sea-related receptor tyrosine kinase)\|\| \|\|EPS8L1\|\|EPS8-like 1\|\| | | | |
| EPS8L1 | | 0.558 | NM_133180 | 408 |
| MAPK13 | \|\|SAPK4\|\|p38delta\|\|PRKM13\|\|p38-DELTA\|\|MAPK13\|\|mitogen-activated protein kinase 13\|\|stress-activated protein kinase 4\|\|PROTEIN KINASE, MITOGEN-ACTIVATED, 13\|\|mitogen-activated protein kinase p38 delta\|\| | 0.554 | NM_002754 | 409 |
| RNMT | \|\|RNMT\|\|RG7MT1\|\|KIAA0398\|\|RNA GUANINE-7-METHYLTRANSFERASE\|\|RNA (guanine-7-) methyltransferase\|\| | 0.553 | NM_003799 | 410 |
| NAP1L2 | \|\|NAP1L2\|\|MGC26243\|\|brain specific gene BPX\|\|nucleosome assembly protein 1-like 2\|\| | 0.551 | NM_021963 | 411 |
| RGS11 | \|\|RGS11\|\|RS11\|\|regulator of G-protein signalling 11\|\|REGULATOR OF G PROTEIN SIGNALING 11\|\|regulator of G-protein signalling 11 isoform 1\|\|regulator of G-protein signalling 11 isoform 2\|\| | 0.551 | NM_003834 | 412 |
| SRPRB | RAB6B | 0.55 | AK055102 | 413 |
| HTCD37 | \|\|\|\|HTCD37\|\|TcD37 homolog\|\| | 0.545 | NM_021222 | 414 |
| | | 0.544 | BX116062 | 415 |
| HIF1A | \|\|HIF1-ALPHA\|\|HIF1A\|\|MOP1\|\|HIF-1alpha\|\|ARNT interacting protein\|\|member of PAS superfamily 1\|\|hypoxia-inducible factor 1, alpha subunit isoform 2\|\|hypoxia-inducible factor 1, alpha subunit isoform 1\|\|hypoxia-inducible factor 1, alpha subunit (basic helix-loop-helix transcription factor)\|\| | 0.541 | NM_001530 | 416 |
| | | 0.53 | BG495068 | 417 |
| UBE2E2 | \|\|\|\|Hypothetical protein FLJ25157 (FLJ25157), mRNA\|\| | 0.529 | NM_152653 | 418 |
| MGC61716 | | 0.524 | NM_182501 | 419 |
| TPM4 | \|\|\|\|TPM4\|\|tropomyosin 4\|\| | 0.524 | NM_003290 | 420 |
| PIM1 | \|\|2.7.1.—\|\|PIM1\|\|pim-1 oncogene\|\|Oncogene PIM1\|\|ONCOGENE PIM 1\|\| | 0.523 | NM_002648 | 421 |
| FLJ32421 | \|\|FLJ32421\|\|hypothetical protein FLJ32421\|\| | 0.523 | NM_144695 | 422 |
| PINK1 | \|\|PINK1\|\|PTEN-INDUCED PUTATIVE KINASE 1\|\|PTEN induced putative kinase 1\|\| | 0.513 | NM_032409 | 423 |
| TOM1 | \|\|TOM1\|\|target of myb1 (chicken)\|\|target of myb 1\|\|target of myb1 (chicken) homolog\|\|TARGET OF MYB1, CHICKEN, HOMOLOG OF\|\| | 0.513 | NM_005488 | 424 |
| LOC142678 | \|\|skeletrophin\|\|LOC142678\|\| | 0.511 | NM_080875 | 425 |
| CAST | \|\|CAST\|\|MGC9402\|\|calpastatin\|\|heart-type calpastatin\|\|calpain inhibitor\|\|calpastatin isoform a\|\|calpastatin isoform b\|\|calpastatin isoform c\|\|calpastatin isoform d\|\|sperm BS-17 component\|\| | 0.51 | NM_173060 | 426 |
| NPR3 | \|\|NPR3\|\|ANPRC\|\|ATRIONATRIURETIC PEPTIDE RECEPTOR, TYPE C\|\|ATRIAL NATRIURETIC PEPTIDE CLEARANCE RECEPTOR\|\|natriuretic peptide receptor C/guanylate cyclase C (atrionatriuretic peptide receptor C)\|\| | 0.509 | NM_000908 | 427 |
| MYEOV | \|\|OCIM\|\|MYEOV\|\|myeloma overexpressed gene (in a subset of t(11; 14) positive multiple myelomas)\|\| | 0.509 | NM_138768 | 428 |

TABLE 1-continued

| | EE Transcriptome | | | |
|---|---|---|---|---|
| Common Name | Description | Fold Change | Genbank Accession number | SEQ ID NO |
| IMPA2 | \|\|IMPA2\|\|inositol(myo)-1(or 4)-monophosphatase 2\|\|MYO-INOSITOL MONOPHOSPHATASE 2\|\| | 0.508 | NM_014214 | 429 |
| FLJ13105 | | 0.507 | BF510602 | 430 |
| HIC | \|\|HIC\|\|I-mfa domain-containing protein\|\|I-mfa domain-containing protein isoform p40\|\| | 0.504 | NM_199072 | 431 |
| LOC55971 | \|\|LOC55971\|\|insulin receptor tyrosine kinase substrate\|\| | 0.504 | NM_018842 | 432 |
| DSC2 | \|\|desmocollin-3\|\|DSC2\|\|DGII/III\|\|DG2/3\|\|CDHF2\|\|desmocollin 2\|\|DSC3, FORMERLY\|\|desmosomal glycoprotein II/III\|\|DESMOCOLLIN 3, FORMERLY\|\|desmocollin 2 isoform Dsc2b preproprotein\|\|desmocollin 2 isoform Dsc2a preproprotein\|\| | 0.497 | NM_004949 | 433 |
| CES4 | \|\|\|\|CES1\|\|carboxylesterase 1 (monocyte/macrophage serine esterase 1)\|\| | 0.496 | NM_016280 | 434 |
| EPS8L1 | \|\|EPS8L1\|\|EPS8-like 1\|\| | 0.495 | NM_133180 | 435 |
| DKFZp434C0328 | \|\|DKFZp434C0328\|\|hypothetical protein DKFZp434C0328\|\| | 0.493 | NM_017577 | 436 |
| LOC375035 | \|\|LOC375035\|\|hypothetical protein LOC375035\|\| | 0.493 | NM_199344 | 437 |
| HIC | \|\|HIC\|\|I-mfa domain-containing protein\|\|I-mfa domain-containing protein isoform p40\|\| | 0.492 | NM_199072 | 438 |
| AK3 | \|\|2.7.4.10\|\|AK3\|\|AK4\|\|GTP:AMP phosphotransferase\|\|adenylate kinase 3\|\|adenylate kinase-3, mitochondrial\|\|ADENYLATE KINASE, MITOCHONDRIAL\|\|adenylate kinase isoenzyme 4, mitochondrial\|\| | 0.49 | NM_013410 | 439 |
| M6PR | \|\|CD-MPR\|\|M6PR\|\|MPR46\|\|SMPR\|\|Mr 46,000 Man6PR\|\|46-kDa mannose 6-phosphate receptor\|\|cation-dependent mannose-6-phosphate receptor precursor\|\|MANNOSE 6-PHOSPHATE RECEPTOR, CATION-DEPENDENT\|\|SMALL MANNOSE 6-PHOSPHATE RECEPTOR\|\|mannose-6-phosphate receptor (cation dependent)\|\| | 0.486 | NM_002355 | 440 |
| RPL18A | \|\|\|\|RPL18A\|\|ribosomal protein L18a\|\| | 0.486 | NM_000980 | 441 |
| EPS8L1 | \|\|EPS8L1\|\|EPS8-like 1\|\| | 0.485 | NM_133180 | 442 |
| AK3 | \|\|2.7.4.10\|\|AK3\|\|AK4\|\|GTP:AMP phosphotransferase\|\|adenylate kinase 3\|\|adenylate kinase-3, mitochondrial\|\|ADENYLATE KINASE, MITOCHONDRIAL\|\|adenylate kinase isoenzyme 4, mitochondrial\|\| | 0.481 | NM_013410 | 443 |
| SOCS6 | \|\|STAI4\|\|SOCS4\|\|CIS4\|\|SOCS6\|\|HSPC060\|\|SSI4\|\|STATI4\|\|STAT4\|\|STAT induced STAT inhibitor-4\|\|STAT-INDUCED STAT INHIBITOR 4\|\|cytokine-inducible SH2 protein 4\|\|suppressor of cytokine signaling 6\|\|suppressor of cytokine signaling 4\|\| | 0.48 | NM_004232 | 444 |
| C20orf161 | \|\|C20orf161\|\|chromosome 20 open reading frame 161\|\| | 0.48 | NM_033421 | 445 |
| C10orf57 | \|\|FLJ13263\|\|hypothetical protein FLJ13263\|\| | 0.479 | NM_025125 | 446 |
| USP13 | \|\|USP13\|\|IsoT-3\|\|ISOT3\|\|ISOPEPTIDASE T3\|\|UBIQUITIN-SPECIFIC PROTEASE 13\|\|ubiquitin specific protease 13 (isopeptidase T-3)\|\| | 0.479 | NM_003940 | 447 |
| FN5 | \|\|FN5\|\|FN5 protein\|\| | 0.478 | NM_020179 | 448 |
| VARS2L | \|\|DKFZP434L1435\|\|KIAA1885 protein\|\| | 0.474 | NM_020442 | 449 |

TABLE 1-continued

| | EE Transcriptome | | | |
|---|---|---|---|---|
| Common Name | Description | Fold Change | Genbank Accession number | SEQ ID NO |
| CDKN2B | ||p14_INK4B||p15(INK4B)||CDKN2B|| TP15||MTS2||p15_INK4B||CDK4B inhibitor||p14_CDK inhibitor||CDK inhibitory protein||p15 CDK inhibitor||multiple tumor suppressor 2||cyclin-dependent kinase 4 inhibitor B||cyclin-dependent kinase inhibitor 2B isoform 1||cyclin-dependent kinase inhibitor 2B isoform 2||cyclin-dependent kinase inhibitor 2B (p15, inhibits CDK4)||cyclin-dependent kinases 4 and 6 binding protein|| | 0.474 | NM_078487 | 450 |
| PR1 | ||PR1||voltage-dependent calcium channel gamma subunit-like protein|| | 0.473 | NM_183240 | 451 |
| ENC1 | ||PIG10||NRPB||ENC1||CCL28||ENC-1||TP53I10||NUCLEAR RESTRICTED PROTEIN/BRAIN||p53-INDUCED GENE 10||ECTODERMAL-NEURAL CORTEX 1||ectodermal-neural cortex (with BTB-like domain)||nuclear restricted protein, BTB domain-like (brain)||tumor protein p53 inducible protein 10|| | 0.472 | NM_003633 | 452 |
| HIST2H2BE | ||H2B.1||HIST2H2BE||H2B/q||H2BFQ|| GL105||histone 2, H2be||H2B histone family, member Q||HISTONE 2B FAMILY, MEMBER Q|| | 0.467 | NM_003528 | 453 |
| FLJ20674 | ||||FLJ20674||hypothetical protein FLJ20674|| | 0.463 | NM_019086 | 454 |
| CFLAR | ||CASH||FLIP||Casper||CFLAR||I-FLICE||FLAME1||FLAME-1||CLARP||USURPIN||MRIT||CASPASE-EIGHT-RELATED PROTEIN||FLICE INHIBITORY PROTEIN||MACH-RELATED INDUCER OF TOXICITY||FADD-LIKE ANTIAPOPTOTIC MOLECULE 1||CASP8 and FADD-like apoptosis regulator||CASP8- AND FADD-LIKE APOPTOSIS REGULATOR||FADD-like anti-apoptotic molecule; Inhibitor of FLICE; Caspase-related inducer of apoptosis; Caspase homolog; Caspase-like apoptosis regulatory protein|| | 0.462 | NM_003879 | 455 |
| PTN | ||HARP||HBNF||NEGF1||PTN||HBGF8|| heparin-binding growth-associated molecule||NEURITE OUTGROWTH-PROMOTING FACTOR, HEPARIN-BINDING||HEPARIN-BINDING GROWTH FACTOR 8||heparin affin regulatory protein||pleiotrophin (heparin binding growth factor 8, neurite growth-promoting factor 1)|| | 0.46 | NM_002825 | 456 |
| HOMER2 | ||cupidin||HOMER2||HOMER-2||Vesl-2||ACPD||homer homolog 2 (Drosophila)||HOMER 2B HOMER 2A||homer homolog 3 (Drosophila)||homer 2 isoform 1||homer, neuronal immediate early gene, 2|| | 0.46 | NM_004839 | 457 |
| MGLL | ||lysophospholipase-like||MGLL||HU-K5||monoglyceride lipase|| | 0.458 | NM_007283 | 458 |
| SLC16A9 | ||SLC16A9||solute carrier family 16 (monocarboxylic acid transporters), member 9|| | 0.458 | NM_194298 | 459 |
| FLJ20674 | ||||FLJ20674||hypothetical protein FLJ20674|| | 0.456 | NM_019086 | 460 |

TABLE 1-continued

EE Transcriptome

| Common Name | Description | Fold Change | Genbank Accession number | SEQ ID NO |
|---|---|---|---|---|
| MYOZ1 | ||MYOZ1||myozenin 1||CALSARCIN 2|| | 0.452 | NM_021245 | 461 |
| | | 0.445 | BC033124 | 462 |
| RAP2A | ||KREV||RAP2A||RbBP-30||RAS-RELATED PROTEIN 2A||RAP2A, member of RAS oncogene family||RAP2, member of RAS oncogene family (K-rev)|| | 0.439 | NM_021033 | 463 |
| ELL2 | ||ELL2||ELL-related RNA polymerase II, elongation factor||elongation factor, RNA polymerase II, 2|| | 0.431 | NM_012081 | 464 |
| WASL | ||MGC48327||N-WASP||WASL||Wiskott-Aldrich syndrome-like||Wiskott-Aldrich syndrome gene-like protein||neural Wiskott-Aldrich syndrome protein|| | 0.427 | NM_003941 | 465 |
| HIC | ||HIC||I-mfa domain-containing protein||I-mfa domain-containing protein isoform p40|| | 0.426 | NM_199072 | 466 |
| MGC61716 | *Homo sapiens* cDNA FLJ30912 fis, clone FEBRA2006346 | 0.426 | NM_182501 | 467 |
| PTP4A1 | ||PTP4A1||PRL1||PTPCAAX1||PTP(CAAX) ||PRL-1||HH72||Protein tyrosine phosphatase IVA1||PHOPHATASE OF REGENERATING LIVER 1||PROTEIN-TYROSINE PHOSPHATASE, TYPE 4A, 1||protein tyrosine phosphatase type IVA, member 1|| | 0.424 | NM_003463 | 468 |
| GP1BB | ||GP1BB||CD42c||GP Ib, BETA SUBUNIT||glycoprotein Ib beta polypeptide precursor||glycoprotein Ib (platelet), beta polypeptide||PLATELET GLYCOPROTEIN Ib, BETA POLYPEPTIDE||GLYCOPROTEIN Ib, PLATELET, BETA POLYPEPTIDE|| | 0.423 | NM_000407 | 469 |
| PELI1 | ||PELI1||pellino homolog 1 (*Drosophila*)|| | 0.423 | NM_020651 | 470 |
| PRKWNK1 | ||PHA2C||PRKWNK1||PROTEIN KINASE, LYSINE-DEFICIENT 1||KDP PSEUDOHYPOALDOSTERONISM, TYPE IIC||protein kinase, lysine deficient 1|| | 0.414 | NM_018979 | 471 |
| AMFR | ||RNF45||GP78||AMFR||autocrine motility factor receptor||autocrine motility factor receptor isoform a||autocrine motility factor receptor isoform b|| | 0.408 | NM_001144 | 472 |
| HPSE | ||heparanase||HSE1||HPSE||HPSE1|| HPR1||heparanase-1||HPA|| | 0.403 | NM_006665 | 473 |
| ST7L | | 0.402 | AK128799 | 474 |
| CYP2C18 | ||CYP2C18||1.14.14.1||P450IIC17|| P450-6B/29C||CYP2C17||CPCI||microsomal monooxygenase||flavoprotein-linked monooxygenase||CYTOCHROME P450, SUBFAMILY IIC, POLYPEPTIDE 18||cytochrome P450, family 2, subfamily C, polypeptide 18||cytochrome P450, subfamily IIC (mephenytoin 4-hydroxylase), polypeptide 17||cytochrome P450, subfamily IIC (mephenytoin 4-hydroxylase), polypeptide 18|| | 0.402 | NM_000772 | 475 |
| ITCH | ||ITCH||AIP4||NAPP1||ATROPHIN-1-INTERACTING PROTEIN 4||NFE2-ASSOCIATED POLYPEPTIDE 1||ITCHY, MOUSE, HOMOLOG OF||itchy homolog E3 ubiquitin protein ligase (mouse)|| | 0.396 | NM_031483 | 476 |

TABLE 1-continued

EE Transcriptome

| Common Name | Description | Fold Change | Genbank Accession number | SEQ ID NO |
|---|---|---|---|---|
| PPP2R2C | \|\|PPP2R2C\|\|PR52\|\|IMYPNO1\|\|MGC33570\|\|PP2A, subunit B, PR55-gamma isoform\|\|PP2A, subunit B, B55-gamma isoform\|\|PP2A, subunit B, R2-gamma isoform\|\|PP2A, subunit B, B-gamma isoform\|\|protein phosphatase 2A1 B gamma subunit\|\|phosphoprotein phosphatase 2A BR gamma regulatory chain\|\|PROTEIN PHOSPHATASE 2A, REGULATORY SUBUNIT B, GAMMA ISOFORM\|\|gamma isoform of regulatory subunit B55, protein phosphatase 2 isoform b\|\|Serine/threonine protein phosphatase 2A, 55 KDA regulatory subunit B, gamma isoform\|\|gamma isoform of regulatory subunit B55, protein phosphatase 2 isoform a\|\|protein phosphatase 2 (formerly 2A), regulatory subunit B (PR 52), gamma isoform\|\| | 0.392 | NM_020416 | 477 |
| CCDC6 | \|\|CCDC6\|\|TPC\|\|H4 GENE\|\|D10S170/H4 FUSION GENE\|\|TRANSFORMING SEQUENCE, THYROID 1\|\|coiled-coil domain containing 6\|\|TST1 PTC1 CHIMERIC ONCOGENE\|\| | 0.392 | NM_005436 | 478 |
| UACA | \|\|UACA\|\|uveal autoantigen with coiled-coil domains and ankyrin repeats\|\| | 0.391 | NM_018003 | 479 |
| C20orf161 | \|\|C20orf161\|\|chromosome 20 open reading frame 161\|\| | 0.389 | NM_033421 | 480 |
|  |  | 0.385 | AK024250 | 481 |
| DPCR1 | \|\|DPCR1\|\|PBLT\|\|PANBRONCHIOLITIS, DIFFUSE\|\|diffuse panbronchiolitis critical region 1\|\| | 0.384 | NM_080870 | 482 |
| FLJ39501 | \|\|FLJ39501\|\|hypothetical protein FLJ39501\|\| | 0.382 | NM_173483 | 483 |
| PFN2 | \|\|D3S1319E\|\|PFN2\|\|profilin-2\|\|PFL\|\|profilin 2\|\|profilin 2 isoform a\|\|profilin 2 isoform b\|\| | 0.381 | NM_053024 | 484 |
| C10orf57 | \|\|FLJ13263\|\|hypothetical protein FLJ13263\|\| | 0.376 | NM_025125 | 485 |
| GSTA4 | \|\|GSTA4\|\|GSTA4-4\|\|2.5.1.18\|\|GTA4\|\|GST class-alpha\|\|glutathione S-aralkyltransferase A4\|\|S-(hydroxyalkyl)glutathione lyase A4\|\|GLUTATHIONE S-TRANSFERASE, ALPHA-4\|\|glutathione transferase A4-4\|\|glutathione S-transferase A4\|\|glutathione S-aryltransferase A4\|\|glutathione S-alkyltransferase A4\|\|glutathione S-transferase, alpha 4\|\| | 0.376 | NM_001512 | 486 |
| DHRS1 | \|\|DHRS1\|\|dehydrogenase/reductase (SDR family) member 1\|\| | 0.359 | NM_138452 | 487 |
| SLC7A5 | \|\|SLC7A5\|\|MPE16\|\|D16S469E\|\|CD98\|\|LAT1\|\|4F2 light chain\|\|Membrane protein E16\|\|L-TYPE AMINO ACID TRANSPORTER 1\|\|Solute carrier family 7, member 5\|\|solute carrier family 7 (cationic amino acid transporter, y+ system), member 5\|\| | 0.358 | NM_003486 | 488 |
| LTB4DH | \|\|LTB4DH\|\|MGC34943\|\|leukotriene B4 12-hydroxydehydrogenase\|\|NADP-dependent leukotriene B4 12-hydroxydehydrogenase\|\| | 0.358 | NM_012212 | 489 |

TABLE 1-continued

| | EE Transcriptome | | | |
|---|---|---|---|---|
| Common Name | Description | Fold Change | Genbank Accession number | SEQ ID NO |
| SDR-O | \|\|SDR-O\|\|orphan short-chain dehydrogenase/reductase\|\| | 0.358 | NM_148897 | 490 |
| SMPDL3A | \|\|FLJ20177\|\|yR36GH4.1\|\|ASM3A\|\|0610010C24Rik\|\|SMPDL3A\|\|ASML3a\|\|sphingomyelin phosphodiesterase, acid-like 3A\|\|acid sphingomyelinase-like phosphodiesterase 3A\|\| | 0.357 | NM_006714 | 491 |
| DEPDC6 | \|\|DEPDC6\|\|DEP domain containing 6\|\| | 0.356 | NM_022783 | 492 |
| CAP2 | \|\|2810452G09Rik\|\|CAP2\|\|adenylyl cyclase-associated protein 2\|\|CAP, adenylate cyclase-associated protein, 2 (yeast)\|\| | 0.355 | NM_006366 | 493 |
| TUBB | \|\|M40\|\|TUBB\|\|tubulin, beta polypeptide\|\| | 0.355 | NM_001069 | 494 |
| SLC16A6 | \|\|MCT6\|\|SLC16A6\|\|monocarboxylate transporter 6\|\|solute carrier family 16, member 6\|\|SOLUTE CARRIER FAMILY 16 (MONOCARBOXYLIC ACID TRANSPORTER), MEMBER 6\|\|solute carrier family 16 (monocarboxylic acid transporters), member 6\|\| | 0.353 | NM_004694 | 495 |
| FLJ13910 | \|\|FLJ13910\|\|hypothetical protein FLJ13910\|\| | 0.348 | NM_022780 | 496 |
| TMOD3 | \|\|UTMOD\|\|TMOD3\|\|TROPOMODULIN, UBIQUITOUS\|\|tropomodulin 3 (ubiquitous)\|\| | 0.346 | NM_014547 | 497 |
| PHGDH | \|\|3PGDH\|\|PHGDH\|\|PDG\|\|PGAD\|\|SERA\|\|MGC3017\|\|3-@PHOSPHOGYLCERATE DEHYDROGENASE\|\|3-phosphoglycerate dehydrogenase\|\|phosphoglycerate dehydrogenase\|\| | 0.343 | NM_006623 | 498 |
| ARG2 | \|\|ARG2\|\|3.5.3.1\|\|A-II\|\|kidney arginase\|\|nonhepatic arginase\|\|L-arginine amidinohydrolase\|\|L-arginine ureahydrolase\|\|ARGINASE II\|\|arginase, type II\|\|arginase, type II precursor\|\| | 0.334 | NM_001172 | 499 |
| NUCB2 | \|\|NUCB2\|\|NEFA\|\|nucleobindin 2\|\| | 0.331 | NM_005013 | 500 |
| SPRR2B | \|\|SPR-2B\|\|SPRR2B\|\|Small proline-rich protein 2B\|\| | 0.331 | NM_006945 | 501 |
| NHLH2 | \|\|NSCL2\|\|NHLH2\|\|HEN2\|\|NEURONAL SCL-LIKE PROTEIN 2\|\|nescient helix loop helix 2\|\| | 0.329 | NM_005599 | 502 |
| AMACR | \|\|AMACR\|\|5.1.99.4\|\|ALPHA-METHYLACYL-CoA RACEMASE\|\|AMACR DEFICIENCY\|\|AMACR ALPHA-METHYLACYL-CoA RACEMASE DEFICIENCY\|\|alpha-methylacyl-CoA racemase isoform 1\|\|alpha-methylacyl-CoA racemase isoform 2\|\| | 0.328 | NM_014324 | 503 |
| FLJ40432 | \|\|FLJ40432\|\|hypothetical protein FLJ40432\|\| | 0.314 | NM_152523 | 504 |
| PRKWNK1 | \|\|PHA2C\|\|PRKWNK1\|\|PROTEIN KINASE, LYSINE-DEFICIENT 1\|\|KDP PSEUDOHYPOALDOSTERONISM, TYPE IIC\|\|protein kinase, lysine deficient 1\|\| | 0.302 | NM_018979 | 505 |
| TP53I3 | \|\|TP53I3\|\|PIG3\|\|quinone oxidoreductase homolog\|\|p53-induced gene 3 protein\|\|tumor protein p53 inducible protein 3\|\| | 0.3 | NM_004881 | 506 |
| CST6 | \|\|CST6\|\|cystatin 6\|\|cystatin E/M\|\|CYSTATIN M/E\|\|cystatin M precursor\|\| | 0.3 | NM_001323 | 507 |
| ZNF101 | \|\|ZNF101\|\|zinc finger protein 101\|\| | 0.29 | NM_033204 | 508 |
| FLJ25179 | \|\|FLJ25179\|\|hypothetical protein FLJ25179\|\| | 0.286 | NM_144670 | 509 |

TABLE 1-continued

EE Transcriptome

| Common Name | Description | Fold Change | Genbank Accession number | SEQ ID NO |
|---|---|---|---|---|
| RFK | ||FLJ11149||riboflavin kinase|| | 0.282 | NM_018339 | 510 |
| AKR1C3 | ||HA1753||1.1.1.188||DD3||hluPGFS|| HSD17B5||1.3.1.20||1.1.1.213|| AKR1C3||KIAA0119||HAKRB||HAKRe|| trans-1,2-dihydrobenzene-1,2-diol dehydrogenase||chlordecone reductase homolog||dihydrodiol dehydrogenase 3||prostaglandin F synthase||ALDO-KETO REDUCTASE B||3-@ALPHA-HYDROXYSTEROID DEHYDROGENASE, TYPE II||hydroxysteroid (17-beta) dehydrogenase 5||type IIb 3-alpha hydroxysteroid dehydrogenase||aldo-keto reductase family 1, member C3 (3-alpha hydroxysteroid dehydrogenase, type II)|| | 0.281 | NM_003739 | 511 |
| AKR1C1 | ||1.1.1.213||2-ALPHA-HSD||1.3.1.20||20-ALPHA-HSD||MGC8954||H-37||HAKRC||MBAB||C9||DDH1||AKR1C1|| trans-1,2-dihydrobenzene-1,2-diol dehydrogenase||chlordecone reductase homolog||aldo-keto reductase C||20 alpha-hydroxysteroid dehydrogenase||hepatic dihydrodiol dehydrogenase||dihydrodiol dehydrogenase isoform DD1||type II 3-alpha-hydroxysteroid dehydrogenase||DIHYDRODIOL DEHYDROGENASE, TYPE I||ALDO-KETO REDUCTASE FAMILY 1, MEMBER 1||aldo-keto reductase family 1, member C1 (dihydrodiol dehydrogenase 1; 20-alpha (3-alpha)-hydroxysteroid dehydrogenase)|| | 0.281 | NM_001353 | 512 |
| NQO1 | ||NMORI||diaphorase-4||NQO1||QR1||DTD||DHQU||NMOR1|| DIA4||DIAPHORASE 4||NAD(P)H dehydrogenase, quinone 1||diaphorase (NADH/NADPH) (cytochrome b-5 reductase)||NAD(P)H:menadione oxidoreductase 1, dioxin-inducible 1||NAD(P)H menadione oxidoreductase 1, dioxin-inducible|| | 0.28 | NM_000903 | 513 |
| LOC283824 | ||LOC283824||hypothetical protein LOC283824|| | 0.279 | BX647541 | 514 |
| C6orf56 | ||C6orf56||KIAA0680||KIAA0680 gene product||chromosome 6 open reading frame 56|| | 0.268 | NM_014721 | 515 |
| FAM43A | ||FLJ90022||hypothetical protein FLJ90022|| | 0.263 | NM_153690 | 516 |
| SH3GL3 | ||EEN-B2||SH3D2C||SH3GL3||SH3p13||HsT19371|| CNSA3||ENDOPHILIN A3||SH3-domain GRB2-like 3||SH3 DOMAIN, GRB2-LIKE, 3|| | 0.26 | NM_003027 | 517 |
| AKR1C1 | ||1.1.1.213||2-ALPHA-HSD||1.3.1.20||20-ALPHA-HSD||MGC8954||H-37||HAKRC||MBAB||C9||DDH1||AKR1C1|| trans-1,2-dihydrobenzene-1,2-diol dehydrogenase||chlordecone reductase homolog||aldo-keto reductase C||20 alpha-hydroxysteroid dehydrogenase||hepatic dihydrodiol dehydrogenase||dihydrodiol dehydrogenase isoform DD1||type II 3-alpha-hydroxysteroid | 0.257 | NM_001353 | 518 |

TABLE 1-continued

EE Transcriptome

| Common Name | Description | Fold Change | Genbank Accession number | SEQ ID NO |
|---|---|---|---|---|
| AKR1C2 | dehydrogenase\|\|DIHYDRODIOL DEHYDROGENASE, TYPE II\|\|ALDO-KETO REDUCTASE FAMILY 1, MEMBER 1\|\|aldo-keto reductase family 1, member C1 (dihydrodiol dehydrogenase 1; 20-alpha (3-alpha)-hydroxysteroid dehydrogenase)\|\| \|\|BABP\|\|DD2\|\|1.3.1.20\|\|HBAB\|\|1.1.1.213\|\| HAKRD\|\|MCDR2\|\|AKR1C2\|\|DDH2\|\| AKR1C-pseudo\|\|pseudo-chlordecone reductase\|\|trans-1,2-dihydrobenzene-1,2-diol dehydrogenase\|\|chlordecone reductase homolog\|\|ALDO-KETO REDUCTASE D\|\|3-@ALPHA-HYDROXYSTEROID DEHYDROGENASE, TYPE III\|\|type III 3-alpha-hydroxysteroid dehydrogenase\|\|DIHYDRODIOL DEHYDROGENASE, TYPE II\|\|type II dihydrodiol dehydrogenase\|\|aldo-keto reductase family 1, member C2 (dihydrodiol dehydrogenase 2; bile acid binding protein; 3-alpha hydroxysteroid dehydrogenase, type III)\|\| | 0.256 | NM_001354 | 519 |
| C20orf161 | \|\|C20orf161\|\|chromosome 20 open reading frame 161\|\| | 0.255 | NM_033421 | 520 |
| ACPP | \|\|3.1.3.2\|\|ACPP\|\|PAP\|\|acid phosphatase, prostate\|\|PHOSPHATASE, PROSTATE-SPECIFIC ACID\|\|prostatic acid phosphatase precursor\|\| | 0.254 | NM_001099 | 521 |
| AKR1C2 | \|\|BABP\|\|DD2\|\|1.3.1.20\|\|HBAB\|\|1.1.1.213\|\| HAKRD\|\|MCDR2\|\|AKR1C2\|\|DDH2\|\| AKR1C-pseudo\|\|pseudo-chlordecone reductase\|\|trans-1,2-dihydrobenzene-1,2-diol dehydrogenase\|\|chlordecone reductase homolog\|\|ALDO-KETO REDUCTASE D\|\|3-@ALPHA-HYDROXYSTEROID DEHYDROGENASE, TYPE III\|\|type III 3-alpha-hydroxysteroid dehydrogenase\|\|DIHYDRODIOL DEHYDROGENASE, TYPE II\|\|type II dihydrodiol dehydrogenase\|\|aldo-keto reductase family 1, member C2 (dihydrodiol dehydrogenase 2; bile acid binding protein; 3-alpha hydroxysteroid dehydrogenase, type III)\|\| | 0.251 | NM_001354 | 522 |
| ASAH3 | \|\|ASAH3\|\|N-acylsphingosine amidohydrolase (alkaline ceramidase) 3\|\| | 0.251 | NM_133492 | 523 |
| C9orf58 | \|\|C9orf58\|\|chromosome 9 open reading frame 58\|\| | 0.25 | NM_031426 | 524 |
| NQO1 | \|\|NMOR1\|\|diaphorase-4\|\|NQO1\|\|QR1\|\|DTD\|\|DHQU\|\|NMOR1\|\| DIA4\|\|DIAPHORASE 4\|\|NAD(P)H dehydrogenase, quinone 1\|\|diaphorase (NADH/NADPH) (cytochrome b-5 reductase)\|\|NAD(P)H:menadione oxidoreductase 1, dioxin-inducible 1\|\|NAD(P)H menadione oxidoreductase 1, dioxin-inducible\|\| | 0.248 | NM_000903 | 525 |
| S100A12 | \|\|MRP6\|\|CAAF1\|\|ENRAGE\|\|CGRP\|\|S100A12\|\| CALGRANULIN-RELATED PROTEIN\|\|S100 calcium-binding protein A12\|\|CALCIUM-BINDING PROTEIN IN AMNIOTIC | 0.247 | NM_005621 | 526 |

TABLE 1-continued

EE Transcriptome

| Common Name | Description | Fold Change | Genbank Accession number | SEQ ID NO |
|---|---|---|---|---|
| | FLUID\|\|EXTRACELLULAR NEWLY IDENTIFIED RAGE-BINDING PROTEIN\|\|S100 calcium binding protein A12 (calgranulin C)\|\| | 0.247 | BG218400 | 527 |
| PCSK5 | \|\|PC6A\|\|3.4.21.—\|\|PCSK5\|\|SPC6\|\|protease PC6\|\|proprotein convertase PC5\|\|subtilisin/kexin-like protease PC5\|\|prohormone convertase 5\|\|PROPROTEIN CONVERTASE, SUBTILISIN/KEXIN-TYPE, 5\|\|Proprotein convertase subtilisin/kexin type 5\|\|proprotein convertase subtilisin/kexin type 5 preproprotein\|\| | 0.246 | NM_006200 | 528 |
| EML1 | \|\|ELP79\|\|EMAPL\|\|EML1\|\|HuEMAP\|\|ECHINODERM MICROTUBULE-ASSOCIATED PROTEIN-LIKE 1\|\|echinoderm microtubule associated protein like 1\|\| | 0.244 | NM_004434 | 529 |
| NQO1 | \|\|NMOR1\|\|diaphorase-4\|\|NQO1\|\|QR1\|\|DTD\|\|DHQU\|\|NMOR1\|\|DIA4\|\|DIAPHORASE 4\|\|NAD(P)H dehydrogenase, quinone 1\|\|diaphorase (NADH/NADPH) (cytochrome b-5 reductase)\|\|NAD(P)H:menadione oxidoreductase 1, dioxin-inducible 1\|\|NAD(P)H menadione oxidoreductase 1, dioxin-inducible\|\| | 0.241 | NM_000903 | 530 |
| DPCR1 | \|\|DPCR1\|\|PBLT\|\|PANBRONCHIOLITIS, DIFFUSE\|\|diffuse panbronchiolitis critical region 1\|\| | 0.238 | NM_080870 | 531 |
| C6orf33 | \|\|MPRB\|\|LMPB1\|\|C6orf33\|\|MEMBRANE PROGESTIN RECEPTOR, BETA\|\|LYSOSOMAL MEMBRANE PROTEIN, BRAIN-EXPRESSED, 1\|\|chromosome 6 open reading frame 33\|\| | 0.232 | NM_133367 | 532 |
| BNIP3 | \|\|BNIP3\|\|BCL2/adenovirus E1B 19 kD-interacting protein 3\|\|BCL2/adenovirus E1B 19 kDa interacting protein 3\|\|BCL2/ADENOVIRUS E1B 19-KD PROTEIN-INTERACTING PROTEIN 3\|\|BCL2/adenovirus E1B 19 kD interacting protein 3\|\|BCL2/adenovirus E1B 19-kDa protein-interacting protein 3\|\| | 0.23 | NM_004052 | 533 |
| C6orf33 | \|\|MPRB\|\|LMPB1\|\|C6orf33\|\|MEMBRANE PROGESTIN RECEPTOR, BETA\|\|LYSOSOMAL MEMBRANE PROTEIN, BRAIN-EXPRESSED, 1\|\|chromosome 6 open reading frame 33\|\| | 0.228 | NM_133367 | 534 |
| FLJ40432 | \|\|FLJ40432\|\|hypothetical protein FLJ40432\|\| | 0.227 | NM_152523 | 535 |
| na | | 0.218 | XM_379456 | 536 |
| RDH12 | \|\|RDH12\|\|retinol dehydrogenase 12 (all-trans and 9-cis)\|\| | 0.216 | NM_152443 | 537 |
| C9orf58 | \|\|C9orf58\|\|chromosome 9 open reading frame 58\|\| | 0.215 | NM_031426 | 538 |
| MGC11324 | \|\|MGC11324\|\|hypothetical protein MGC11324\|\| | 0.212 | NM_032717 | 539 |
| PCSK5 | \|\|PC6A\|\|3.4.21.—\|\|PCSK5\|\|SPC6\|\|protease PC6\|\|proprotein convertase PC5\|\|subtilisin/kexin-like protease PC5\|\|prohormone convertase | 0.212 | NM_006200 | 540 |

TABLE 1-continued

EE Transcriptome

| Common Name | Description | Fold Change | Genbank Accession number | SEQ ID NO |
|---|---|---|---|---|
| | 5\|\|PROPROTEIN CONVERTASE, SUBTILISIN/KEXIN-TYPE, 5\|\|proprotein convertase subtilisin/kexin type 5\|\|proprotein convertase subtilisin/kexin type 5 preproprotein\|\| | | | |
| HSPA2 | \|\|HSPA1A\|\|heat shock-induced protein\|\|HEAT-SHOCK 70-KD PROTEIN 1A\|\|dnaK-type molecular chaperone HSP70-1\|\|HEAT-SHOCK PROTEIN, 70-KD, 1\|\|heat shock 70 kDa protein 1A\|\|heat shock 70 kD protein 1A\|\| | 0.211 | U56725 | 541 |
| ZNF426 | \|\|ZNF426\|\|zinc finger protein 426\|\| | 0.209 | NM_024106 | 542 |
| BPGM | | 0.205 | BG030612 | 543 |
| ME1 | \|\|MES\|\|1.1.1.40\|\|HUMNDME\|\|ME1\|\|pyruvic-malic carboxylase\|\|MALIC ENZYME, SOLUBLE\|\|Malic enzyme, cytoplasmic\|\|NADP-dependent malic enzyme\|\|cytosolic malic enzyme 1\|\|MALATE DEHYDROGENASE, NADP(+)-DEPENDENT, SOLUBLE\|\|malic enzyme 1, soluble\|\|MALIC ENZYME, NADP(+)-DEPENDENT, CYTOSOLIC\|\|malic enzyme 1, NADP(+)-dependent, cytosolic\|\| | 0.204 | NM_002395 | 544 |
| LOC284233 | | 0.202 | BC037172 | 545 |
| FNDC4 | \|\|FNDC4\|\|fibronectin type III domain containing 4\|\| | 0.2 | NM_022823 | 546 |
| ACPP | \|\|3.1.3.2\|\|ACPP\|\|PAP\|\|acid phosphatase, prostate\|\|PHOSPHATASE, PROSTATE-SPECIFIC ACID\|\|prostatic acid phosphatase precursor\|\| | 0.199 | NM_001099 | 547 |
| LOC56901 | \|\|LOC56901\|\|NADH:ubiquinone oxidoreductase MLRQ subunit homolog\|\| | 0.194 | NM_020142 | 548 |
| FLJ21511 | \|\|FLJ21511\|\|hypothetical protein FLJ21511\|\| | 0.191 | NM_025087 | 549 |
| PCSK5 | \|\|PC6A\|\|3.4.21.—\|\|PCSK5\|\|SPC6\|\|protease PC6\|\|proprotein convertase PC5\|\|subtilisin/kexin-like protease PC5\|\|prohormone convertase 5\|\|PROPROTEIN CONVERTASE, SUBTILISIN/KEXIN-TYPE, 5\|\|proprotein convertase subtilisin/kexin type 5\|\|proprotein convertase subtilisin/kexin type 5 preproprotein\|\| | 0.19 | NM_006200 | 550 |
| ME1 | \|\|MES\|\|1.1.1.40\|\|HUMNDME\|\|ME1\|\|pyruvic-malic carboxylase\|\|MALIC ENZYME, SOLUBLE\|\|Malic enzyme, cytoplasmic\|\|NADP-dependent malic enzyme\|\|cytosolic malic enzyme 1\|\|MALATE DEHYDROGENASE, NADP(+)-DEPENDENT, SOLUBLE\|\|malic enzyme 1, soluble\|\|MALIC ENZYME, NADP(+)-DEPENDENT, CYTOSOLIC\|\|malic enzyme 1, NADP(+)-dependent, cytosolic\|\| | 0.186 | NM_002395 | 551 |
| ZNF365 | \|\|ZNF365C\|\|ZNF365D\|\|KIAA0844\|\|ZNF365\|\|TALN\|\|talanin\|\|ZNF365B\|\|ZNF365 ZNF365A\|\|zinc finger protein 365\|\|zinc finger protein 365 isoform B\|\|zinc finger protein 365 isoform C\|\|zinc finger protein 365 isoform D\|\| | 0.173 | NM_199450 | 552 |

TABLE 1-continued

EE Transcriptome

| Common Name | Description | Fold Change | Genbank Accession number | SEQ ID NO |
|---|---|---|---|---|
| KRTAP3-2 | ||KRTAP3-2||keratin associated protein 3-2|| | 0.167 | NM_031959 | 553 |
| SYNPO2L | ||SYNPO2L||synaptopodin 2-like|| | 0.166 | NM_024875 | 554 |
| BNIP3 | ||BNIP3||BCL2/adenovirus E1B 19 kD-interacting protein 3||BCL2/adenovirus E1B 19 kDa interacting protein 3||BCL2/ADENOVIRUS E1B 19-KD PROTEIN-INTERACTING PROTEIN 3||BCL2/adenovirus E1B 19 kD interacting protein 3||BCL2/adenovirus E1B 19-kDa protein-interacting protein 3|| | 0.166 | NM_004052 | 555 |
| CRYAB | ||CTPP2||CRYAB||CRYSTALLIN, ALPHA-B||CRYSTALLIN, ALPHA-2||crystallin, alpha B||heat-shock 20 kD like-protein||CRYA2 CATARACT, POSTERIOR POLAR 2|| | 0.158 | NM_001885 | 556 |
| FLJ21511 | ||FLJ21511||hypothetical protein FLJ21511|| | 0.154 | NM_025087 | 557 |
| HIG2 | ||HIG2||hypoxia-inducible protein 2|| | 0.148 | NM_013332 | 558 |
| SYNPO2L | ||SYNPO2L||synaptopodin 2-like|| | 0.139 | NM_024875 | 559 |
| IGFL1 | ||APRG644||UNQ644|| | 0.138 | NM_198541 | 560 |
| FLJ40201 | ||FLJ40201||hypothetical protein FLJ40201|| | 0.129 | NM_152607 | 561 |
| ECG2 | ||ECG2||esophagus cancer-related gene-2|| | 0.128 | NM_032566 | 562 |
| ALOX12 | ||12(S)-lipoxygenase||12-@LIPOXYGENASE||1.13.11.31||ALOX12||LOG12||12@LO||ARACHIDONATE 12-OXIDOREDUCTASE||arachidonate 12-lipoxygenase|| | 0.105 | NM_000697 | 563 |
| EPB41L3 | ||DAL1||KIAA0987||EPB41L3||4.1B||DAL-1||NONERYTHROID PROTEIN 4.1, BRAIN TYPE||erythrocyte membrane protein band 4.1-like 3||differentially expressed in adenocarcinoma of the lung|| | 0.0956 | NM_012307 | 564 |
| SNX19 | ||KIAA0254||CHET8||SNX19||sorting nexin 19||KIAA0254 gene product|| | 0.0946 | NM_014758 | 565 |
| P11 | ||PRSS26-PENDING||P11||PP11||22 serine protease||26 serine protease||placental protein 11 precursor|| | 0.0934 | NM_006025 | 566 |
| CES4 | ||||CES1||carboxylesterase 1 (monocyte/macrophage serine esterase 1)|| | 0.0881 | NM_016280 | 567 |
| EPB41L3 | ||DAL1||KIAA0987||EPB41L3||4.1B||DAL-1||NONERYTHROID PROTEIN 4.1, BRAIN TYPE||erythrocyte membrane protein band 4.1-like 3||differentially expressed in adenocarcinoma of the lung|| | 0.0709 | NM_012307 | 568 |
| EPB41L3 | ||DAL1||KIAA0987||EPB41L3||4.1B||DAL-1||NONERYTHROID PROTEIN 4.1, BRAIN TYPE||erythrocyte membrane protein band 4.1-like 3||differentially expressed in adenocarcinoma of the lung|| | 0.0687 | NM_012307 | 569 |
| GYS2 | ||GYS2||2.4.1.11||LIVER GLYCOGEN SYNTHASE||GLYCOGEN SYNTHASE, LIVER||glycogen synthase 2 (liver)|| | 0.0662 | NM_021957 | 570 |
| CDA | ||3.5.4.5||CDA||CDD||cytidine deaminase|| | 0.0587 | NM_001785 | 571 |
| | | 0.0555 | BF514741 | 572 |
| | | 0.0387 | AK125406 | 573 |

TABLE 1-continued

EE Transcriptome

| Common Name | Description | Fold Change | Genbank Accession number | SEQ ID NO |
|---|---|---|---|---|
| CRISP3 | \|\|dJ442L6.3\|\|CRS3\|\|CRISP-3\|\|SGP28\|\|Aeg2\|\|CRISP3\|\|cysteine-rich secretory protein-3\|\|cysteine-rich secretory protein 3\|\|specific granule protein (28 kDa)\|\| | 0.0306 | NM_006061 | 574 |

TABLE 2

Patient characteristics[a]

| Patient | Sex | Age (year) | Esophageal Disease | Treatment | Maximum Eosinophil number/hpf | Expansion of basal layer | SPT/A[b] | SPT/F[b] | Allergic Disease[c] |
|---|---|---|---|---|---|---|---|---|---|
| 1 | M | 11 | NL | None | 0 | No | Unk | Unk | Unk |
| 2 | F | 9 | NL | None | 0 | No | 1 | 3 | Yes |
| 3 | F | 6 | NL | LTRA | 0 | No | Unk | Unk | Unk |
| 4 | F | 13 | NL | None | 0 | No | 0 | 0 | No |
| 5 | M | 10 | NL | None | 0 | No | Unk | Unk | Unk |
| 6 | F | 4 | NL | LTRA | 0 | No | Unk | Unk | Unk |
| 7 | M | 6 | CE | PPI | 0 | Yes | Unk | Unk | Unk |
| 8 | M | 17 | CE | PPI | 0 | Yes | Unk | Unk | Unk |
| 9 | F | 14 | CE | LTRA | 3 | Yes | 0 | 0 | No |
| 10 | F | 12 | CE | None | 3 | Yes | Unk | Unk | Unk |
| 11 | F | 11 | CE | LTRA + PPI | 6 | Yes | Unk | Unk | Unk |
| 12 | M | 11 | EE | PPI | 24 | Yes | 2 | 4 | Yes |
| 13 | F | 4 | EE | PPI | 25 | Yes | 0 | 0 | No |
| 14 | M | 15 | EE | None | 30 | Yes | 1 | 1 | Yes |
| 15 | M | 15 | EE | None | 31 | Yes | 2 | 0 | Yes |
| 16 | M | 13 | EE | PPI | 32 | Yes | 0 | 0 | No |
| 17 | M | 6 | EE | PPI | 40 | Yes | 3 | 1 | Yes |
| 18 | M | 13 | EE | LTRA | 42 | Yes | 4 | 4 | Yes |
| 19 | F | 16 | EE | LTRA + PPI | 50 | Yes | 0 | 0 | No |
| 20 | M | 15 | EE | None | 51 | Yes | 0 | 0 | No |
| 21 | M | 3 | EE | PPI | 56 | Yes | 1 | 4 | Yes |
| 22 | F | 14 | EE | PPI | 72 | Yes | 3 | 3 | Yes |
| 23 | M | 2 | EE | None | 83 | Yes | 0 | 4 | Yes |
| 24 | F | 4 | EE | PPI | 218 | Yes | 2 | 4 | Yes |

[a]Patient characteristics at the time the biopsy sample was obtained.
[b]The number of positive skin prick test to foods (SPT/F) or aeroallergens (SPT/A) are reported on a 0-4 scale as described in the Methods.
[c]History of past or present atopic dermatitis, allergic rhinitis, or asthma.
Abbreviations:
M, male;
F, female;
NL, normal;
CE, Chronic Esophagitis;
EE, Eosinophilic Esophagitis;
LTRA, Leukotriene Receptor Antagonist;
PPI, proton pump inhibitor;
Unk, unknown.

TABLE 3

Gene ontology of the upregulated genes in the EE transcript signature

| Classification | COUNT | % |
|---|---|---|
| Total upregulated | 344 | |
| CLASSIFIED (biological process) | 270 | 100 |
| RESPONSE TO PEST/PATHOGEN/PARASITE | 26 | 9.6 |
| RESPONSE TO STRESS | 30 | 11.1 |
| INFLAMMATORY RESPONSE | 13 | 4.8 |
| POSITIVE REGULATION OF I-KAPPAB KINASE/NF-KAPPAB CASCADE | 8 | 3 |
| RESPONSE TO WOUNDING | 14 | 5.2 |
| POSITIVE REGULATION OF SIGNAL TRANSDUCTION | 8 | 3 |
| CELL COMMUNICATION | 70 | 25.8 |
| SIGNAL TRANSDUCTION | 59 | 21.8 |
| RESPONSE TO BIOTIC STIMULUS | 49 | 18.1 |
| PROTEIN KINASE CASCADE | 12 | 4.4 |
| HUMORAL IMMUNE RESPONSE | 9 | 3.3 |
| IMMUNE RESPONSE | 44 | 16.2 |
| RESPONSE TO EXTERNAL STIMULUS | 54 | 19.9 |
| APOPTOSIS | 14 | 5.2 |
| CARBOXYLIC ACID BIOSYNTHESIS | 5 | 1.8 |
| ORGANIC ACID BIOSYNTHESIS | 5 | 1.8 |
| PROTEOLYSIS AND PEPTIDOLYSIS | 17 | 6.3 |
| ICOSANOID METABOLISM | 4 | 1.5 |

TABLE 3-continued

Gene ontology of the upregulated genes in the EE transcript signature

| Classification | COUNT | % |
|---|---|---|
| MONOCARBOXYLIC ACID TRANSPORT | 3 | 1.1 |
| CATABOLISM | 22 | 8.1 |
| PROTEIN CATABOLISM | 17 | 6.3 |
| COMPLEMENT ACTIVATION | 4 | 1.5 |
| CELL ADHESION | 17 | 6.3 |
| ANTIGEN PROCESSING, ENDOGENOUS ANTIGEN VIA MHC CLASS I | 3 | 1.1 |
| MACROMOLECULE CATABOLISM | 18 | 6.6 |
| FATTY ACID BIOSYNTHESIS | 4 | 1.5 |
| ICOSANOID BIOSYNTHESIS | 3 | 1.1 |
| FATTY ACID METABOLISM | 6 | 2.2 |
| BLOOD COAGULATION | 5 | 1.8 |
| HEMOSTASIS | 5 | 1.8 |
| CHOLESTEROL METABOLISM | 4 | 1.5 |
| LIPID METABOLISM | 13 | 4.8 |
| ANION TRANSPORT | 7 | 2.6 |
| STEROL METABOLISM | 4 | 1.5 |
| REGULATION OF BODY FLUIDS | 5 | 1.8 |
| CLASSIFIED (molecular function) | 271 | 100 |
| SIGNAL TRANSDUCER ACTIVITY | 60 | 22.1 |
| SCAVENGER RECEPTOR ACTIVITY | 5 | 1.8 |
| OXIDOREDUCTASE ACTIVITY, ACTING ON THE CH—NH2 GROUP OF DONORS | 4 | 1.5 |
| PEPTIDE TRANSPORTER ACTIVITY | 3 | 1.1 |
| PROTEIN BINDING | 37 | 13.7 |
| PEPTIDASE ACTIVITY | 16 | 5.9 |
| ENDOPEPTIDASE ACTIVITY | 13 | 4.8 |
| CHYMOTRYPSIN ACTIVITY | 6 | 2.2 |
| OBSOLETE MOLECULAR FUNCTION | 15 | 5.5 |
| TRYPSIN ACTIVITY | 6 | 2.2 |
| PROTEASOME ENDOPEPTIDASE ACTIVITY | 3 | 1.1 |
| GLYCOSAMINOGLYCAN BINDING | 5 | 1.8 |
| INTERLEUKIN RECEPTOR ACTIVITY | 3 | 1.1 |
| RECEPTOR ACTIVITY | 38 | 14 |
| INTERLEUKIN BINDING | 3 | 1.1 |
| ENZYME ACTIVATOR ACTIVITY | 6 | 2.2 |
| OLIGOPEPTIDE TRANSPORTER ACTIVITY | 2 | 0.7 |

The functional annotations are generated by subjecting the data to DAVID software with the GoCharts (gene ontology charts) functional algorithm. Analysis is based on biological processes and molecular functions.

TABLE 4

Gene ontology of the downregulated genes of the EE transcript signature

| Classification | COUNT | % |
|---|---|---|
| Total downregulated | 230 | |
| CLASSIFIED (biological process) | 180 | 100 |
| CARBOXYLIC ACID METABOLISM | 11 | 6.1 |
| ORGANIC ACID METABOLISM | 11 | 6.1 |
| METABOLISM | 75 | 41.7 |
| INTRACELLULAR SIGNALING CASCADE | 16 | 8.9 |
| FATTY ACID METABOLISM | 5 | 2.8 |
| ICOSANOID METABOLISM | 3 | 1.7 |
| MORPHOGENESIS | 16 | 8.9 |
| PROTEIN KINASE CASCADE | 6 | 3.3 |
| CLASSIFIED (molecular function) | 180 | 100 |
| CATALYTIC ACTIVITY | 63 | 35 |
| OXIDOREDUCTASE ACTIVITY, ACTING ON CH—OH GROUP OF DONORS | 6 | 3.3 |
| ENZYME INHIBITOR ACTIVITY | 8 | 4.4 |
| SERINE ESTERASE ACTIVITY | 3 | 1.7 |
| ACTIN BINDING | 7 | 3.9 |
| OXIDOREDUCTASE ACTIVITY | 16 | 8.9 |
| CARBOXYLESTERASE ACTIVITY | 3 | 1.7 |
| ENZYME REGULATOR ACTIVITY | 11 | 6.1 |
| CYTOSKELETAL PROTEIN BINDING | 7 | 3.9 |
| TRANS-1,2-DIHYDROBENZENE-1,2-DIOL DEHYDROGENASE ACTIVITY | 2 | 1.1 |
| HYDROLASE ACTIVITY, ACTING ON ESTER BONDS | 11 | 6.1 |
| ENDOPEPTIDASE INHIBITOR ACTIVITY | 5 | 2.8 |
| PROTEASE INHIBITOR ACTIVITY | 5 | 2.8 |
| CARBOXYLIC ACID TRANSPORTER ACTIVITY | 4 | 2.2 |
| ORGANIC ACID TRANSPORTER ACTIVITY | 4 | 2.2 |
| CYTOCHROME-B5 REDUCTASE ACTIVITY | 2 | 1.1 |
| POLY(A) BINDING | 2 | 1.1 |
| PHOSPHORIC MONOESTER HYDROLASE ACTIVITY | 6 | 3.3 |
| PHOSPHOPROTEIN PHOSPHATASE ACTIVITY | 5 | 2.8 |
| MAGNESIUM ION BINDING | 5 | 2.8 |

The functional annotations are generated by subjecting the data to DAVID software with the GoCharts (gene ontology charts) functional algorithm. Analysis is based on biological processes and molecular functions.

TABLE 5

Number of genes obtained using Welch and Student T-Test, Pearson correlation test and fold change filter.

| | fold change | | | |
|---|---|---|---|---|
| fold change | 2 | 3 | 5 | 10 |
| NLvs EE | 1146 | 382 | 124 | 42 |
| NLvs CE | 25 | 7 | 0 | 0 |

| | p value | | | |
|---|---|---|---|---|
| | 0.05 | 0.01 | 0.005 | 0.001 |
| NLvs EE | | | | |
| Welch T test | 9063 | 4183 | 3034 | 1527 |
| student T test | 7707 | 3283 | 2295 | 1017 |
| Welch T test + FDR | 1928 | 574 | 333 | 69 |
| student T test + FDR | 958 | 236 | 134 | 59 |
| NLvs CE | | | | |
| Welch T test | 1432 | 163 | 73 | 8 |
| student T test | 1618 | 216 | 105 | 8 |
| Welch T test + FDR | 0 | 0 | 0 | 0 |
| student T test + FRD | 0 | 0 | 0 | 0 |
| EE Atopic vs EE non-Atopic | | | | |
| Welch T test | 1403 | 200 | 90 | 13 |
| student T test | 1543 | 216 | 88 | 14 |
| Welch T test + FDR | 0 | 0 | 0 | 0 |
| student T test + FDR | 0 | 0 | 0 | 0 |
| EE female vs EE male | | | | |
| Welch T test | 4158 | 857 | 434 | 75 |
| student T test | 4185 | 691 | 298 | 49 |
| Welch T test + FDR | 1 | 1 | 1 | 1 |
| student T test + FDR | 8 | 5 | 5 | 5 |

| | p value | | | | |
|---|---|---|---|---|---|
| Pearson correlation | 0.05 | 0.01 | 0.005 | 0.001 | 0.0005 |
| Correlation to eosinophils | 6261 | 2757 | 1943 | 899 | 615 |
| Correlation to age | 2257 | 334 | 136 | 16 | 10 |

Abbreviation: False rate discovery correction (FDR); EE, Eosinophilic esophagitis; CE, Chronic esophagitis; NL, normal.

TABLE 6

Genes significantly different in EE and CE compared to NL

| Common Name | Description | Fold Increase in EE | Genbank Accession number |
|---|---|---|---|
| | | 2.432 | AK095791 |
| LOC132430 | | 2.047 | XR_000195 |
| ARRDC2 | \|\|CLONE24945\|\|PP2703\|\|ARRDC2\|\| arrestin domain containing 2\|\| | 1.887 | NM_015683 |
| FGF11 | \|\|FGF11\|\|MGC45269\|\|FHF3\|\|fibroblast growth factor 11\|\|fibroblast growth factor homologous factor 3\|\| | 1.868 | NM_004112 |
| DAPK2 | \|\|DRP-1\|\|DAPK2\|\|death-associated protein kinase 2\|\| | 1.695 | NM_014326 |
| SLCO3A1 | \|\|SLC21A11\|\|OATP-D\|\|SLCO3A1\|\|OATP3A1\|\|solute carrier organic anion transporter family, member 3A1\|\|solute carrier family 21 (organic anion transporter), member 11\|\| | 1.623 | NM_013272 |
| TCF4 | \|\|SEF2-1B\|\|TCF4\|\|E2-2\|\|ITF2\|\|transcription factor 4\|\|IMMUNOGLOBULIN TRANSCRIPTION FACTOR 2\|\|transcription factor 4 isoform b\|\|Transcription factor-4 (immunoglobulin transcription factor-2)\|\| | 1.547 | NM_003199 |
| MARVELD3 | \|\|LOC91862\|\|MRVLDC3\|\|MARVEL (membrane-associating) domain containing 3\|\|similar to RIKEN cDNA 1810006A16 gene\|\| | 1.517 | NM_052858 |
| EXT1 | | 1.507 | BX115875 |
| NF1 | \|\|NFNS\|\|WSS\|\|NF1\|\|VRNF\|\|Neurofibromin (neurofibromatosis, type I)\|\|VON RECKLINGHAUSEN DISEASE NEUROFIBROMIN\|\|neurofibromin 1 (neurofibromatosis, von Recklinghausen disease, Watson disease)\|\| | 1.506 | NM_000267 |
| BAT8 | \|\|Em:AF134726.3\|\|BAT8\|\|NG/G9a\|\|NG36 protein\|\|ankyrin repeat-containing protein\|\|HLA-B-ASSOCIATED TRANSCRIPT 8\|\|G9A histone methyltransferase\|\|HLA-B associated transcript 8\|\|HLA-B associated transcript 8 BAT8 isoform a\|\|HLA-B associated transcript 8 BAT8 isoform b\|\| | 1.45 | NM_006709 |
| SMC5L1 | | 1.332 | BC035661 |
| KLK1 | \|\|Klk6\|\|KLKR\|\|3.4.21.35\|\|KLK1\|\|KALLIKREIN, RENAL/PANCREATIC/SALIVARY\|\|tissue kallikrein\|\|renal/pancreas/salivary kallikrein\|\|kallikrein 1 preproprotein\|\|kallikrein 1, renal/pancreas/salivary\|\|glandular kallikrein 1\|\|kallikrein serine protease 1\|\| | 1.28 | NM_002257 |
| C21orf51 | \|\|C21orf51\|\|chromosome 21 open reading frame 51\|\| | 1.263 | NM_058182 |
| INSR | \|\|INSR\|\|insulin receptor\|\|IRAN, TYPE A\|\|DIABETES MELLITUS, INSULIN-RESISTANT, WITH ACANTHOSIS NIGRICANS, TYPE A\|\|INSR INSULIN RECEPTOR, DEFECT IN, WITH INSULIN-RESISTANT DIABETES MELLITUS AND ACANTHOSIS NIGRICANS\|\| | 1.25 | NM_000208 |
| | \|\|\|\|LOC400988 (LOC400988), mRNA\|\| | 1.225 | BC039374 |
| PARC | \|\|H7AP1\|\|KIAA0708\|\|PARC\|\|UbcH7-associated protein 1\|\|p53-ASSOCIATED PARKIN-LIKE CYTOPLASMIC PROTEIN\|\| | 1.206 | NM_015089 |
| | | 1.192 | BC033938 |
| SLC35C2 | \|\|SLC35C2\|\|solute carrier family 35, member C2\|\| | 1.145 | NM_173179 |
| ARHGEF12 | \|\|ARHGEF12\|\|PRO2792\|\|KIAA0382\|\| LARG LARG/MLL FUSION | 0.884 | NM_015313 |

TABLE 6-continued

Genes significantly different in EE and CE compared to NL

| Common Name | Description | Fold Increase in EE | Genbank Accession number |
|---|---|---|---|
| | GENE||leukemia-associated rho guanine nucleotide exchange factor||RHO GUANINE NUCLEOTIDE EXCHANGE FACTOR 12||Rho guanine nucleotide exchange factor (GEF) 12||RHO GUANINE NUCLEOTIDE EXCHANGE FACTOR, LEUKEMIA-ASSOCIATED LEUKEMIA-ASSOCIATED RHO GEF|| | | |
| | ||||Similar to hypothetical protein 4932411E22 (LOC342600), mRNA|| | 0.869 | XM_292624 |
| MGC22014 | ||MGC22014||hypothetical protein MGC22014|| | 0.864 | AB007861 |
| MTA3 | | 0.861 | AW594033 |
| MCF2L | ||ARHGEF14||KIAA0362||FLJ12122||MCF2L||OST||DBL's big sister||MCF2 transforming sequence-like protein||guanine nucleotide exchange factor DBS||MCF.2 cell line derived transforming sequence-like|| | 0.851 | NM_024979 |
| SLC25A30 | ||LOC253512||hypothetical protein LOC253512|| | 0.844 | AL832206 |
| TARP | | 0.843 | AK026401 |
| | | 0.842 | BC044912 |
| | | 0.84 | BM723387 |
| CXorf6 | ||CG1||CXorf6||F18 GENE||chromosome X open reading frame 6|| | 0.831 | NM_005491 |
| PBX3 | | 0.823 | AK027170 |
| RQCD1 | ||CNOT9||RQCD1||RCD1+||protein involved in sexual development||rcd1 (required for cell differentiation, S. pombe) homolog 1||RCD1 required for cell differentiation1 homolog (S. pombe)|| | 0.811 | NM_005444 |
| TBN | ||TBN||taube nuss homolog (mouse)|| | 0.81 | NM_138572 |
| DNCH1 | ||DNCH1||HL-3||KIAA0325||Dnchc1||p22||DYHC||DHC1a||DNCL||DNECL||dynein, cytoplasmic-like||DYNEIN HEAVY POLYPEPTIDE, CYTOPLASMIC||dynein heavy chain, cytosolic||dynein, cytoplasmic, heavy polypeptide 1||DYNEIN, CYTOPLASMIC, HEAVY CHAIN 1|| | 0.802 | NM_001376 |
| | ||||LOC388952 (LOC388952), mRNA|| | 0.793 | XM_373986 |
| LOC115110 | | 0.78 | AL359943 |
| SYNE2 | ||DKFZP434H2235||Nesprin-2||SYNE2||NUANCE||SYNE-2||KIAA1011||nesprin 2||nucleus and actin connecting element||SYNAPTIC NUCLEAR ENVELOPE PROTEIN 2||spectrin repeat containing, nuclear envelope 2||NUCLEAR ENVELOPE SPECTRIN REPEAT PROTEIN 2||synaptic nuclei expressed gene 2 isoform b||synaptic nuclei expressed gene 2 isoform c||synaptic nuclei expressed gene 2 isoform d||synaptic nuclei expressed gene 2 isoform e||synaptic nuclei expressed gene 2 isoform a|| | 0.779 | NM_015180 |
| YWHAZ | ||KCIP-1||14-3-3-ZETA||YWHAZ||phospholipase A2||14-3-3 zeta||BRAIN PROTEIN 14-3-3, ZETA ISOFORM||protein kinase C inhibitor protein-1||TYROSINE 3-MONOOXYGENASE/TRYPTOPHAN 5-MONOOXYGENASE ACTIVATION | 0.654 | NM_145690 |

TABLE 6-continued

Genes significantly different in EE and CE compared to NL

| Common Name | Description | Fold Increase in EE | Genbank Accession number |
|---|---|---|---|
| | PROTEIN, ZETA ISOFORM‖tyrosine 3-monooxygenase/tryptophan 5-monooxygenase activation protein, zeta polypeptide‖tyrosine 3/tryptophan 5-monooxygenase activation protein, zeta polypeptide‖ | 0.653 | BE562274 |
| | | 0.65 | BM993105 |
| MYOZ1 | ‖MYOZ1‖myozenin 1‖CALSARCIN 2‖ | 0.452 | NM_021245 |

TABLE 7

Genotype and allele frequencies of the SNP + 2496 of the eotaxin-3 gene in EE patients and non EE patients.

| SNP + 2496 | Patients with EE (n = 96) | Normal Controls (n = 177) | Odds ratio (95% CI) | P-value |
|---|---|---|---|---|
| TT | 50 (52.08%) | 106 (59.89%) | 1.00 | NS |
| TG | 33 (34.38%) | 67 (37.85%) | 1.04 (0.59-1.85) | NS |
| GG | 13 (13.54%) | 4 (2.26%) | 6.89 (1.95-26.53) | 0.0003* |
| TG + GG | 46 (47.92%) | 71 (40.11%) | 1.374 (0.833-2.266) | NS |
| T | 133 (69.27%) | 279 (78.81%) | 1.00 | 0.0166* |
| G | 59 (30.73%) | 75 (21.19%) | 1.65 (1.09-2.51) | |

TABLE 8

Arachidonic Acid pathway related genes

| Common Name | Description | Fold change in EE | Genbank Accession number |
|---|---|---|---|
| ALOX15 | ‖1.13.11.33‖ALOX15‖arachidonate 15-lipoxygenase‖15-@LIPOXYGENASE, RETICULOCYTE ARACHIDONATE‖ | 20.89 | NM_001140 |
| PGDS | ‖PGDS‖5.3.99.2‖prostaglandin-D synthase‖prostaglandin D2 synthase, hematopoietic‖hematopoietic prostaglandin D2 synthase‖ | 5.265 | NM_014485 |
| PTGES | ‖PGES‖TP53I12‖MGST1L1‖PP1294‖PP102‖PTGES‖MGC10317‖PIG12‖MGST1-L1‖MGST-IV‖MGST1-like 1‖p53-INDUCED GENE 12‖prostaglandin E synthase‖p53-induced apoptosis protein 12‖prostaglandin E synthase isoform 2‖prostaglandin E synthase isoform 1‖microsomal glutathione S-transferase 1-like 1‖tumor protein p53 inducible protein 12‖ | 2.822 | NM_198797 |
| LTA4H | ‖3.3.2.6‖LTA4H‖leukotriene A4 hydrolase‖ | 2.205 | NM_000895 |
| PLA2G3 | ‖PLA2G3‖phospholipase A2, group III‖ | 2.156 | NM_015715 |
| PLA2G7 | ‖PAFAH‖PLA2G7‖LDL-PLA2‖LIPOPROTEIN-ASSOCIATED PHOSPHOLIPASE A2 PLATELET-ACTIVATING FACTOR ACETYLHYDROLASE DEFICIENCY‖phospholipase A2, group VII (platelet-activating factor acetylhydrolase, plasma)‖ | 1.737 | NM_005084 |
| PTGS2 | ‖COX2‖PGHS2‖1.14.99.1‖PGHS-2‖PTGS2‖hCox-2‖PGG/HS‖PHS-2‖CYCLOOXYGENASE 2‖PROSTAGLANDIN G/H SYNTHASE 2‖prostaglandin-endoperoxide synthase 2 precursor‖prostaglandin-endoperoxide synthase 2 (prostaglandin G/H synthase and cyclooxygenase)‖ | 1.718 | NM_000963 |

TABLE 8-continued

Arachidonic Acid pathway related genes

| Common Name | Description | Fold change in EE | Genbank Accession number |
|---|---|---|---|
| ALOX5AP | \|\|FLAP\|\|ALOX5AP\|\|5-@LIPOXYGENASE-ACTIVATING PROTEIN\|\|MK-886-binding protein\|\|FIVE-LIPOXYGENASE-ACTIVATING PROTEIN\|\|arachidonate 5-lipoxygenase-activating protein\|\|five-lipoxygenase activating protein\|\| | 1.646 | NM_001629 |
| PTGDS | \|\|PGDS2\|\|PTGDS\|\|PDS\|\|5.3.99.2\|\|prostaglandin-H2 D-isomerase\|\|PGD2 synthase\|\|beta-trace protein\|\|glutathione-independent PGD synthase\|\|PROSTAGLANDIN D2 SYNTHASE, BRAIN\|\|lipocalin-type prostaglandin D synthase\|\|prostaglandin D2 synthase 21 kDa (brain)\|\| | 1.475 | NM_000954 |
| PTGIS | \|\|PGIS\|\|5.3.99.4\|\|PTGIS\|\|CYP8A1\|\|PROSTACYCLIN SYNTHASE\|\|PROSTAGLANDIN I2 SYNTHASE\|\|prostaglandin I2 (prostacyclin) synthase\|\| | 1.345 | NM_000961 |
| PTGFRN | \|\|SMAP-6\|\|CD9P1\|\|FPRP\|\|KIAA1436\|\|CD9P-1\|\|FLJ11001\|\|PTGFRN\|\|EWI-F\|\|FP REGULATORY PROTEIN\|\|CD9 partner 1\|\|prostaglandin F2 receptor negative regulator\|\| | 1.342 | NM_020440 |
| PTGDS | \|\|PGDS2\|\|PTGDS\|\|PDS\|\|5.3.99.2\|\|prostaglandin-H2 D-isomerase\|\|PGD2 synthase\|\|beta-trace protein\|\|glutathione-independent PGD synthase\|\|PROSTAGLANDIN D2 SYNTHASE, BRAIN\|\|lipocalin-type prostaglandin D synthase\|\|prostaglandin D2 synthase 21 kDa (brain)\|\| | 1.334 | NM_000954 |
| PTGER4 | \|\|EP4R\|\|PTGER4\|\|prostaglandin E2 receptor\|\|PGE receptor, EP4 subtype\|\|PROSTAGLANDIN E RECEPTOR 4, EP4 SUBTYPE\|\|prostaglandin E receptor 4, subtype EP4\|\|prostaglandin E receptor 4 (subtype EP4)\|\| | 1.33 | NM_000958 |
| PAFAH2 | \|\|HSD-PLA2\|\|PAFAH2\|\|3.1.1.47\|\|platelet-activating factor acetylhydrolase 2, 40 kDa\|\|platelet-activating factor acetylhydrolase 2 (40 kD)\|\| | 1.329 | NM_000437 |
| HPGD | \|\|PGDH1\|\|15-PGDH\|\|HPGD\|\|hydroxyprostaglandin dehydrogenase 15-(NAD)\|\|15-@HYDROXYPROSTAGLANDIN DEHYDROGENASE, TYPE I\|\| | 1.322 | NM_000860 |
| PTGFRN | \|\|SMAP-6\|\|CD9P1\|\|FPRP\|\|KIAA1436\|\|CD9P-1\|\|FLJ11001\|\|PTGFRN\|\|EWI-F\|\|FP REGULATORY PROTEIN\|\|CD9 partner 1\|\|prostaglandin F2 receptor negative regulator\|\| | 1.304 | NM_020440 |
| HPGD | \|\|PGDH1\|\|15-PGDH\|\|HPGD\|\|hydroxyprostaglandin dehydrogenase 15-(NAD)\|\|15-@HYDROXYPROSTAGLANDIN DEHYDROGENASE, TYPE I\|\| | 1.252 | NM_000860 |
| LTC4S | \|\|MGC33147\|\|LTC4S\|\|2.5.1.37\|\|LTC4 SYNTHASE DEFICIENCY\|\|leukotriene C4 synthase\|\|LTC4S LEUKOTRIENE C4 SYNTHASE DEFICIENCY\|\|leukotriene C4 synthase isoform 1\|\|leukotriene C4 synthase isoform 2\|\| | 1.237 | NM_000897 |
| PTGER2 | \|\|PTGER2\|\|Prostaglandin E receptor 2, EP2 subtype, 53 kD\|\|prostaglandin E receptor 2 (subtype EP2), 53 kDa\|\| | 1.171 | NM_000956 |
| PTGES | \|\|PGES\|\|TP53I12\|\|MGST1L1\|\|PP1294\|\|PP102\|\|PTGES\|\|MGC10317\|\|PIG12\|\|MGST1-L1\|\|MGST-IV\|\|MGST1-like 1\|\|p53-INDUCED GENE 12\|\|prostaglandin E synthase\|\|p53-induced apoptosis protein 12\|\|prostaglandin E synthase isoform 2\|\|prostaglandin E synthase isoform 1\|\|microsomal glutathione S-transferase 1-like 1\|\|tumor protein p53 inducible protein 12\|\| | 1.146 | NM_198797 |

TABLE 8-continued

Arachidonic Acid pathway related genes

| Common Name | Description | Fold change in EE | Genbank Accession number |
|---|---|---|---|
| PLA2G4C | \|\|cPLA2-gamma\|\|PLA2G4C\|\|cytosolic phospholipase A2 gamma\|\|phospholipase A2, group IVC (cytosolic)\|\|PHOSPHOLIPASE A2, CYTOSOLIC, CALCIUM-INDEPENDENT, GAMMA\|\|phospholipase A2, group IVC (cytosolic, calcium-independent)\|\| | 1.133 | NM_003706 |
| IGSF8 | \|\|PGRL\|\|IGSF8\|\|CD81P3\|\|PROSTAGLANDIN REGULATORY-LIKE\|\|CD81 PARTNER 3\|\|immunoglobulin superfamily, member 8\|\| | 1.124 | NM_052868 |
| LTB4R | \|\|BLTR\|\|CMKRL1\|\|BLT1\|\|LTB4-R\|\|LTB4R\|\|GPR16\|\|P2RY7\|\|LTB4R1\|\|LTBR1\|\|PURINOCEPTOR P2Y7\|\|P2Y purinoceptor 7\|\|Chemoattractant receptor-like 1\|\|leukotriene B4 receptor\|\|G protein-coupled receptor 16\|\|Leukotriene B4 receptor 1\|\|LEUKOTRIENE B4 G PROTEIN-COUPLED RECEPTOR\|\|PURINERGIC RECEPTOR P2Y, G PROTEIN-COUPLED, 7\|\|purinergic receptor P2Y, G-protein coupled, 7\|\|leukotriene b4 receptor (chemokine receptor-like 1)\|\| | 1.117 | NM_000752 |
| HPGD | \|\|PGDH1\|\|15-PGDH\|\|HPGD\|\|hydroxyprostaglandin dehydrogenase 15-(NAD)\|\|15-@HYDROXYPROSTAGLANDIN DEHYDROGENASE, TYPE I\|\| | 1.115 | NM_000860 |
| PTGDS | \|\|PGDS2\|\|PTGDS\|\|PDS\|\|5.3.99.2\|\|prostaglandin-H2 D-isomerase\|\|PGD2 synthase\|\|beta-trace protein\|\|glutathione-independent PGD synthase\|\|PROSTAGLANDIN D2 SYNTHASE, BRAIN\|\|lipocalin-type prostaglandin D synthase\|\|prostaglandin D2 synthase 21 kDa (brain)\|\| | 1.106 | NM_000954 |
| PAFAH2 | \|\|HSD-PLA2\|\|PAFAH2\|\|3.1.1.47\|\|platelet-activating factor acetylhydrolase 2, 40 kDa\|\|platelet-activating factor acetylhydrolase 2 (40 kD)\|\| | 1.105 | NM_000437 |
| PTGER3 | \|\|MGC27302\|\|PTGER3\|\|prostanoid EP3 receptor\|\|prostaglandin receptor (PGE-2)\|\|prostaglandin E2 receptor\|\|PGE receptor, EP3 subtype\|\|prostaglandin E receptor 3 (subtype EP3)\|\|PROSTAGLANDIN E RECEPTOR 3, EP3 SUBTYPE\|\|prostaglandin E receptor 3, subtype EP3 isoform 7\|\|prostaglandin E receptor 3, subtype EP3 isoform 8\|\|prostaglandin E receptor 3, subtype EP3 isoform 1\|\|prostaglandin E receptor 3, subtype EP3 isoform 2\|\|prostaglandin E receptor 3, subtype EP3 isoform 3\|\|prostaglandin E receptor 3, subtype EP3 isoform 4\|\|prostaglandin E receptor 3, subtype EP3 isoform 5\|\|prostaglandin E receptor 3, subtype EP3 isoform 6\|\| | 1.104 | NM_198715 |
| PTGDR | \|\|MGC49004\|\|PTGDR\|\|PGD receptor\|\|prostanoid DP receptor\|\|prostaglandin D2 receptor (DP)\|\| | 1.101 | NM_000953 |
| LYPLA2 | \|\|LYPLA2\|\|3.1.1.5\|\|APT-2\|\|DJ886K2.4\|\|acyl-protein thioesterase\|\|lysophospholipase II\|\| | 1.093 | NM_007260 |
| LYPLA2 | \|\|LYPLA2\|\|3.1.1.5\|\|APT-2\|\|DJ886K2.4\|\|acyl-protein thioesterase\|\|lysophospholipase II\|\| | 1.093 | NM_007260 |
| PTGER3 | \|\|MGC27302\|\|PTGER3\|\|prostanoid EP3 receptor\|\|prostaglandin receptor (PGE-2)\|\|prostaglandin E2 receptor\|\|PGE receptor, EP3 subtype\|\|prostaglandin E receptor 3 (subtype EP3)\|\|PROSTAGLANDIN E RECEPTOR 3, EP3 SUBTYPE\|\|prostaglandin E receptor 3, subtype EP3 isoform 7\|\|prostaglandin E receptor 3, subtype EP3 isoform | 1.091 | NM_198715 |

TABLE 8-continued

Arachidonic Acid pathway related genes

| Common Name | Description | Fold change in EE | Genbank Accession number |
|---|---|---|---|
| | 8||prostaglandin E receptor 3, subtype EP3 isoform 1||prostaglandin E receptor 3, subtype EP3 isoform 2||prostaglandin E receptor 3, subtype EP3 isoform 3||prostaglandin E receptor 3, subtype EP3 isoform 4||prostaglandin E receptor 3, subtype EP3 isoform 5||prostaglandin E receptor 3, subtype EP3 isoform 6|| | | |
| PTGIR | ||PTGIR||PRIPR||PGI receptor||prostacyclin receptor||prostanoid IP receptor||PROSTAGLANDIN I2 RECEPTOR||prostaglandin I2 (prostacyclin) receptor (IP)|| | 1.079 | NM_000960 |
| LTB4R2 | ||||LTB4R2||leukotriene B4 receptor 2|| | 1.076 | NM_019839 |
| PLA2G4C | ||cPLA2-gamma||PLA2G4C||cytosolic phospholipase A2 gamma||phospholipase A2, group IVC (cytosolic)||PHOSPHOLIPASE A2, CYTOSOLIC, CALCIUM-INDEPENDENT, GAMMA||phospholipase A2, group IVC (cytosolic, calcium-independent)|| | 1.074 | NM_003706 |
| HPGD | ||PGDH1||15-PGDH||HPGD||hydroxyprostaglandin dehydrogenase 15-(NAD)||15-@HYDROXYPROSTAGLANDIN DEHYDROGENASE, TYPE I|| | 1.067 | NM_000860 |
| LYPLA2 | ||LYPLA2||3.1.1.5||APT-2||DJ886K2.4||acyl-protein thioesterase||lysophospholipase II|| | 1.061 | NM_007260 |
| TBXAS1 | ||TS||TBXAS1||5.3.99.5||TXAS||TXA synthase||CYP5A1 THROMBOXANE SYNTHETASE DEFICIENCY||THROMBOXANE A SYNTHASE, PLATELET||thromboxane A synthase 1 (platelet, cytochrome P450, subfamily V)||thromboxane A synthase 1 (platelet, cytochrome P450, family 5, subfamily A)||thromboxane A synthase 1 (platelet, cytochrome P450, family 5, subfamily A) isoform TXS-II|| | 1.057 | NM_001061 |
| PLA2G4D | ||PLA2G4D||phospholipase A2, group IVD (cytosolic)|| | 1.049 | NM_178034 |
| PTGER3 | ||MGC27302||PTGER3||prostanoid EP3 receptor||prostaglandin receptor (PGE-2)||prostaglandin E2 receptor||PGE receptor, EP3 subtype||prostaglandin E receptor 3 (subtype EP3)||PROSTAGLANDIN E RECEPTOR 3, EP3 SUBTYPE||prostaglandin E receptor 3, subtype EP3 isoform 7||prostaglandin E receptor 3, subtype EP3 isoform 8||prostaglandin E receptor 3, subtype EP3 isoform 1||prostaglandin E receptor 3, subtype EP3 isoform 2||prostaglandin E receptor 3, subtype EP3 isoform 3||prostaglandin E receptor 3, subtype EP3 isoform 4||prostaglandin E receptor 3, subtype EP3 isoform 5||prostaglandin E receptor 3, subtype EP3 isoform 6|| | 1.046 | NM_198715 |
| CYSLTR2 | ||CYSLT2||CYSLTR2||cysteinyl leukotriene receptor 2|| | 1.035 | NM_020377 |
| PTGES2 | ||PTGES2||PGES2||GBF1||GATE-BINDING FACTOR 1||prostaglandin E synthase 2|| | 1.033 | NM_198939 |
| TBXA2R | ||TBXA2R||thromboxane A2 receptor||THROMBOXANE A2 RECEPTOR, PLATELET||thromboxane A2 receptor isoform 2||TBXA2R BLEEDING DISORDER DUE TO DEFECTIVE THROMBOXANE A2 RECEPTOR|| | 1.024 | NM_201636 |
| PTGER3 | ||MGC27302||PTGER3||prostanoid EP3 receptor||prostaglandin receptor (PGE-2)||prostaglandin E2 receptor||PGE receptor, EP3 subtype||prostaglandin E receptor 3 (subtype EP3)||PROSTAGLANDIN E RECEPTOR 3, EP3 SUBTYPE||prostaglandin E receptor 3, | 1.022 | NM_198715 |

TABLE 8-continued

Arachidonic Acid pathway related genes

| Common Name | Description | Fold change in EE | Genbank Accession number |
|---|---|---|---|
| PTGER3 | subtype EP3 isoform 7\|\|prostaglandin E receptor 3, subtype EP3 isoform 8\|\|prostaglandin E receptor 3, subtype EP3 isoform 1\|\|prostaglandin E receptor 3, subtype EP3 isoform 2\|\|prostaglandin E receptor 3, subtype EP3 isoform 3\|\|prostaglandin E receptor 3, subtype EP3 isoform 4\|\|prostaglandin E receptor 3, subtype EP3 isoform 5\|\|prostaglandin E receptor 3, subtype EP3 isoform 6\|\| \|\|MGC27302\|\|PTGER3\|\|prostanoid EP3 receptor\|\|prostaglandin receptor (PGE-2)\|\|prostaglandin E2 receptor\|\|PGE receptor, EP3 subtype\|\|prostaglandin E receptor 3 (subtype EP3)\|\|PROSTAGLANDIN E RECEPTOR 3, EP3 SUBTYPE\|\|prostaglandin E receptor 3, subtype EP3 isoform 7\|\|prostaglandin E receptor 3, subtype EP3 isoform 8\|\|prostaglandin E receptor 3, subtype EP3 isoform 1\|\|prostaglandin E receptor 3, subtype EP3 isoform 2\|\|prostaglandin E receptor 3, subtype EP3 isoform 3\|\|prostaglandin E receptor 3, subtype EP3 isoform 4\|\|prostaglandin E receptor 3, subtype EP3 isoform 5\|\|prostaglandin E receptor 3, subtype EP3 isoform 6\|\| | 1.02 | NM_198715 |
| PTGER3 | \|\|MGC27302\|\|PTGER3\|\|prostanoid EP3 receptor\|\|prostaglandin receptor (PGE-2)\|\|prostaglandin E2 receptor\|\|PGE receptor, EP3 subtype\|\|prostaglandin E receptor 3 (subtype EP3)\|\|PROSTAGLANDIN E RECEPTOR 3, EP3 SUBTYPE\|\|prostaglandin E receptor 3, subtype EP3 isoform 7\|\|prostaglandin E receptor 3, subtype EP3 isoform 8\|\|prostaglandin E receptor 3, subtype EP3 isoform 1\|\|prostaglandin E receptor 3, subtype EP3 isoform 2\|\|prostaglandin E receptor 3, subtype EP3 isoform 3\|\|prostaglandin E receptor 3, subtype EP3 isoform 4\|\|prostaglandin E receptor 3, subtype EP3 isoform 5\|\|prostaglandin E receptor 3, subtype EP3 isoform 6\|\| | 1.017 | NM_198715 |
| PTGDR | \|\|MGC49004\|\|PTGDR\|\|PGD receptor\|\|prostanoid DP receptor\|\|prostaglandin D2 receptor (DP)\|\| | 1.012 | NM_000953 |
| TBXA2R | \|\|TBXA2R\|\|thromboxane A2 receptor\|\|THROMBOXANE A2 RECEPTOR, PLATELET\|\|thromboxane A2 receptor isoform 2\|\|TBXA2R BLEEDING DISORDER DUE TO DEFECTIVE THROMBOXANE A2 RECEPTOR\|\| | 1.01 | NM_201636 |
| PLA2R1 | \|\|PLA2IR\|\|PLA2-R\|\|PLA2R1\|\|PLA2G1R\|\|PHOSPHOLIPASE A2 RECEPTOR, 180-KD\|\|phospholipase A2 receptor 1, 180 kDa\|\| | 1.009 | NM_007366 |
| PLA2G10 | \|\|GXPLA2\|\|GXSPLA2\|\|PLA2G10\|\|phospholipase A2, group X\|\|SECRETORY PHOSPHOLIPASE A2, GROUP X\|\|PHOSPHOLIPASE A2, SECRETORY, CALCIUM-DEPENDENT, GROUP X\|\| | 1.008 | NM_003561 |
| PTGFR | \|\|MGC46203\|\|PTGFR\|\|PGF receptor\|\|PGF2 alpha receptor\|\|prostaglandin receptor (2-alpha)\|\|PROSTAGLANDIN RECEPTOR F(2-ALPHA)\|\|prostanoid FP receptor\|\|prostaglandin F2 alpha receptor\|\|prostaglandin F receptor (FP)\|\| | 1.006 | NM_000959 |
| PTGDR | \|\|MGC49004\|\|PTGDR\|\|PGD receptor\|\|prostanoid DP receptor\|\|prostaglandin D2 receptor (DP)\|\| | 0.998 | NM_000953 |

TABLE 8-continued

Arachidonic Acid pathway related genes

| Common Name | Description | Fold change in EE | Genbank Accession number |
|---|---|---|---|
| PLA2G1B | \|\|PLA2G1B\|\|3.1.1.4\|\|PPLA2\|\|PLA2A\|\|PHOSPHOLIPASE A2, PANCREATIC\|\|PHOSPHOLIPASE A2 POLYPEPTIDE A\|\|phospholipase A2, group IB (pancreas)\|\| | 0.989 | NM_000928 |
| PLA2G6 | \|\|PLA2G6\|\|iPLA2\|\|PHOSPHOLIPASE A2, CALCIUM-INDEPENDENT\|\|cytosolic, calcium-independent phospholipase A2\|\|phospholipase A2, group VI (cytosolic, calcium-independent)\|\| | 0.988 | NM_003560 |
| HTATIP | \|\|PLIP\|\|HTATIP\|\|HTATIP1\|\|TAT-INTERACTING PROTEIN, 60-KD\|\|HIV-1 TAT-INTERACTING PROTEIN\|\|cPLA2 interacting protein\|\|TIP60 PLA2-INTERACTING PROTEIN\|\|Tat interactive protein (60 kD)\|\|HIV-1 Tat interactive protein, 60 kDa\|\|HIV-1 Tat interactive protein, 60 kDa isoform 3\|\|HIV-1 Tat interactive protein, 60 kDa isoform 2\|\|HIV-1 Tat interactive protein, 60 kDa isoform 1\|\| | 0.987 | NM_182710 |
| PLA2G5 | \|\|3.1.1.4\|\|PLA2G5\|\|phospholipase A2, group V\|\| | 0.983 | NM_000929 |
| PTGER3 | \|\|MGC27302\|\|PTGER3\|\|prostanoid EP3 receptor\|\|prostaglandin receptor (PGE-2)\|\|prostaglandin E2 receptor\|\|PGE receptor, EP3 subtype\|\|prostaglandin E receptor 3 (subtype EP3)\|\|PROSTAGLANDIN E RECEPTOR 3, EP3 SUBTYPE\|\|prostaglandin E receptor 3, subtype EP3 isoform 7\|\|prostaglandin E receptor 3, subtype EP3 isoform 8\|\|prostaglandin E receptor 3, subtype EP3 isoform 1\|\|prostaglandin E receptor 3, subtype EP3 isoform 2\|\|prostaglandin E receptor 3, subtype EP3 isoform 3\|\|prostaglandin E receptor 3, subtype EP3 isoform 4\|\|prostaglandin E receptor 3, subtype EP3 isoform 5\|\|prostaglandin E receptor 3, subtype EP3 isoform 6\|\| | 0.983 | NM_198715 |
| PTGER3 | \|\|MGC27302\|\|PTGER3\|\|prostanoid EP3 receptor\|\|prostaglandin receptor (PGE-2)\|\|prostaglandin E2 receptor\|\|PGE receptor, EP3 subtype\|\|prostaglandin E receptor 3 (subtype EP3)\|\|PROSTAGLANDIN E RECEPTOR 3, EP3 SUBTYPE\|\|prostaglandin E receptor 3, subtype EP3 isoform 7\|\|prostaglandin E receptor 3, subtype EP3 isoform 8\|\|prostaglandin E receptor 3, subtype EP3 isoform 1\|\|prostaglandin E receptor 3, subtype EP3 isoform 2\|\|prostaglandin E receptor 3, subtype EP3 isoform 3\|\|prostaglandin E receptor 3, subtype EP3 isoform 4\|\|prostaglandin E receptor 3, subtype EP3 isoform 5\|\|prostaglandin E receptor 3, subtype EP3 isoform 6\|\| | 0.981 | NM_198715 |
| ALOX15B | \|\|ALOX15B\|\|arachidonate 15-lipoxygenase, second type\|\|15-@LIPOXYGENASE, RETICULOCYTE ARACHIDONATE, SECOND TYPE\|\| | 0.967 | NM_001141 |
| CYSLTR1 | \|\|HMTMF81\|\|MGC46139\|\|CYSLTR1\|\|CYSLT1R\|\|HG55\|\|LTD4 receptor\|\|CysLTR vide supra\|\|cysteinyl leukotriene receptor 1\|\|cysteinyl leukotriene D4 receptor\|\| | 0.965 | NM_006639 |
| TBXA2R | \|\|TBXA2R\|\|thromboxane A2 receptor\|\|THROMBOXANE A2 RECEPTOR, PLATELET\|\|thromboxane A2 receptor isoform 2\|\|TBXA2R BLEEDING DISORDER DUE TO DEFECTIVE THROMBOXANE A2 RECEPTOR\|\| | 0.963 | NM_201636 |
| PTGER3 | \|\|MGC27302\|\|PTGER3\|\|prostanoid EP3 receptor\|\|prostaglandin receptor (PGE-2)\|\|prostaglandin E2 receptor\|\|PGE receptor, EP3 subtype\|\|prostaglandin E | 0.962 | NM_198715 |

TABLE 8-continued

Arachidonic Acid pathway related genes

| Common Name | Description | Fold change in EE | Genbank Accession number |
|---|---|---|---|
| | receptor 3 (subtype EP3)||PROSTAGLANDIN E RECEPTOR 3, EP3 SUBTYPE||prostaglandin E receptor 3, subtype EP3 isoform 7||prostaglandin E receptor 3, subtype EP3 isoform 8||prostaglandin E receptor 3, subtype EP3 isoform 1||prostaglandin E receptor 3, subtype EP3 isoform 2||prostaglandin E receptor 3, subtype EP3 isoform 3||prostaglandin E receptor 3, subtype EP3 isoform 4||prostaglandin E receptor 3, subtype EP3 isoform 5||prostaglandin E receptor 3, subtype EP3 isoform 6|| | | |
| PLA2G12B | ||PLA2G12B||phospholipase A2, group XIIB|| | 0.961 | NM_032562 |
| LOC112868 | ||||Similar to Group X secretory phospholipase A2 precursor (Phosphatidylcholine 2-acylhydrolase GX) (GX sPLA2) (sPLA2-X) (LOC388229), mRNA|| | 0.957 | AL390134 |
| PTGER4 | ||EP4R||PTGER4||prostaglandin E2 receptor||PGE receptor, EP4 subtype||PROSTAGLANDIN E RECEPTOR 4, EP4 SUBTYPE||prostaglandin E receptor 4, subtype EP4||prostaglandin E receptor 4 (subtype EP4)|| | 0.955 | NM_000958 |
| TBXAS1 | ||TS||TBXAS1||5.3.99.5||TXAS||TXA synthase||CYP5A1 THROMBOXANE SYNTHETASE DEFICIENCY||THROMBOXANE A SYNTHASE, PLATELET||thromboxane A synthase 1 (platelet, cytochrome P450, subfamily V)||thromboxane A synthase 1 (platelet, cytochrome P450, family 5, subfamily A)||thromboxane A synthase 1 (platelet, cytochrome P450, family 5, subfamily A) isoform TXS-II|| | 0.955 | NM_001061 |
| IPLA2(GAMMA); IPLA2-2 | ||||IPLA2(GAMMA)||intracellular membrane-associated calcium-independent phospholipase A2 gamma|| | 0.951 | XM_291241 |
| CYSLTR1 | ||HMTMF81||MGC46139||CYSLTR1||CYSLT1R||HG55||LTD4 receptor||CysLTR vide supra||cysteinyl leukotriene receptor 1||cysteinyl leukotriene D4 receptor|| | 0.949 | NM_006639 |
| PLA2R1 | ||PLA2IR||PLA2-R||PLA2R1||PLA2G1R||PHOSPHOLIPASE A2 RECEPTOR, 180-KD||phospholipase A2 receptor 1, 180 kDa|| | 0.948 | NM_007366 |
| LTB4R | ||BLTR||CMKRL1||GPR16||BLT1||LTB4-R||LTB4R||GPR16||P2RY7||LTB4R1||LTBR1||PURINOCEPTOR P2Y7||P2Y purinoceptor 7||Chemoattractant receptor-like 1||leukotriene B4 receptor||G protein-coupled receptor 16||Leukotriene B4 receptor 1||LEUKOTRIENE B4 G PROTEIN-COUPLED RECEPTOR||PURINERGIC RECEPTOR P2Y, G PROTEIN-COUPLED, 7||purinergic receptor P2Y, G-protein coupled, 7||leukotriene b4 receptor (chemokine receptor-like 1)|| | 0.945 | NM_000752 |
| TBXA2R | ||TBXA2R||thromboxane A2 receptor||THROMBOXANE A2 RECEPTOR, PLATELET||thromboxane A2 receptor isoform 2||TBXA2R BLEEDING DISORDER DUE TO DEFECTIVE THROMBOXANE A2 RECEPTOR|| | 0.944 | NM_201636 |
| PLA2G2D | ||SPLASH||PLA2G2D||sPLA2S||secretory phospholipase A2s||SECRETORY-TYPE PLA, STROMA-ASSOCIATED HOMOLOG||phospholipase A2, group IID|| | 0.943 | NM_012400 |
| LOC112868 | ||||Similar to Group X secretory phospholipase A2 precursor (Phosphatidylcholine 2-acylhydrolase GX) (GX sPLA2) (sPLA2-X) (LOC388229), mRNA|| | 0.943 | AL390134 |

TABLE 8-continued

Arachidonic Acid pathway related genes

| Common Name | Description | Fold change in EE | Genbank Accession number |
|---|---|---|---|
| PLA2G5 | \|\|3.1.1.4\|\|PLA2G5\|\|phospholipase A2, group V\|\| | 0.94 | NM_000929 |
| PTGER3 | \|\|MGC27302\|\|PTGER3\|\|prostanoid EP3 receptor\|\|prostaglandin receptor (PGE-2)\|\|prostaglandin E2 receptor\|\|PGE receptor, EP3 subtype\|\|prostaglandin E receptor 3 (subtype EP3)\|\|PROSTAGLANDIN E RECEPTOR 3, EP3 SUBTYPE\|\|prostaglandin E receptor 3, subtype EP3 isoform 7\|\|prostaglandin E receptor 3, subtype EP3 isoform 8\|\|prostaglandin E receptor 3, subtype EP3 isoform 1\|\|prostaglandin E receptor 3, subtype EP3 isoform 2\|\|prostaglandin E receptor 3, subtype EP3 isoform 3\|\|prostaglandin E receptor 3, subtype EP3 isoform 4\|\|prostaglandin E receptor 3, subtype EP3 isoform 5\|\|prostaglandin E receptor 3, subtype EP3 isoform 6\|\| | 0.932 | NM_198715 |
| PTGER1 | \|\|PTGER1\|\|prostanoid EP1 receptor\|\|PGE receptor, EP1 subtype\|\|PROSTAGLANDIN E RECEPTOR 1, EP1 SUBTYPE\|\|prostaglandin E receptor 1, subtype EP1\|\|prostaglandin E receptor 1 (subtype EP1), 42 kDa\|\| | 0.932 | NM_000955 |
| PTGS1 | \|\|PGHS-1\|\|PTGHS\|\|COX3\|\|1.14.99.1\|\|PGG/HS\|\|PCOX1\|\|PHS1\|\|PTGS1\|\|CYCLOOXYGENASE 1\|\|PARTIAL COX1 PROTEINS\|\|PGHS1 CYCLOOXYGENASE 3\|\|PROSTAGLANDIN G/H SYNTHASE 1\|\|prostaglandin-endoperoxide synthase 1 isoform 2 precursor\|\|prostaglandin-endoperoxide synthase 1 isoform 1 precursor\|\|prostaglandin-endoperoxide synthase 1 (prostaglandin G/H synthase and cyclooxygenase)\|\| | 0.929 | NM_000962 |
| ALOX5 | \|\|5-@LIPOXYGENASE\|\|1.13.11.34\|\|LOG5\|\|5-@LO\|\|ALOX5\|\|arachidonate 5-lipoxygenase\|\| | 0.926 | NM_000698 |
| PTGS1 | \|\|PGHS-1\|\|PTGHS\|\|COX3\|\|1.14.99.1\|\|PGG/HS\|\|PCOX1\|\|PHS1\|\|PTGS1\|\|CYCLOOXYGENASE 1\|\|PARTIAL COX1 PROTEINS\|\|PGHS1 CYCLOOXYGENASE 3\|\|PROSTAGLANDIN G/H SYNTHASE 1\|\|prostaglandin-endoperoxide synthase 1 isoform 2 precursor\|\|prostaglandin-endoperoxide synthase 1 isoform 1 precursor\|\|prostaglandin-endoperoxide synthase 1 (prostaglandin G/H synthase and cyclooxygenase)\|\| | 0.921 | NM_000962 |
| PTGS1 | \|\|PGHS-1\|\|PTGHS\|\|COX3\|\|1.14.99.1\|\|PGG/HS\|\|PCOX1\|\|PHS1\|\|PTGS1\|\|CYCLOOXYGENASE 1\|\|PARTIAL COX1 PROTEINS\|\|PGHS1 CYCLOOXYGENASE 3\|\|PROSTAGLANDIN G/H SYNTHASE 1\|\|prostaglandin-endoperoxide synthase 1 isoform 2 precursor\|\|prostaglandin-endoperoxide synthase 1 isoform 1 precursor\|\|prostaglandin-endoperoxide synthase 1 (prostaglandin G/H synthase and cyclooxygenase)\|\| | 0.92 | NM_000962 |
| *H. sapiens* EP4 prostaglandin receptor pseudogene c16/g7 | *H. sapiens* EP4 prostaglandin receptor pseudogene c16/g7 | 0.912 | BC042539 |
| PLA2G2F | \|\|PLA2G2F\|\|phospholipase A2, group IIF\|\| | 0.912 | NM_022819 |
| PLAA | \|\|PLAA\|\|PLAP\|\|PLA2P\|\|phospholipase A2-activating protein\|\|phospholipase A2 activating protein\|\| | 0.911 | NM_004253 |

TABLE 8-continued

Arachidonic Acid pathway related genes

| Common Name | Description | Fold change in EE | Genbank Accession number |
|---|---|---|---|
| ALOXE3 | \|\|ALOXE3\|\|LOX TYPE 3\|\|arachidonate lipoxygenase 3\|\|LIPOXYGENASE TYPE 3, EPIDERMAL\|\| | 0.907 | NM_021628 |
| PTGS2 | \|\|COX2\|\|PGHS2\|\|1.14.99.1\|\|PGHS-2\|\|PTGS2\|\|hCox-2\|\|PGG/HS\|\|PHS-2\|\|CYCLOOXYGENASE 2\|\|PROSTAGLANDIN G/H SYNTHASE 2\|\|prostaglandin-endoperoxide synthase 2 precursor\|\|prostaglandin-endoperoxide synthase 2 (prostaglandin G/H synthase and cyclooxygenase)\|\| | 0.906 | NM_000963 |
| PLA2G6 | \|\|PLA2G6\|\|iPLA2\|\|PHOSPHOLIPASE A2, CALCIUM-INDEPENDENT\|\|cytosolic, calcium-independent phospholipase A2\|\|phospholipase A2, group VI (cytosolic, calcium-independent)\|\| | 0.904 | NM_003560 |
| ALOX12P2 | \|\|ALOX12E\|\|ALOX12P2\|\|12-lipoxygenase-related protein\|\|arachidonate 12-lipoxygenase pseudogene 2\|\|hair and skin epidermal-type 12-lipoxygenase-related pseudogene\|\| | 0.899 | AL832768 |
| PLA2G2E | \|\|PLA2G2E\|\|phospholipase A2, group IIE\|\| | 0.899 | NM_014589 |
| PTGIS | \|\|PGIS\|\|5.3.99.4\|\|PTGIS\|\|CYP8A1\|\|PROSTACYCLIN SYNTHASE\|\|PROSTAGLANDIN I2 SYNTHASE\|\|prostaglandin I2 (prostacyclin) synthase\|\| | 0.897 | NM_000961 |
| PLA2R1 | \|\|PLA2IR\|\|PLA2-R\|\|PLA2R1\|\|PLA2G1R\|\|PHOSPHOLIPASE A2 RECEPTOR, 180-KD\|\|phospholipase A2 receptor 1, 180 kDa\|\| | 0.893 | NM_007366 |
| PLA2G5 | \|\|3.1.1.4\|\|PLA2G5\|\|phospholipase A2, group V\|\| | 0.891 | NM_000929 |
| IPLA2(GAMMA); IPLA2-2 | \|\|\|\|\|IPLA2(GAMMA)\|\|intracellular membrane-associated calcium-independent phospholipase A2 gamma\|\| | 0.888 | XM_291241 |
| PTGER1 | \|\|PTGER1\|\|prostanoid EP1 receptor\|\|PGE receptor, EP1 subtype\|\|PROSTAGLANDIN E RECEPTOR 1, EP1 SUBTYPE\|\|prostaglandin E receptor 1, subtype EP1\|\|prostaglandin E receptor 1 (subtype EP1), 42 kDa\|\| | 0.882 | NM_000955 |
| CYSLTR1 | \|\|HMTMF81\|\|MGC46139\|\|CYSLTR1\|\|CYSLT1R\|\|HG55\|\|LTD4 receptor\|\|CysLTR vide supra\|\|cysteinyl leukotriene receptor 1\|\|cysteinyl leukotriene D4 receptor\|\| | 0.876 | NM_006639 |
| PTGIS | \|\|PGIS\|\|5.3.99.4\|\|PTGIS\|\|CYP8A1\|\|PROSTACYCLIN SYNTHASE\|\|PROSTAGLANDIN I2 SYNTHASE\|\|prostaglandin I2 (prostacyclin) synthase\|\| | 0.872 | NM_000961 |
| PLA2G4B | \|\|HsT16992\|\|PLA2G4B\|\|cPLA2-beta\|\|PHOSPHOLIPASE A2, CYTOSOLIC, CALCIUM-DEPENDENT, BETA\|\|phospholipase A2, group IVB (cytosolic)\|\| | 0.867 | NM_005090 |
| PLA2R1 | \|\|PLA2IR\|\|PLA2-R\|\|PLA2R1\|\|PLA2G1R\|\|PHOSPHOLIPASE A2 RECEPTOR, 180-KD\|\|phospholipase A2 receptor 1, 180 kDa\|\| | 0.858 | NM_007366 |
| ALOXE3 | \|\|ALOXE3\|\|LOX TYPE 3\|\|arachidonate lipoxygenase 3\|\|LIPOXYGENASE TYPE 3, EPIDERMAL\|\| | 0.855 | NM_021628 |
| SLCO2A1 | \|\|OATP2A1\|\|SLC21A2\|\|SLCO2A1\|\|PGT\|\|solute carrier organic anion transporter family, member 2A1\|\|solute carrier family 21 (prostaglandin transporter), member 2\|\| | 0.854 | NM_005630 |
| IPLA2(GAMMA); IPLA2-2 | \|\|\|\|\|IPLA2(GAMMA)\|\|intracellular membrane-associated calcium-independent phospholipase A2 gamma\|\| | 0.853 | XM_291241 |
| PLA2G12B | \|\|PLA2G12B\|\|phospholipase A2, group XIIB\|\| | 0.844 | NM_032562 |
| PTGER1 | \|\|PTGER1\|\|prostanoid EP1 receptor\|\|PGE receptor, EP1 subtype\|\|PROSTAGLANDIN E RECEPTOR 1, EP1 SUBTYPE\|\|prostaglandin E receptor 1, subtype EP1\|\|prostaglandin E receptor 1 (subtype EP1), 42 kDa\|\| | 0.844 | NM_000955 |

TABLE 8-continued

Arachidonic Acid pathway related genes

| Common Name | Description | Fold change in EE | Genbank Accession number |
|---|---|---|---|
| TBXA2R | ||TBXA2R||thromboxane A2 receptor||THROMBOXANE A2 RECEPTOR, PLATELET||thromboxane A2 receptor isoform 2||TBXA2R BLEEDING DISORDER DUE TO DEFECTIVE THROMBOXANE A2 RECEPTOR|| | 0.838 | NM_201636 |
| PLA2G6 | ||PLA2G6||iPLA2||PHOSPHOLIPASE A2, CALCIUM-INDEPENDENT||cytosolic, calcium-independent phospholipase A2||phospholipase A2, group VI (cytosolic, calcium-independent)|| | 0.833 | NM_003560 |
| PLA2G6 | ||PLA2G6||iPLA2||PHOSPHOLIPASE A2, CALCIUM-INDEPENDENT||cytosolic, calcium-independent phospholipase A2||phospholipase A2, group VI (cytosolic, calcium-independent)|| | 0.83 | NM_003560 |
| ALOX5 | ||5-@LIPOXYGENASE||1.13.11.34||LOG5||5-@LO||ALOX5||arachidonate 5-lipoxygenase|| | 0.806 | NM_000698 |
| PTGS1 | ||PGHS-1||PTGHS||COX3||1.14.99.1||PGG/HS||PCOX1||PHS1||PTGS1||CYCLOOXYGENASE 1||PARTIAL COX1 PROTEINS||PGHS1 CYCLOOXYGENASE 3||PROSTAGLANDIN G/H SYNTHASE 1||prostaglandin-endoperoxide synthase 1 isoform 2 precursor||prostaglandin-endoperoxide synthase 1 isoform 1 precursor||prostaglandin-endoperoxide synthase 1 (prostaglandin G/H synthase and cyclooxygenase)|| | 0.804 | NM_000962 |
| ALOX15B | ||ALOX15B||arachidonate 15-lipoxygenase, second type||15-@LIPOXYGENASE, RETICULOCYTE ARACHIDONATE, SECOND TYPE|| | 0.773 | NM_001141 |
| ALOX5 | ||5-@LIPOXYGENASE||1.13.11.34||LOG5||5-@LO||ALOX5||arachidonate 5-lipoxygenase|| | 0.771 | NM_000698 |
| CYP4F2 | ||CYP4F2||1.14.13.30||CPF2||leukotriene-B4 20-monooxygenase||LTB4 OMEGA-HYDROXYLASE, LIVER||LEUKOTRIENE B4 OMEGA-HYDROXYLASE, LIVER||cytochrome P450, subfamily IVF, polypeptide 2||cytochrome P450, family 4, subfamily F, polypeptide 2|| | 0.764 | NM_001082 |
| CYP2J2 | ||CPJ2||CYP2J2||1.14.14.1||microsomal monooxygenase||flavoprotein-linked monooxygenase||CYTOCHROME P450 ARACHIDONIC ACID EPOXYGENASE||CYTOCHROME P450, SUBFAMILY IIJ, POLYPEPTIDE 2||cytochrome P450, family 2, subfamily J, polypeptide 2||cytochrome P450, subfamily IIJ (arachidonic acid epoxygenase) polypeptide 2|| | 0.736 | NM_000775 |
| CYP4F3 | ||1.14.13.30||CYP4F3||CPF3||LTB4H||leukotriene-B4 20-monooxygenase||cytochrome P450-LTB-omega||LTB OMEGA-HYDROXYLASE||LEUKOTRIENE B4 OMEGA-HYDROXYLASE||cytochrome P450, family 4, subfamily F, polypeptide 3||cytochrome P450, subfamily IVF, polypeptide 3 (leukotriene B4 omega hydroxylase)|| | 0.727 | NM_000896 |
| PLA2G4B | ||HsT16992||PLA2G4B||cPLA2-beta||PHOSPHOLIPASE A2, CYTOSOLIC, CALCIUM-DEPENDENT, BETA||phospholipase A2, group IVB (cytosolic)|| | 0.71 | NM_005090 |
| ALOX5 | ||5-@LIPOXYGENASE||1.13.11.34||LOG5||5-@LO||ALOX5||arachidonate 5-lipoxygenase|| | 0.679 | NM_000698 |

TABLE 8-continued

Arachidonic Acid pathway related genes

| Common Name | Description | Fold change in EE | Genbank Accession number |
|---|---|---|---|
| PLA2G4B | ||HsT16992||PLA2G4B||cPLA2-beta||PHOSPHOLIPASE A2, CYTOSOLIC, CALCIUM-DEPENDENT, BETA||phospholipase A2, group IVB (cytosolic)|| | 0.677 | NM_005090 |
| PLA2G2A | ||PLA2G2A||MOM1||3.1.1.4||PLA2B||PLA2L||PLAS1||PLA2S||PHOSPHOLIPASE A2, SYNOVIAL||PHOSPHOLIPASE A2 POLYPEPTIDE B||MODIFIER OF MIN-1, MOUSE, HOMOLOG OF||phospholipase A2, group IIA (platelets, synovial fluid)|| | 0.662 | NM_000300 |
| PLA2G12A | ||PLA2G12A||phospholipase A2, group XIIA|| | 0.656 | NM_030821 |
| ALOX5 | ||5-@LIPOXYGENASE||1.13.11.34||LOG5||5-@LO||ALOX5||arachidonate 5-lipoxygenase|| | 0.643 | NM_000698 |
| LTB4DH | ||LTB4DH||MGC34943||leukotriene B4 12-hydroxydehydrogenase||NADP-dependent leukotriene B4 12-hydroxydehydrogenase|| | 0.599 | NM_012212 |
| PLA2G12A | ||PLA2G12A||phospholipase A2, group XIIA|| | 0.578 | NM_030821 |
| ALOX12B | ||ALOX12B||12R-LOX||12R-@LIPOXYGENASE||12-@LIPOXYGENASE, R TYPE||arachidonate 12-lipoxygenase, 12R type||ARACHIDONATE 12-LIPOXYGENASE, R TYPE|| | 0.549 | NM_001139 |
| LTB4DH | ||LTB4DH||MGC34943||leukotriene B4 12-hydroxydehydrogenase||NADP-dependent leukotriene B4 12-hydroxydehydrogenase|| | 0.535 | NM_012212 |
| PLA2G4A | ||3.1.1.4||3.1.1.5||cPLA2-alpha||PLA2G4A||PHOSPHOLIPASE A2, CYTOSOLIC, CALCIUM-DEPENDENT, ALPHA||phospholipase A2, group IVA (cytosolic, calcium-dependent)|| | 0.528 | NM_024420 |
| CYP4F3 | ||1.14.13.30||CYP4F3||CPF3||LTB4H||leukotriene-B4 20-monooxygenase||cytochrome P450-LTB-omega||LTB4 OMEGA-HYDROXYLASE||LEUKOTRIENE B4 OMEGA-HYDROXYLASE||cytochrome P450, family 4, subfamily F, polypeptide 3||cytochrome P450, subfamily IVF, polypeptide 3 (leukotriene B4 omega hydroxylase)|| | 0.476 | NM_000896 |
| LTB4DH | ||LTB4DH||MGC34943||leukotriene B4 12-hydroxydehydrogenase||NADP-dependent leukotriene B4 12-hydroxydehydrogenase|| | 0.358 | NM_012212 |
| AKR1C3 | ||HA1753||1.1.1.188||DD3||hluPGFS||HSD17B5||1.3.1.20||1.1.1.213||AKR1C3||KIAA0119||HAKRB||HAKRe||trans-1,2-dihydrobenzene-1,2-diol dehydrogenase||chlordecone reductase homolog||dihydrodiol dehydrogenase 3||prostaglandin F synthase||ALDO-KETO REDUCTASE B||3-@ALPHA-HYDROXYSTEROID DEHYDROGENASE, TYPE II||hydroxysteroid (17-beta) dehydrogenase 5||type IIb 3-alpha hydroxysteroid dehydrogenases||aldo-keto redu.. 1fe||hydronase | | |
| | P450-LTB-omega||LTB4 OMEGA-HYDROXYLASE||LEUKOTRIENE B4 OMEGA-HYDROXYLASE||cytochrome P450, family 4, subfamily F, polypeptide 3||cytochrome P450, subfamily IVF, polypeptide 3 (leukotriene B4 omega hydroxylase)|| | 0.476 | NM_000896 |
| LTB4DH | ||LTB4DH||MGC34943||leukotriene B4 12-hydroxydehydrogenase||NADP-dependent leukotriene B4 12 | | |

TABLE 9

| | Mast cell related genes | | |
|---|---|---|---|
| Common Name | Description | Fold Increase in EE | Genbank Accession number |
| ALOX15 | ||1.13.11.33||ALOX15||arachidonate 15-lipoxygenase||15-@LIPOXYGENASE, RETICULOCYTE ARACHIDONATE|| | 20.89 | NM_001140 |
| CXCL1 | ||MGSA-a||NAP-3||CXCL1||SCYB1||GROa||GRO1, FORMERLY||GRO PROTEIN, ALPHA||GRO1 ONCOGENE, FORMERLY||MELANOMA GROWTH STIMULATORY ACTIVITY, ALPHA||GRO1 oncogene (melanoma growth-stimulating activity)||CHEMOKINE, CXC MOTIF, LIGAND 1||GRO1 oncogene (melanoma growth stimulating activity, alpha)||SMALL INDUCIBLE CYTOKINE SUBFAMILY B, MEMBER 1||chemokine (C-X-C motif) ligand 1 (melanoma growth stimulating activity, alpha)|| | 18.79 | NM_001511 |
| CPA3 | ||CAP3||3.4.17.1||carboxypeptidase A3 (mast cell)||CARBOXYPEPTIDASE A3, MAST CELL||mast cell carboxypeptidase A3 precursor|| | 13.13 | NM_001870 |
| IL8 | ||NAP1||IL-8||LUCT/interleukin-8||LECT||K60||NAF||MONAP||LYNAP||TSG-1||b-ENAP||emoctakin||SCYB8||NAP-1||GCP1||IL8||MDNCF||GCP-1||CXCL8||AMCF-I||interleukin 8||protein 3-10C||beta-thromboglobulin-like protein||neutrophil-activating protein 1||interleukin 8 precursor||neutrophil-activating peptide 1||lymphocyte-derived neutrophil-activating factor||T cell chemotactic factor||monocyte-derived neutrophil chemotactic factor||CXC chemokine ligand 8||monocyte derived neutrophil-activating protein||granulocyte chemotactic protein 1||small inducible cytokine subfamily B, member 8|| | 7.071 | NM_000584 |
| TPSB2 | ||||TPS1||tryptase, alpha|| | 6.429 | NM_003294 |
| HRH1 | ||HRH1||H1-R||hisH1||histamine receptor H1||BPHS, MOUSE, HOMOLOG OF||histamine receptor, subclass H1|| | 6.191 | NM_000861 |
| TPSB2 | ||||TPS1||tryptase, alpha|| | 6.028 | NM_003294 |
| TPSB2 | ||||TPS1||tryptase, alpha|| | 5.573 | NM_003294 |
| PGDS | ||PGDS||5.3.99.2||prostaglandin-D synthase||prostaglandin D2 synthase, hematopoietic||hematopoietic prostaglandin D2 synthase|| | 5.265 | NM_014485 |
| HS3ST1 | ||HS3ST1||3OST1||2.8.2.23||heparin-glucosamine 3-O-sulfotransferase||heparan sulfate (glucosamine) 3-O-sulfotransferase 1||heparan sulfate D-glucosaminyl 3-O-sulfotransferase 1 precursor|| | 4.249 | NM_005114 |
| MS4A2 | ||FCERI||MS4A1||MS4A2||FCER1B||Fc epsilon receptor I beta-chain||Fc IgE RECEPTOR, BETA CHAIN||MEMBRANE-SPANNING 4 DOMAINS, SUBFAMILY A, MEMBER 2||immunoglobulin E receptor, high affinity, beta polypeptide||Fc FRAGMENT OF IgE, HIGH AFFINITY I, RECEPTOR FOR, BETA SUBUNIT||membrane-spanning 4-domains, subfamily A, member 2 (Fc fragment of IgE, high affinity I, receptor for; beta polypeptide)|| | 4.192 | NM_000139 |
| CXCR4 | CXCR4 | 4.092 | AJ224869 |
| TPSB2 | ||||TPS1||tryptase, alpha|| | 4.033 | NM_003294 |
| TPSB2 | ||||TPS1||tryptase, alpha|| | 3.98 | NM_003294 |
| PRG1 | ||MGC9289||PPG||serglycin||PRG1||hematopoetic proteoglycan core peptide||platelet proteoglycan protein | 3.444 | NM_002727 |

TABLE 9-continued

Mast cell related genes

| Common Name | Description | Fold Increase in EE | Genbank Accession number |
|---|---|---|---|
| PRG1 | core\|\|proteoglycan 1, secretory granule\|\|secretory granule proteoglycan core peptide\|\|proteoglycan 1, secretory granule precursor\|\|proteoglycan protein core for mast cell secretory granule\|\|\|\|MGC9289\|\|PPG\|\|serglycin\|\|PRG1\|\|hematopoetic proteoglycan core peptide\|\|platelet proteoglycan protein core\|\|proteoglycan 1, secretory granule\|\|secretory granule proteoglycan core peptide\|\|proteoglycan 1, secretory granule precursor\|\|proteoglycan protein core for mast cell secretory granule\|\| | 3.441 | NM_002727 |
| TPSB2 | \|\|\|\|TPS1\|\|tryptase, alpha\|\| | 3.188 | NM_003294 |
| ADAMDEC1 | \|\|M12.219\|\|ADAMDEC1\|\|disintegrin protease\|\|ADAM-like, decysin 1\|\|ADAM-LIKE PROTEIN DECYSIN 1\|\|A DISINTEGRIN AND METALLOPROTEINASE DOMAIN-LIKE PROTEIN DECYSIN 1\|\| | 3.118 | NM_014479 |
| TPSB2 | \|\|\|\|TPS1\|\|tryptase, alpha\|\| | 2.997 | NM_003294 |
| IL15 | \|\|IL-15\|\|IL15\|\|MGC9721\|\|interleukin 15\|\|interleukin 15 isoform 2 precursor\|\|interleukin 15 isoform 1 precursor\|\| | 2.879 | NM_172174 |
| PTGES | \|\|PGES\|\|TP53I12\|\|MGST1L1\|\|PP1294\|\|PP102\|\|PTGES\|\|MGC10317\|\|PIG12\|\|MGST1-L1\|\|MGST-IV\|\|MGST1-like 1\|\|p53-INDUCED GENE 12\|\|prostaglandin E synthase\|\|p53-induced apoptosis protein 12\|\|prostaglandin E synthase isoform 2\|\|prostaglandin E synthase isoform 1\|\|microsomal glutathione S-transferase 1-like 1\|\|tumor protein p53 inducible protein 12\|\| | 2.822 | NM_198797 |
| KIT | \|\|2.7.1.112\|\|CD117\|\|SCFR\|\|PBT\|\|KIT\|\|KIT ONCOGENE\|\|STEM CELL FACTOR RECEPTOR\|\|MAST CELL GROWTH FACTOR RECEPTOR\|\|v-kit Hardy-Zuckerman 4 feline sarcoma viral oncogene homolog\|\|v-kit Hardy-Zuckerman 4 feline sarcoma viral oncogene homolog precursor\|\| | 2.754 | NM_000222 |
| VCAM1 | \|\|VCAM1\|\|INCAM-100\|\|CD106 antigen\|\|vascular cell adhesion molecule 1\|\|vascular cell adhesion molecule 1 isoform b precursor\|\|vascular cell adhesion molecule 1 isoform a precursor\|\| | 2.355 | NM_001078 |
| ITGAM | \|\|ITGAM\|\|MAC1A\|\|MO1A\|\|CR3A\|\|MAC-1\|\|Mo1, ALPHA SUBUNIT\|\|Mac1, ALPHA SUBUNIT\|\|integrin alpha M precursor\|\|neutrophil adherence receptor alpha-M subunit\|\|COMPLEMENT RECEPTOR TYPE 3, ALPHA SUBUNIT\|\|Integrin, alpha-M (complement component receptor-3, alpha; antigen CD11B (p170); macrophage antigen, alpha polypeptide)\|\|integrin, alpha M (complement component receptor 3, alpha; also known as CD11b (p170), macrophage antigen alpha polypeptide)\|\| | 2.246 | NM_000632 |
| LTA4H | \|\|3.3.2.6\|\|LTA4H\|\|leukotriene A4 hydrolase\|\| | 2.205 | NM_000895 |
| IL1F9 | \|\|IL1H1\|\|IL1F9\|\|IL1RP2\|\|INTERLEUKIN 1-RELATED PROTEIN 2\|\|INTERLEUKIN 1 HOMOLOG 1\|\|interleukin 1 family, member 9\|\| | 2.109 | NM_019618 |
| FCER1G | \|\|FCER1G\|\|Fc IgE RECEPTOR, GAMMA CHAIN\|\|immunoglobulin E receptor, high affinity, gamma chain\|\|IMMUNOGLOBULIN E RECEPTOR, | 2.057 | NM_004106 |

TABLE 9-continued

Mast cell related genes

| Common Name | Description | Fold Increase in EE | Genbank Accession number |
|---|---|---|---|
| | HIGH-AFFINITY, OF MAST CELLS, GAMMA POLYPEPTIDE\|\|Fc fragment of IgE, high affinity I, receptor for; gamma polypeptide\|\|Fc FRAGMENT OF IgE, HIGH AFFINITY I, RECEPTOR FOR, GAMMA SUBUNIT\|\|Fc fragment of IgE, high affinity I, receptor for, gamma polypeptide precursor\|\| | | |
| IL18R1 | \|\|IL-1Rrp\|\|IL1RRP\|\|IL18R1\|\|IL1 receptor-related protein\|\|interleukin 18 receptor 1\|\|interleukin 18 receptor 1 precursor\|\| | 2.047 | NM_003855 |
| CCL18 | \|\|CCL18\|\|DC-CK1\|\|AMAC1\|\|AMAC-1\|\|MIP-4\|\|CKb7\|\|PARC\|\|DCCK1\|\|SCYA18, FORMERLY\|\|chemokine (C-C), dendritic\|\|pulmonary and activation-regulated chemokine\|\|CC chemokine ligand 18\|\|macrophage inflammatory protein 4\|\|dendritic cell chemokine 1\|\|small inducible cytokine A18 precursor\|\|CHEMOKINE, CC MOTIF, LIGAND 18\|\|alternative macrophage activation-associated CC chemokine 1\|\|SMALL INDUCIBLE CYTOKINE SUBFAMILY A, MEMBER 18, FORMERLY\|\|chemokine (C-C motif) ligand 18 (pulmonary and activation-regulated)\|\|small inducible cytokine subfamily A (Cys-Cys), member 18\|\| | 2.003 | NM_002988 |
| FCER1G | \|\|FCER1G\|\|Fc IgE RECEPTOR, GAMMA CHAIN\|\|immunoglobulin E receptor, high affinity, gamma chain\|\|IMMUNOGLOBULIN E RECEPTOR, HIGH-AFFINITY, OF MAST CELLS, GAMMA POLYPEPTIDE\|\|Fc fragment of IgE, high affinity I, receptor for; gamma polypeptide\|\|Fc FRAGMENT OF IgE, HIGH AFFINITY I, RECEPTOR FOR, GAMMA SUBUNIT\|\|Fc fragment of IgE, high affinity I, receptor for, gamma polypeptide precursor\|\| | 2 | NM_004106 |
| CCL18 | \|\|CCL18\|\|DC-CK1\|\|AMAC1\|\|AMAC-1\|\|MIP-4\|\|CKb7\|\|PARC\|\|DCCK1\|\|SCYA18, FORMERLY\|\|chemokine (C-C), dendritic\|\|pulmonary and activation-regulated chemokine\|\|CC chemokine ligand 18\|\|macrophage inflammatory protein 4\|\|dendritic cell chemokine 1\|\|small inducible cytokine A18 precursor\|\|CHEMOKINE, CC MOTIF, LIGAND 18\|\|alternative macrophage activation-associated CC chemokine 1\|\|SMALL INDUCIBLE CYTOKINE SUBFAMILY A, MEMBER 18, FORMERLY\|\|chemokine (C-C motif) ligand 18 (pulmonary and activation-regulated)\|\|small inducible cytokine subfamily A (Cys-Cys), member 18\|\| | 1.933 | NM_002988 |
| TGFBI | \|\|CDG2\|\|kerato-epithelin\|\|BETA-IG-H3\|\|CDB1\|\|LCD1\|\|CDGG1\|\|CSD1\|\|CSD2\|\|CSD3\|\|TGFBI\|\|BIGH3\|\|KERATOEPITHELIN\|\|corneal dystrophy\|\|TRANSFORMING GROWTH FACTOR, BETA-INDUCED, 68-KD\|\|transforming growth factor, beta-induced, 68 kDa\|\| | 1.92 | NM_000358 |
| CD209 | \|\|CDSIGN\|\|CD209\|\|DC-SIGN1\|\|DCSIGN\|\|CD209 antigen\|\|HIV GP120-BINDING PROTEIN\|\|dendritic cell-specific ICAM3-grabbing nonintegrin\|\| | 1.903 | NM_021155 |

TABLE 9-continued

Mast cell related genes

| Common Name | Description | Fold Increase in EE | Genbank Accession number |
|---|---|---|---|
| FGF11 | \|\|FGF11\|\|MGC45269\|\|FHF3\|\|fibroblast growth factor 11\|\|fibroblast growth factor homologous factor 3\|\| | 1.868 | NM_004112 |
| TNFRSF5 | \|\|Bp50\|\|TNFRSF5\|\|MGC9013\|\|CDW40\|\|CD40 antigen\|\|CD40L receptor\|\|B CELL-ASSOCIATED MOLECULE CD40\|\|CD40 type II isoform\|\|B cell surface antigen CD40\|\|nerve growth factor receptor-related B-lymphocyte activation molecule\|\|tumor necrosis factor receptor superfamily, member 5\|\|tumor necrosis factor receptor superfamily, member 5 isoform 2 precursor\|\|tumor necrosis factor receptor superfamily, member 5 isoform 1 precursor\|\| | 1.862 | NM_001250 |
| C3AR1 | \|\|HNFAG09\|\|C3AR1\|\|AZ3B\|\|COMPLEMENT COMPONENT 3a RECEPTOR 1\|\|complement component 3 receptor 1\|\| | 1.843 | NM_004054 |
| IL15RA | \|\|IL15RA\|\|interleukin 15 receptor, alpha\|\|interleukin 15 receptor, alpha isoform 2\|\|interleukin 15 receptor, alpha isoform 1 precursor\|\| | 1.771 | NM_172200 |
| IL2RG | \|\|IL2RG\|\|IMD4\|\|SCIDX1\|\|CD132 ANTIGEN\|\|Interleukin-2 receptor, gamma\|\|common cytokine receptor gamma chain\|\|interleukin 2 receptor, gamma chain, precursor\|\|interleukin 2 receptor, gamma (severe combined immunodeficiency)\|\| | 1.739 | NM_000206 |
| TNFRSF5 | \|\|Bp50\|\|TNFRSF5\|\|MGC9013\|\|CDW40\|\|CD40 antigen\|\|CD40L receptor\|\|B CELL-ASSOCIATED MOLECULE CD40\|\|CD40 type II isoform\|\|B cell surface antigen CD40\|\|nerve growth factor receptor-related B-lymphocyte activation molecule\|\|tumor necrosis factor receptor superfamily, member 5\|\|tumor necrosis factor receptor superfamily, member 5 isoform 2 precursor\|\|tumor necrosis factor receptor superfamily, member 5 isoform 1 precursor\|\| | 1.706 | NM_001250 |
| ALOX5AP | \|\|FLAP\|\|ALOX5AP\|\|5-@LIPOXYGENASE-ACTIVATING PROTEIN\|\|MK-886-binding protein\|\|FIVE-LIPOXYGENASE-ACTIVATING PROTEIN\|\|arachidonate 5-lipoxygenase-activating protein\|\|five-lipoxygenase activating protein\|\| | 1.646 | NM_001629 |
| IL12RB1 | \|\|MGC34454\|\|IL-12R-BETA1\|\|IL12RB1\|\|interleukin-12 receptor beta-1 chain\|\|IL-12 receptor beta component\|\|INTERLEUKIN 12 RECEPTOR, BETA-1\|\|interleukin 12 receptor, beta 1\|\|interleukin 12 receptor, beta 1 isoform 1 precursor\|\|interleukin 12 receptor, beta 1 isoform 2 precursor\|\| | 1.588 | NM_005535 |
| CCL5 | \|\|TCP228\|\|MGC17164\|\|CCL5\|\|D17S136E\|\|SIS-delta\|\|SISd\|\|SCYA5, FORMERLY\|\|T CELL-SPECIFIC RANTES\|\|beta-chemokine RANTES precursor\|\|T-cell specific RANTES protein\|\|T CELL-SPECIFIC PROTEIN p228\|\|T-cell specific protein p288\|\|CHEMOKINE, CC MOTIF, LIGAND 5\|\|SMALL INDUCIBLE CYTOKINE A5, FORMERLY\|\|small inducible cytokine A5 precursor\|\|chemokine (C-C motif) ligand 5\|\|small inducible cytokine subfamily A (Cys-Cys), member 5\|\|regulated upon activation, normally T-expressed, and presumably secreted\|\| | 1.56 | NM_002985 |

TABLE 9-continued

Mast cell related genes

| Common Name | Description | Fold Increase in EE | Genbank Accession number |
|---|---|---|---|
| CCR1 | \|\|CMKBR1\|\|CCR1\|\|MIP1aR\|\|CKR-1\|\|CKR1\|\|HM145\|\|MACROPHAGE INFLAMMATORY PROTEIN 1-ALPHA/RANTES RECEPTOR\|\|chemokine (C-C motif) receptor 1\|\|CHEMOKINE, CC MOTIF, RECEPTOR 1\|\| | 1.525 | NM_001295 |
| GZMA | \|\|HFSP\|\|3.4.21.78\|\|CTLA3\|\|GZMA\|\|CTL tryptase\|\|granzyme A precursor\|\|granzyme A (granzyme 1, cytotoxic T-lymphocyte-associated serine esterase 3)\|\|CYTOLYTIC T CELL- AND NATURAL KILLER CELL-SPECIFIC TRYPSIN-LIKE SERINE PROTEASE\|\|Granzyme A (Cytotoxic T-lymphocyte-associated serine esterase-3; Hanukah factor serine protease)\|\| | 1.509 | NM_006144 |
| IFNAR2 | \|\|IFNABR\|\|IFNAR2\|\|human interferon alpha/beta receptor\|\|INTERFERON, ALPHA, BETA, AND OMEGA, RECEPTOR 2\|\|interferon (alpha, beta and omega) receptor 2\|\| | 1.503 | NM_000874 |
| LTBP1 | \|\|LTBP1\|\|TGF-beta1-BP-1\|\|LATENT TRANSFORMING GROWTH FACTOR-BETA-BINDING PROTEIN 1\|\|latent transforming growth factor beta binding protein 1\|\|latent transforming growth factor beta binding protein 1 precursor\|\| | 1.503 | NM_000627 |
| IFNGR1 | \|\|IFNGR1\|\|CD119 ANTIGEN\|\|AVP, TYPE II\|\|IMMUNE INTERFERON RECEPTOR 1\|\|interferon gamma receptor 1\|\|Immune interferon, receptor for\|\|ANTIVIRAL PROTEIN, TYPE II\|\|INTERFERON, GAMMA, RECEPTOR 1\|\| | 1.498 | NM_000416 |
| FCGR1A | \|\|FCGR1A\|\|FCRI\|\|IGFR1\|\|Fc-gamma receptor I A1\|\|IMMUNOGLOBULIN G Fc RECEPTOR I\|\|Fc fragment of IgG, high affinity Ia, receptor for (CD64)\|\| | 1.489 | NM_000566 |
| ADORA3 | \|\|\|\|ADORA3\|\|adenosine A3 receptor\|\| | 1.481 | NM_000677 |
| IL1RL1 | \|\|ST2L\|\|DER4\|\|IL1RL1\|\|ST2V\|\|FIT-1\|\|MGC32623\|\|T1\|\|ST2 protein\|\|interleukin 1 receptor-related protein\|\|interleukin 1 receptor-like 1\|\|GROWTH STIMULATION-EXPRESSED GENE, MOUSE, HOMOLOG OF\|\|homolog of mouse growth stimulation-expressed gene\|\|interleukin 1 receptor-like 1 isoform 1 precursor\|\|interleukin 1 receptor-like 1 isoform 2 precursor\|\|interleukin 1 receptor-like 1 isoform 3 precursor\|\| | 1.479 | NM_173459 |
| PTGDS | \|\|PGDS2\|\|PTGDS\|\|PDS\|\|5.3.99.2\|\|prostaglandin-H2 D-isomerase\|\|PGD2 synthase\|\|beta-trace protein\|\|glutathione-independent PGD synthase\|\|PROSTAGLANDIN D2 SYNTHASE, BRAIN\|\|lipocalin-type prostaglandin D synthase\|\|prostaglandin D2 synthase 21 kDa (brain)\|\| | 1.475 | NM_000954 |
| CCL5 | \|\|TCP228\|\|MGC17164\|\|CCL5\|\|D17S136E\|\|SIS-delta\|\|SISd\|\|SCYA5, FORMERLY\|\|T CELL-SPECIFIC RANTES\|\|beta-chemokine RANTES precursor\|\|T-cell specific RANTES protein\|\|T CELL-SPECIFIC PROTEIN p228\|\|T-cell specific protein p288\|\|CHEMOKINE, CC MOTIF, LIGAND 5\|\|SMALL INDUCIBLE CYTOKINE A5, FORMERLY\|\|small inducible cytokine A5 precursor\|\|chemokine (C-C motif) ligand 5\|\|small inducible cytokine subfamily A (Cys-Cys), member 5\|\|regulated upon activation, normally T-expressed, and presumably secreted\|\| | 1.457 | NM_002985 |

TABLE 9-continued

Mast cell related genes

| Common Name | Description | Fold Increase in EE | Genbank Accession number |
| --- | --- | --- | --- |
| HS3ST3A1 | \|\|HS3ST3A1\|\|2.8.2.23\|\|3OST3A1\|\|3OST3A1\|\|heparin-glucosamine 3-O-sulfotransferase\|\|heparan sulfate D-glucosaminyl 3-O-sulfotransferase 3A1\|\|heparan sulfate (glucosamine) 3-O-sulfotransferase 3A1\|\| | 1.441 | NM_006042 |
| CCL4 | \|\|Act-2\|\|MIP1B1\|\|ACT2\|\|LAG1\|\|CCL4\|\|MIP-1-beta\|\|AT744.1\|\|SCYA4, FORMERLY\|\|lymphocyte-activation gene 1\|\|IMMUNE ACTIVATION 2\|\|MACROPHAGE INFLAMMATORY PROTEIN 1-BETA\|\|SMALL INDUCIBLE CYTOKINE A4, FORMERLY\|\|chemokine (C-C motif) ligand 4\|\|CHEMOKINE, CC MOTIF, LIGAND 4\|\|chemokine (C-C motif) ligand 4 precursor\|\|small inducible cytokine A4 (homologous to mouse Mip-1b)\|\| | 1.44 | NM_002984 |
| CXCR4 | \|\|HM89\|\|LAP3\|\|NPYY3R\|\|LESTR\|\|HSY3RR\|\|CXCR4\|\|WHIM\|\|D2S201E\|\|NPY3R\|\|NPYR\|\|LIPOPOLYSACCHARIDE-ASSOCIATED PROTEIN 3\|\|LEUKOCYTE-DERIVED SEVEN-TRANSMEMBRANE-DOMAIN RECEPTOR\|\|LPS-ASSOCIATED PROTEIN 3\|\|SEVEN-TRANSMEMBRANE-SEGMENT RECEPTOR, SPLEEN\|\|Neuropeptide Y receptor Y3\|\|chemokine (C-X-C motif) receptor 4\|\|CHEMOKINE, CXC MOTIF, RECEPTOR 4\|\|chemokine (C-X-C motif), receptor 4 (fusin)\|\| | 1.438 | NM_003467 |
| CCL13 | \|\|CCL13\|\|MGC17134\|\|NCC1\|\|CK-beta-10\|\|SCYL1\|\|NCC-1\|\|MCP-4\|\|MCP4\|\|CKb10\|\|SCYA13, FORMERLY\|\|new CC chemokine 1\|\|monocyte chemoattractant protein 4\|\|monocyte chemotactic protein 4\|\|chemokine (C-C motif) ligand 13\|\|CHEMOKINE, CC MOTIF, LIGAND 13\|\|small inducible cytokine A13 precursor\|\|SMALL INDUCIBLE CYTOKINE SUBFAMILY A, MEMBER 13, FORMERLY\|\|small inducible cytokine subfamily A (Cys-Cys), member 13\|\| | 1.435 | NM_005408 |
| CXCR4 | \|\|HM89\|\|LAP3\|\|NPYY3R\|\|LESTR\|\|HSY3RR\|\|CXCR4\|\|WHIM\|\|D2S201E\|\|NPY3R\|\|NPYR\|\|LIPOPOLYSACCHARIDE-ASSOCIATED PROTEIN 3\|\|LEUKOCYTE-DERIVED SEVEN-TRANSMEMBRANE-DOMAIN RECEPTOR\|\|LPS-ASSOCIATED PROTEIN 3\|\|SEVEN-TRANSMEMBRANE-SEGMENT RECEPTOR, SPLEEN\|\|Neuropeptide Y receptor Y3\|\|chemokine (C-X-C motif) receptor 4\|\|CHEMOKINE, CXC MOTIF, RECEPTOR 4\|\|chemokine (C-X-C motif), receptor 4 (fusin)\|\| | 1.427 | NM_003467 |
| IL8 | \|\|NAP1\|\|IL-8\|\|LUCT/interleukin-8\|\|LECT\|\|K60\|\|NAF\|\|MONAP\|\|LYNAP\|\|TSG-1\|\|b-ENAP\|\|emoctakin\|\|SCYB8\|\|NAP-1\|\|GCP1\|\|IL8\|\|MDNCF\|\|GCP-1\|\|CXCL8\|\|AMCF-I\|\|interleukin 8\|\|protein 3-10C\|\|beta-thromboglobulin-like protein\|\|neutrophil-activating protein 1\|\|interleukin 8 precursor\|\|neutrophil-activating peptide 1\|\|lymphocyte-derived neutrophil-activating factor\|\|T cell chemotactic factor\|\|monocyte-derived neutrophil chemotactic factor\|\|CXC chemokine ligand 8\|\|monocyte derived neutrophil- | 1.404 | NM_000584 |

TABLE 9-continued

Mast cell related genes

| Common Name | Description | Fold Increase in EE | Genbank Accession number |
|---|---|---|---|
| | activating protein\|\|granulocyte chemotactic protein 1\|\|small inducible cytokine subfamily B, member 8\|\| | | |
| MIST | \|\|MIST\|\|mast cell immunoreceptor signal transducer\|\| | 1.383 | XM_093920 |
| IL2RB | \|\|IL2RB\|\|P70-75\|\|CD122 antigen\|\|interleukin 2 receptor, beta\|\|interleukin 2 receptor beta precursor\|\|high affinity IL-2 receptor beta subunit\|\| | 1.381 | NM_000878 |
| PTGDS | \|\|PGDS2\|\|PTGDS\|\|PDS\|\|5.3.99.2\|\|prostaglandin-H2 D-isomerase\|\|PGD2 synthase\|\|beta-trace protein\|\|glutathione-independent PGD synthase\|\|PROSTAGLANDIN D2 SYNTHASE, BRAIN\|\|lipocalin-type prostaglandin D synthase\|\|prostaglandin D2 synthase 21 kDa (brain)\|\| | 1.334 | NM_000954 |
| CCL2 | \|\|SMC-CF\|\|CCL2\|\|MCP1\|\|MCAF\|\|SCYA2\|\|MCP-1\|\|MGC9434\|\|GDCF-2 HC11\|\|monocyte chemoattractant protein-1\|\|monocyte secretory protein JE\|\|small inducible cytokine A2 precursor\|\|monocyte chemotactic and activating factor\|\|chemokine (C-C motif) ligand 2\|\|small inducible cytokine subfamily A (Cys-Cys), member 2\|\|monocyte chemotactic protein 1, homologous to mouse Sig-je\|\| | 1.307 | NM_002982 |
| CMA1 | \|\|CYH\|\|3.4.21.39\|\|CMA1\|\|MCT1\|\|chymase, heart\|\|chymase, mast cell\|\|mast cell protease I\|\|chymase 1, mast cell\|\|chymase 1, mast cell preproprotein\|\| | 1.263 | NM_001836 |
| GZMK | \|\|TRYP2\|\|GZMK\|\|3.4.21.—\|\|PRSS\|\|granzyme K precursor\|\|granzyme K (serine protease, granzyme 3)\|\|granzyme K (serine protease, granzyme 3; tryptase II)\|\| | 1.255 | NM_002104 |
| PRG1 | \|\|MGC9289\|\|PPG\|\|serglycin\|\|PRG1\|\|hematopoetic proteoglycan core peptide\|\|platelet proteoglycan protein core\|\|proteoglycan 1, secretory granule\|\|secretory granule proteoglycan core peptide\|\|proteoglycan 1, secretory granule precursor\|\|proteoglycan protein core for mast cell secretory granule\|\| | 1.23 | NM_002727 |
| KITLG | \|\|KITLG\|\|KL-1\|\|SCF\|\|SF\|\|KIT ligand\|\|STEEL FACTOR\|\|STEEL, MOUSE, HOMOLOG OF\|\|stem cell factor precursor\|\|MGF STEM CELL FACTOR\|\|mast cell growth factor\|\|KIT ligand isoform a, precursor\|\|KIT ligand isoform b, precursor\|\| | 1.208 | NM_000899 |
| CXCL2 | \|\|MIP2A\|\|GROb\|\|MGSA-b\|\|MIP2-ALPHA\|\|SCYB2\|\|CXCL2\|\|MIP-2a\|\|CINC-2a\|\|GRO2, FORMERLY\|\|GRO PROTEIN, BETA\|\|GRO2 ONCOGENE, FORMERLY\|\|MACROPHAGE INFLAMMATORY PROTEIN 2\|\|chemokine (C-X-C motif) ligand 2\|\|CHEMOKINE, CXC MOTIF, LIGAND 2\|\|SMALL INDUCIBLE CYTOKINE SUBFAMILY B, MEMBER 2\|\| | 1.194 | NM_002089 |
| KITLG | \|\|KITLG\|\|KL-1\|\|SCF\|\|SF\|\|KIT ligand\|\|STEEL FACTOR\|\|STEEL, MOUSE, HOMOLOG OF\|\|stem cell factor precursor\|\|MGF STEM CELL FACTOR\|\|mast cell growth factor\|\|KIT ligand isoform a, precursor\|\|KIT ligand isoform b, precursor\|\| | 1.169 | NM_000899 |

TABLE 9-continued

Mast cell related genes

| Common Name | Description | Fold Increase in EE | Genbank Accession number |
|---|---|---|---|
| FCER1A | \|\|FCER1A\|\|FCE1A\|\|FcERI\|\|Fc-epsilon RI-alpha\|\|Fc IgE receptor, alpha polypeptide\|\|Fc IgE RECEPTOR, ALPHA CHAIN\|\|high affinity immunoglobulin epsilon receptor alpha-subunit\|\|immunoglobulin E receptor, high-affinity, of mast cells, alpha polypeptide\|\|Fc fragment of IgE, high affinity I, receptor for; alpha polypeptide\|\|Fc FRAGMENT OF IgE, HIGH AFFINITY I, RECEPTOR FOR, ALPHA SUBUNIT\|\|Fc fragment of IgE, high affinity I, receptor for; alpha polypeptide precursor\|\| | 1.121 | NM_002001 |
| TGFB1 | \|\|DPD1\|\|TGFB1\|\|TGF-BETA\|\|CED\|\|TRANSFORMING GROWTH FACTOR, BETA-1\|\|diaphyseal dysplasia 1, progressive (Camurati-Engelmann disease)\|\|transforming growth factor, beta 1 (Camurati-Engelmann disease)\|\| | 1.078 | NM_000660 |
| IL3 | \|\|IL-3\|\|IL3\|\|MCGF\|\|MULTI-CSF\|\|multilineage-colony-stimulating factor\|\|P-cell stimulating factor\|\|hematopoietic growth factor\|\|mast-cell growth factor\|\|interleukin 3 precursor\|\|interleukin 3 (colony-stimulating factor, multiple)\|\| | 1.009 | NM_000588 |
| KLRG1 | \|\|KLRG1\|\|MAFA-2F1\|\|MAFAL\|\|MAFA-LIKE\|\|mast cell function-associated antigen (ITIM-containing)\|\|MAST CELL FUNCTION-ASSOCIATED ANTIGEN, RAT, HOMOLOG OF\|\|KILLER CELL LECTIN-LIKE RECEPTOR, SUBFAMILY G, MEMBER 1\|\|killer cell lectin-like receptor subfamily G, member 1\|\| | 0.993 | NM_005810 |
| TPSD1 | \|\|TPSD1\|\|mMCP-7-like-1\|\|mMCP-7-like-2\|\|hmMCP-7-like\|\|mast cell tryptase\|\|tryptase delta 1\|\| | 0.991 | NM_012217 |
| MIST | \|\|MIST\|\|mast cell immunoreceptor signal transducer\|\| | 0.989 | XM_093920 |
| TPSG1 | \|\|TMT\|\|3.4.21.59\|\|PRSS31\|\|TPSG1\|\|pituitary tryptase\|\|skin tryptase\|\|lung tryptase\|\|gamma II\|\|mast cell tryptase\|\|transmembrane tryptase preproprotein\|\|tryptase gamma 1\|\|mast cell protease II\|\| | 0.963 | NM_012467 |
| TPSG1 | \|\|TMT\|\|3.4.21.59\|\|PRSS31\|\|TPSG1\|\|pituitary tryptase\|\|skin tryptase\|\|lung tryptase\|\|gamma II\|\|mast cell tryptase\|\|transmembrane tryptase preproprotein\|\|tryptase gamma 1\|\|mast cell protease II\|\| | 0.949 | NM_012467 |
| IL9 | \|\|IL-9\|\|IL9\|\|HP40\|\|interleukin 9\|\|p40 protein\|\|p40 cytokine\|\|interleukin 9 precursor\|\|T-cell growth factor p40\|\|T-CELL/MAST CELL GROWTH FACTOR P40\|\|p40 T-cell and mast cell growth factor\|\|homolog of mouse T cell and mast cell growth factor 40\|\| | 0.886 | NM_000590 |
| IL1RAP | \|\|IL-1RAcP\|\|IL1R3\|\|IL1RAP\|\|IL1RAcP\|\|interleukin 1 receptor accessory protein\|\|interleukin 1 receptor accessory protein isoform 1\|\|interleukin 1 receptor accessory protein isoform 2\|\| | 0.764 | NM_002182 |
| IL1RL2 | \|\|IL1R-rp2\|\|IL1RL2\|\|IL1RRP2\|\|interleukin-1 receptor-related protein 2\|\|interleukin 1 receptor-like 2\|\|interleukin 1 receptor-like 2 precursor\|\| | 0.71 | NM_003854 |
| FGFBP1 | \|\|FGFBP1\|\|HBP17\|\|HBGF-BINDING PROTEIN, 17-KD\|\|FGF-BINDING PROTEIN 1\|\|FIBROBLAST GROWTH | 0.7 | NM_005130 |

TABLE 9-continued

Mast cell related genes

| Common Name | Description | Fold Increase in EE | Genbank Accession number |
|---|---|---|---|
| | FACTOR-BINDING PROTEIN 1\|\|HEPARIN-BINDING GROWTH FACTOR-BINDING PROTEIN, 17-KD\|\|heparin-binding growth factor binding protein\|\| | | |
| ALOX5 | \|\|5-@LIPOXYGENASE\|\|1.13.11.34\|\|LOG5\|\|5-@LO\|\|ALOX5\|\|arachidonate 5-lipoxygenase\|\| | 0.679 | NM_000698 |
| MCP | \|\|MCP\|\|MGC26544\|\|TLX\|\|MIC10\|\|TRA2.10\|\|CD46 antigen\|\|measles virus receptor\|\|CD46 MEASLES, SUSCEPTIBILITY TO\|\|complement membrane cofactor protein\|\|trophoblast leucocyte common antigen\|\|membrane cofactor protein isoform 6 precursor\|\|membrane cofactor protein isoform 9 precursor\|\|membrane cofactor protein isoform 11 precursor\|\|membrane cofactor protein isoform 14 precursor\|\|membrane cofactor protein isoform 2 precursor\|\|membrane cofactor protein isoform 5 precursor\|\|membrane cofactor protein isoform 8 precursor\|\|antigen identified by monoclonal antibody TRA-2-10\|\|membrane cofactor protein isoform 12 precursor\|\|membrane cofactor protein isoform 10 precursor\|\|membrane cofactor protein isoform 13 precursor\|\|membrane cofactor protein isoform 3 precursor\|\|membrane cofactor protein isoform 1 precursor\|\|membrane cofactor protein isoform 4 precursor\|\|membrane cofactor protein isoform 7 precursor\|\|membrane cofactor protein (CD46, trophoblast-lymphocyte cross-reactive antigen)\|\| | 0.645 | NM_002389 |
| ALOX5 | \|\|5-@LIPOXYGENASE\|\|1.13.11.34\|\|LOG5\|\|5-@LO\|\|ALOX5\|\|arachidonate 5-lipoxygenase\|\| | 0.643 | NM_000698 |
| HNMT | \|\|HNMT\|\|2.1.1.8\|\|histamine N-methyltransferase\|\| | 0.618 | NM_006895 |
| IL1A | \|\|hematopoietin-1\|\|IL1-ALPHA\|\|IL-1A\|\|IL1A\|\|IL1F1\|\|INTERLEUKIN 1-ALPHA\|\|preinterleukin 1 alpha\|\|interleukin 1, alpha\|\|interleukin 1, alpha proprotein\|\| | 0.606 | NM_000575 |
| HNMT | \|\|HNMT\|\|2.1.1.8\|\|histamine N-methyltransferase\|\| | 0.604 | NM_006895 |
| ALOX12B | \|\|ALOX12B\|\|12R-LOX\|\|12R-@LIPOXYGENASE\|\|12-@LIPOXYGENASE, R TYPE\|\|arachidonate 12-lipoxygenase, 12R type\|\|ARACHIDONATE 12-LIPOXYGENASE, R TYPE\|\| | 0.549 | NM_001139 |
| LTB4DH | \|\|LTB4DH\|\|MGC34943\|\|leukotriene B4 12-hydroxydehydrogenase\|\|NADP-dependent leukotriene B4 12-hydroxydehydrogenase\|\| | 0.535 | NM_012212 |
| PTN | \|\|HARP\|\|HBNF\|\|NEGF1\|\|PTN\|\|HBGF8\|\|heparin-binding growth-associated molecule\|\|NEURITE OUTGROWTH-PROMOTING FACTOR, HEPARIN-BINDING\|\|HEPARIN-BINDING GROWTH FACTOR 8\|\|heparin affin regulatory protein\|\|pleiotrophin (heparin binding growth factor 8, neurite growth-promoting factor 1)\|\| | 0.477 | NM_002825 |

TABLE 9-continued

Mast cell related genes

| Common Name | Description | Fold Increase in EE | Genbank Accession number |
|---|---|---|---|
| CYP4F3 | \|\|1.14.13.30\|\|CYP4F3\|\|CPF3\|\|LTB4H\|\|leukotriene-B4 20-monooxygenase\|\|cytochrome P450-LTB-omega\|\|LTB4 OMEGA-HYDROXYLASE\|\|LEUKOTRIENE B4 OMEGA-HYDROXYLASE\|\|cytochrome P450, family 4, subfamily F, polypeptide 3\|\|cytochrome P450, subfamily IVF, polypeptide 3 (leukotriene B4 omega hydroxylase)\|\| | 0.476 | NM_000896 |
| PDGFRA | \|\|CD140a\|\|Alpha platelet-derived growth factor receptor precursor | 0.474 | NM_006206 |
| IL1F6 | \|\|FIL1E\|\|IL-1F6\|\|FIL1-EPSILON\|\|IL1F6\|\|FIL1(EPSILON)\|\|interleukin 1, epsilon\|\|family of interleukin 1-epsilon\|\|interleukin 1 family, member 6 (epsilon)\|\| | 0.47 | NM_014440 |
| PTN | \|\|HARP\|\|HBNF\|\|NEGF1\|\|PTN\|\|HBGF8\|\|heparin-binding growth-associated molecule\|\|NEURITE OUTGROWTH-PROMOTING FACTOR, HEPARIN-BINDING\|\|HEPARIN-BINDING GROWTH FACTOR 8\|\|heparin affin regulatory protein\|\|pleiotrophin (heparin binding growth factor 8, neurite growth-promoting factor 1)\|\| | 0.46 | NM_002825 |
| FCER1A | \|\|FCER1A\|\|FCE1A\|\|FcERI\|\|Fc-epsilon RI-alpha\|\|Fc IgE receptor, alpha polypeptide\|\|Fc IgE RECEPTOR, ALPHA CHAIN\|\|high affinity immunoglobulin epsilon receptor alpha-subunit\|\|immunoglobulin E receptor, high-affinity, of mast cells, alpha polypeptide\|\|Fc fragment of IgE, high affinity I, receptor for; alpha polypeptide\|\|Fc FRAGMENT OF IgE, HIGH AFFINITY I, RECEPTOR FOR, ALPHA SUBUNIT\|\|Fc fragment of IgE, high affinity I, receptor for; alpha polypeptide precursor\|\| | 0.457 | NM_002001 |
| PTN | \|\|HARP\|\|HBNF\|\|NEGF1\|\|PTN\|\|HBGF8\|\|heparin-binding growth-associated molecule\|\|NEURITE OUTGROWTH-PROMOTING FACTOR, HEPARIN-BINDING\|\|HEPARIN-BINDING GROWTH FACTOR 8\|\|heparin affin regulatory protein\|\|pleiotrophin (heparin binding growth factor 8, neurite growth-promoting factor 1)\|\| | 0.435 | NM_002825 |
| IL1RN | \|\|MGC10430\|\|IL1RA\|\|IL1RN\|\|IRAP\|\|ICIL-1RA\|\|IL1F3\|\|interleukin 1 receptor antagonist\|\|intracellular IL-1 receptor antagonist type II\|\|interleukin 1 receptor antagonist isoform 2\|\|interleukin 1 receptor antagonist isoform 3\|\|interleukin 1 receptor antagonist isoform 4\|\|interleukin 1 receptor antagonist isoform 1 precursor\|\| | 0.43 | NM_173843 |
| HNMT | \|\|HNMT\|\|2.1.1.8\|\|histamine N-methyltransferase\|\| | 0.421 | NM_006895 |
| IL12A | \|\|NKSF1\|\|IL12A\|\|NFSK\|\|IL-12A\|\|CLMF\|\|interleukin 12, p35\|\|interleukin 12A precursor\|\|IL12, SUBUNIT p35\|\|IL-12, subunit p35\|\|interleukin-12 alpha chain precursor\|\|NF cell stimulatory factor chain 1\|\|NATURAL KILLER CELL STIMULATORY FACTOR, 35-KD SUBUNIT\|\|natural killer cell stimulatory factor 1, 35 kD subunit\|\|interleukin 12A (natural killer cell stimulatory factor 1, cytotoxic lymphocyte maturation factor 1, p35)\|\| | 0.405 | NM_000882 |

TABLE 9-continued

Mast cell related genes

| Common Name | Description | Fold Increase in EE | Genbank Accession number |
|---|---|---|---|
| CXCL14 | \|\|BMAC\|\|NJAC\|\|KS1\|\|Kec\|\|bolekine\|\|CXCL14\|\|MGC10687\|\|MIP-2g\|\|SCYB14, FORMERLY\|\|chemokine (C-X-C motif) ligand 14\|\|small inducible cytokine B14 precursor\|\|CHEMOKINE, CXC MOTIF, LIGAND 14\|\|CXC chemokine in breast and kidney\|\|SMALL INDUCIBLE CYTOKINE SUBFAMILY B, MEMBER 14, FORMERLY\|\|small inducible cytokine subfamily B (Cys-X-Cys), member 14 (BRAK)\|\| | 0.394 | NM_004887 |
| IL13RA1 | \|\|IL-13Ra\|\|IL13RA1\|\|CD213a1 antigen\|\|INTERLEUKIN 13 RECEPTOR, ALPHA-1\|\|IL13 receptor alpha-1 chain\|\|NR4, MOUSE, HOMOLOG OF\|\|interleukin 13 receptor, alpha 1\|\|interleukin 13 receptor, alpha 1 precursor\|\| | 0.39 | NM_001560 |
| IL1RN | \|\|MGC10430\|\|IL1RA\|\|IL1RN\|\|IRAP\|\|ICIL-1RA\|\|IL1F3\|\|interleukin 1 receptor antagonist\|\|intracellular IL-1 receptor antagonist type II\|\|interleukin 1 receptor antagonist isoform 2\|\|interleukin 1 receptor antagonist isoform 3\|\|interleukin 1 receptor antagonist isoform 4\|\|interleukin 1 receptor antagonist isoform 1 precursor\|\| | 0.377 | NM_173843 |
| LTB4DH | \|\|LTB4DH\|\|MGC34943\|\|leukotriene B4 12-hydroxydehydrogenase\|\|NADP-dependent leukotriene B4 12-hydroxydehydrogenase\|\| | 0.358 | NM_012212 |
| IL1F5 | \|\|FIL1D\|\|FIL1(DELTA)\|\|IL1HY1\|\|MGC29840\|\|IL1F5\|\|FIL1-DELTA\|\|IL1L1\|\|IL1RP3\|\|IL-1ra homolog\|\|interleukin-1 HY1\|\|interleukin 1, delta\|\|interleukin-1-like protein 1\|\|IL-1 related protein 3\|\|family of interleukin 1-delta\|\|interleukin-1 receptor antagonist homolog 1\|\|interleukin 1 family, member 5 (delta)\|\|INTERLEUKIN 1 RECEPTOR ANTAGONIST HOMOLOG 1\|\| | 0.348 | NM_012275 |
| IL18 | \|\|IL-1g\|\|IGIF\|\|IL1F4\|\|MGC12320\|\|IL-18\|\|IL18\|\|interleukin-1 gamma\|\|IL-1 gamma\|\|interleukin 18 proprotein\|\|interleukin 18 (interferon-gamma-inducing factor)\|\| | 0.341 | NM_001562 |
| IL8RB | \|\|IL8R2\|\|IL8RA\|\|IL8RB\|\|CMKAR2\|\|CDw128b\|\|GRO/MGSA receptor\|\|CHEMOKINE (C-X-C) RECEPTOR 2\|\|chemokine (CXC) receptor 2\|\|interleukin 8 receptor beta\|\|interleukin 8 receptor, beta\|\|interleukin 8 receptor type 2\|\|INTERLEUKIN 8 RECEPTOR, TYPE 2\|\|high affinity interleukin-8 receptor B\|\|CXCR2 gene for IL8 receptor type B\|\| | 0.214 | NM_001557 |
| ALOX12 | \|\|\|\|12(S)-lipoxygenase\|\|12-@LIPOXYGENASE\|\|1.13.11.31\|\|ALOX12\|\|LOG12\|\|12@LO\|\|ARACHIDONATE 12-OXIDOREDUCTASE\|\|arachidonate 12-lipoxygenase\|\| | 0.105 | NM_000697 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09982303B2). An electronic copy of the "Sequence Listing" will also be available from the USPTO upon request and payment of the fee set forth in 37 CFR 1.19(b)(3).

The invention claimed is:

1. A method for diagnosing and treating eosinophilic esophagitis in a patient in need thereof, the method comprising
    (i) measuring the gene expression level for at least one gene in an esophageal biopsy sample from the patient, the at least one gene selected from the group consisting of: chemokine ligand 26; periostin, osteoblast specific factor; tumor necrosis factor, alpha-induced protein 6; cadherin-like 26; arachidonate 15-lipoxygenase; pro-melanin-concentrating hormone; chemokine ligand 1; immunoglobulin lambda joining 3; transmembrane protein 16A; apolipoprotein B mRNA editing enzyme, catalytic polypeptide-like 3A; immunoglobulin heavy constant gamma 1; FLJ16025protein; ubiquitin D; immunoglobulin J polypeptide, linker protein for immunoglobulin; hypothetical protein FLJ33069; carboxypeptidase A3; similar to immunoglobulin kappa light chain variable region 011; Charcot-Leyden crystal protein; hypothetical protein MGC27165; pleckstrin homology-like domain, family B, member 2; hypothetical protein FLJ23259; immunoglobulin kappa constant; epiplakin1; and chemokine ligand 6,
    wherein the measuring the gene expression level is performed by a method comprising DNA microarray analysis, polymerase chain reaction analysis, or both,
    (ii) comparing the gene expression level for the at least one gene to its expression level in an esophageal biopsy sample from a normal individual defined as having zero eosinophils per high power field and no basal layer expansion;
    (iii) diagnosing eosinophilic esophagitis in the patient where the expression level of the at least one gene is increased more than 10-fold compared to its expression level in the esophageal biopsy sample from a normal individual,
    and
    (iv) treating the eosinophilic esophagitis in the patient diagnosed according to step (iii) with one or more therapies selected from an anti-inflammatory therapy, allergen elimination, and an eotaxin-3 and/or CCR3 blocker.

2. The method of claim 1, wherein the step of measuring gene the expression level is carried out using an oligonucleotide-based DNA microarray chip.

3. The method of claim 1, further comprising a step of extracting RNA from the esophageal biopsy sample.

4. The method of claim 3, further comprising a step of converting the RNA to cDNA.

5. The method of claim 4, further comprising a step of converting the cDNA to biotinylated cRNA.

6. The method of claim 5, further comprising hybridizing the biotinylated cRNA to an oligonucleotide-based DNA microarray chip.

* * * * *